United States Patent
Ferrone et al.

(10) Patent No.: US 11,078,260 B2
(45) Date of Patent: *Aug. 3, 2021

(54) ANTIBODIES TO ENDOPLASMIN AND THEIR USE

(71) Applicant: University of Pittsburgh—Of The Commonwealth System of Higher Education, Pittsburgh, PA (US)

(72) Inventors: Soldano Ferrone, Boston, MA (US); Xinhui Wang, Boston, MA (US); Thomas P. Conrads, Reston, VA (US); Elvira Favoino, Bari (IT); Brian L. Hood, Reston, VA (US)

(73) Assignee: University of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 264 days.

This patent is subject to a terminal disclaimer.

(21) Appl. No.: 15/870,532

(22) Filed: Jan. 12, 2018

(65) Prior Publication Data
US 2018/0230205 A1    Aug. 16, 2018

Related U.S. Application Data

(63) Continuation of application No. 15/092,520, filed on Apr. 6, 2016, now Pat. No. 9,902,766, which is a continuation of application No. 13/929,671, filed on Jun. 27, 2013, now Pat. No. 9,340,608, which is a
(Continued)

(51) Int. Cl.
| | |
|---|---|
| *C07K 16/18* | (2006.01) |
| *C07K 16/30* | (2006.01) |
| *C07K 16/46* | (2006.01) |
| *A61K 47/68* | (2017.01) |
| *G01N 33/574* | (2006.01) |
| *G01N 33/577* | (2006.01) |
| *A61K 39/00* | (2006.01) |
| *C12N 15/86* | (2006.01) |
| *C12N 15/82* | (2006.01) |
| *C12N 15/62* | (2006.01) |
| *C12N 15/09* | (2006.01) |
| *C12N 5/10* | (2006.01) |

(52) U.S. Cl.
CPC .......... *C07K 16/18* (2013.01); *A61K 47/6843* (2017.08); *C07K 16/30* (2013.01); *C07K 16/303* (2013.01); *C07K 16/3015* (2013.01); *C07K 16/3023* (2013.01); *C07K 16/3038* (2013.01); *C07K 16/3053* (2013.01); *C07K 16/3069* (2013.01); *C07K 16/3092* (2013.01); *G01N 33/574* (2013.01); *G01N 33/577* (2013.01); *A61K 39/00* (2013.01); *C07K 2317/21* (2013.01); *C07K 2317/34* (2013.01); *C07K 2317/54* (2013.01); *C07K 2317/55* (2013.01); *C07K 2317/622* (2013.01); *C07K 2317/624* (2013.01); *C07K 2317/73* (2013.01); *C07K 2317/732* (2013.01); *C07K 2317/734* (2013.01); *C07K 2319/55* (2013.01); *C07K 2319/60* (2013.01); *C12N 5/10* (2013.01); *C12N 15/09* (2013.01); *C12N 15/62* (2013.01); *C12N 15/8258* (2013.01); *C12N 15/86* (2013.01); *C12N 2800/00* (2013.01); *C12N 2810/859* (2013.01); *G01N 2333/47* (2013.01); *G01N 2333/4727* (2013.01); *G01N 2800/7028* (2013.01)

(58) Field of Classification Search
CPC .... C07K 16/18; C07K 16/30; C07K 16/3015; C07K 16/303; C07K 16/3038; C07K 16/3053; C07K 16/3069; C07K 16/3092; C07K 2317/21; C07K 2317/34; C07K 2317/55; C07K 2317/622; C07K 2317/624; C07K 2317/73; C07K 2317/732; C07K 2317/734
See application file for complete search history.

(56) References Cited

U.S. PATENT DOCUMENTS

| | | |
|---|---|---|
| 8,497,354 B2 | 7/2013 | Ferrone et al. |
| 8,771,687 B2 | 7/2014 | Ferrone et al. |
| 2004/0001789 A1 | 1/2004 | Young et al. |

(Continued)

FOREIGN PATENT DOCUMENTS

| | | |
|---|---|---|
| WO | WO 2004/087205 A1 | 10/2004 |
| WO | WO 2004112834 A1 | 12/2004 |

(Continued)

OTHER PUBLICATIONS

Khantasup et al., Monoclonal Antibodies in Immunodiagnosis and Immunotherapy, 2015, 34(6): 404-417.*
(Continued)

*Primary Examiner* — Hong Sang
(74) *Attorney, Agent, or Firm* — Klarquist Sparkman, LLP

(57) ABSTRACT

Isolated monoclonal antibodies are disclosed herein that specifically bind endoplasmin. In some embodiments these antibodies are fully human. Recombinant nucleic acids encoding these antibodies, expression vectors including these nucleic acids, and host cells transformed with these expression vectors are also disclosed herein. In several embodiments the disclosed antibodies are of use for detecting and/or treating tumors that express endoplasmin, such as melanoma, breast cancer, head and neck squamous cell carcinoma, renal cancer, lung cancer, glioma, bladder cancer, ovarian cancer or pancreatic cancer. In one example, the tumor is a melanoma.

15 Claims, 28 Drawing Sheets
Specification includes a Sequence Listing.

Related U.S. Application Data continuation of application No. 13/161,432, filed on Jun. 15, 2011, now Pat. No. 8,497,354.

(60) Provisional application No. 61/355,516, filed on Jun. 16, 2010.

(56) References Cited

U.S. PATENT DOCUMENTS

| | | |
|---|---|---|
| 2005/0008649 A1 | 1/2005 | Shin |
| 2005/0053666 A1 | 3/2005 | Tzannis et al. |

FOREIGN PATENT DOCUMENTS

| | | | |
|---|---|---|---|
| WO | WO 2006/120230 | A2 | 11/2006 |
| WO | WO 2009/039409 | A1 | 3/2009 |
| WO | WO 2009/113074 | A1 | 9/2009 |
| WO | WO 2012/075324 | A1 | 6/2012 |

OTHER PUBLICATIONS

Al-Lazikani et al., "Standard conformations for the canonical structures of immunoglobulins," *J. Mol. Biol.* 273:927-948 (1997).

Arnold-Schild et al., "One-step single-chain Fv recombinant antibody-based purification of gp96 for vaccine development," *Cancer Research* 60:4175-4178 (Aug. 1, 2000).

Bendig "Humanization of rodent monoclonal antibodies by CDR grafting," *Methods: A Companion to Methods on Enzymology* 8:83-93 (1995).

Brochet et al., "IMGT/V-QUEST: the highly customized and integrated system for IG and TR standardized V-J and V-D-J sequence analysis," *Nucleic Acids Research* 36:W503-W508 (2008).

Colman, "Effects of amino acid sequence changes on antibody-antigen interaction," *Research in Immunology* 145:33-36 (1994).

International Search Report from parent PCT Application No. PCT/US2011/040580, 4 pages (completed on Aug. 31, 2011).

Johnson et al., "The Kabat database and a bioinformatics example," *Methods in Mol. Biol.* 248:11-25 (2004).

Lefranc et al., "IMGT unique numbering for immunoglobulin and T cell receptor variable domains and Ig superfamily V-like domains," *Dev. Comp. Immunobiol.*, 27:55-77 (2003).

Lefranc et al., printout from the IMGT home page, www.imgt.org, as updated Jun. 25, 2012.

Paul, *Fundamental Immunology*, $3^{rd}$ *Edition*, 292-295 (1993).

Rudikoff et al., "Single amino acid substitution altering antigen-binding specificity," *Proc. Natl. Acad. Sci. USA* 79(6):1979-1983 (Mar. 1982).

\* cited by examiner

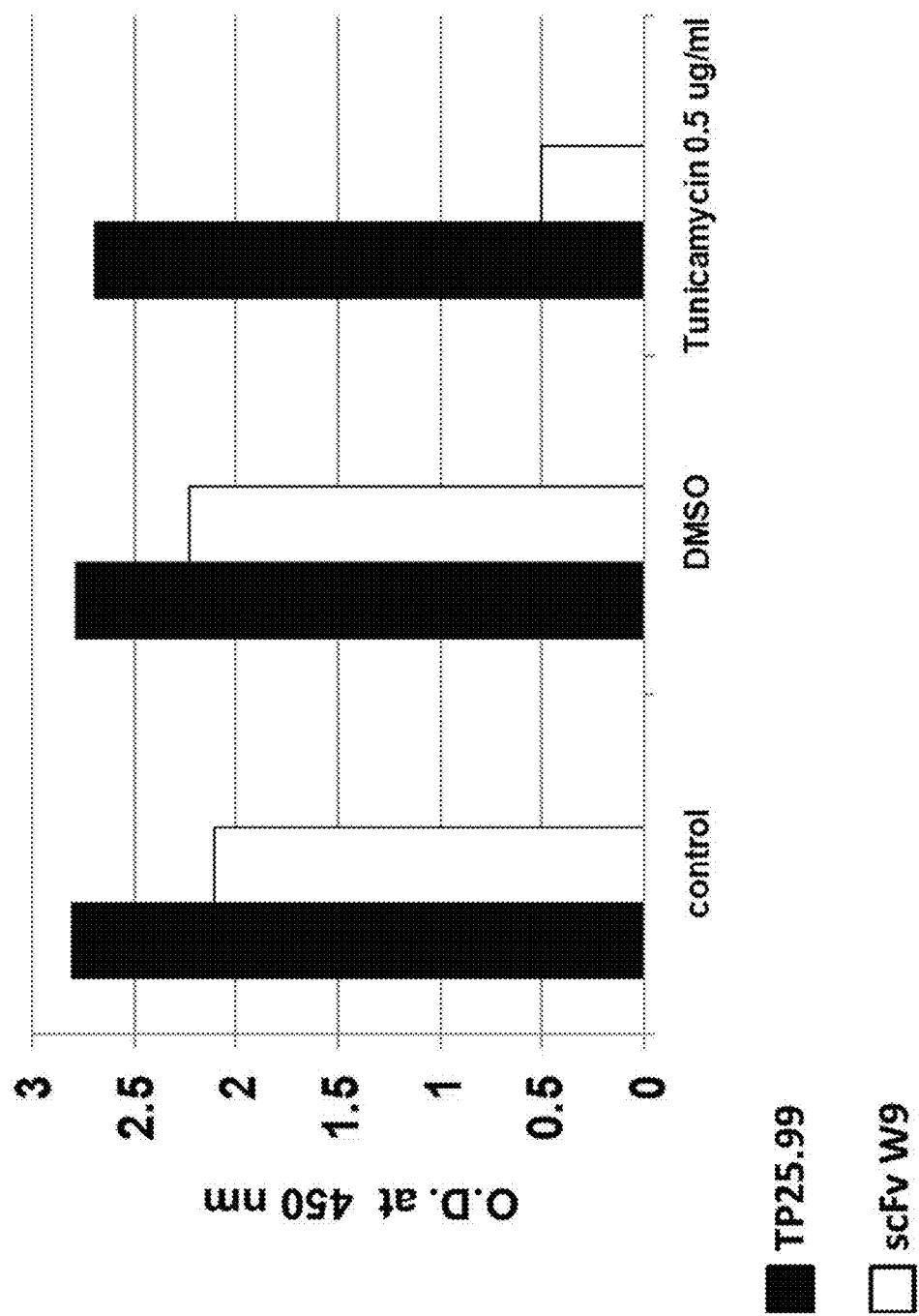

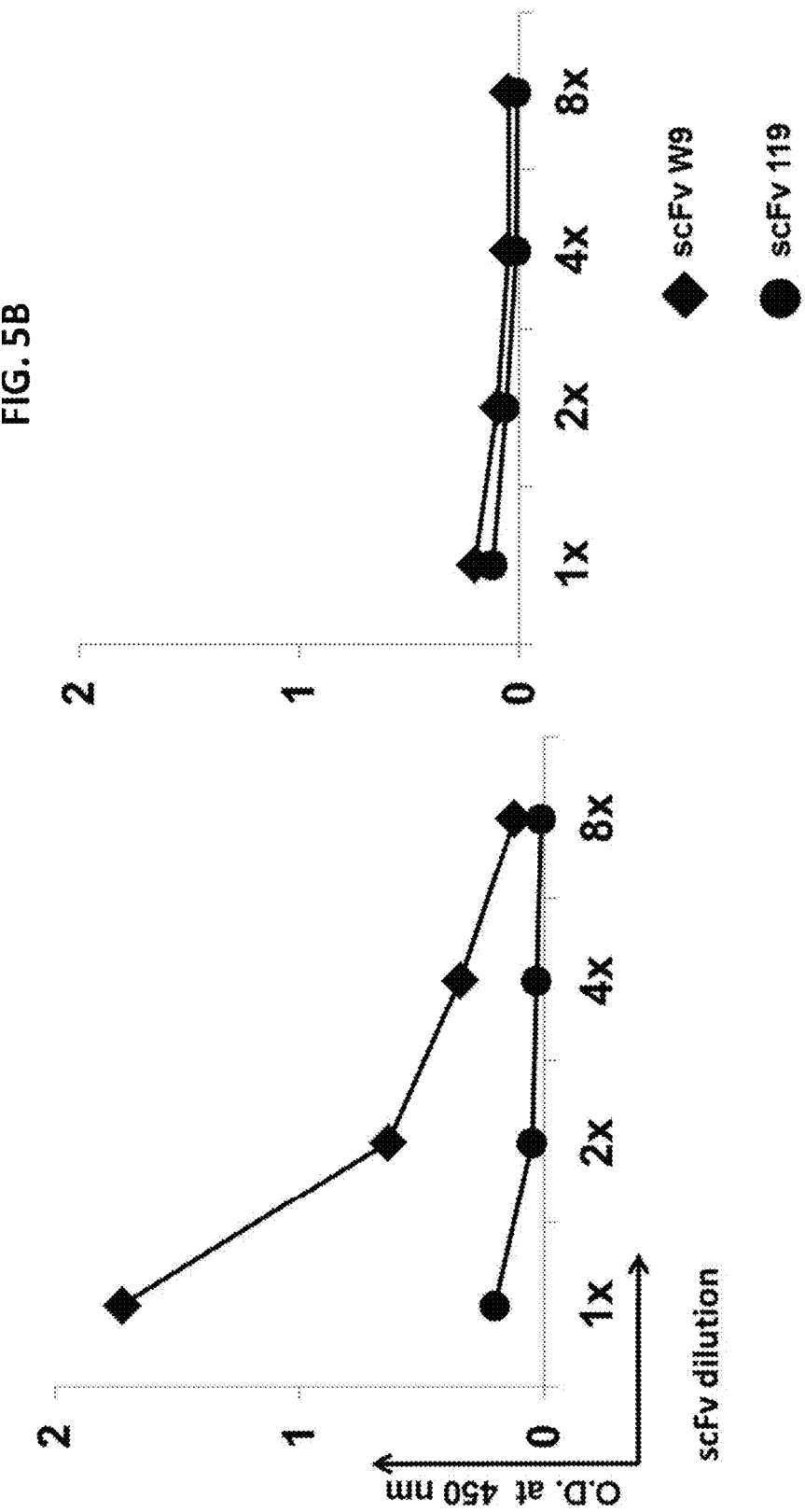

— untransfected
--- transfected

FIG. 12
MDA-MB-231
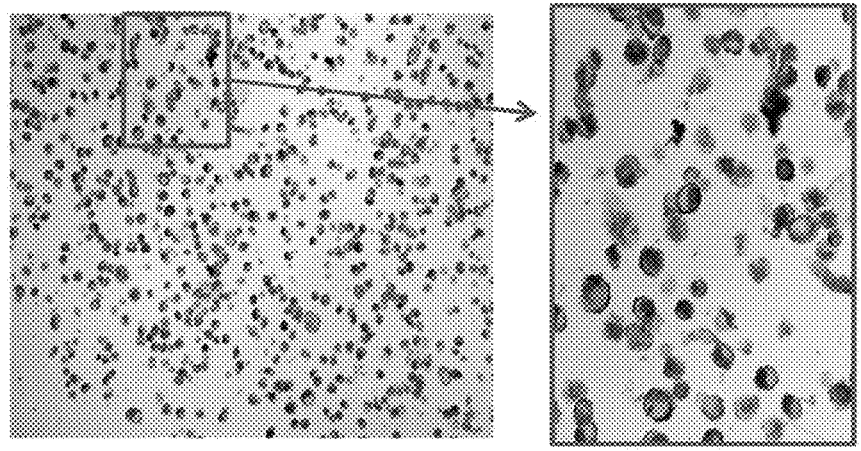
MCF-7 (negative control)
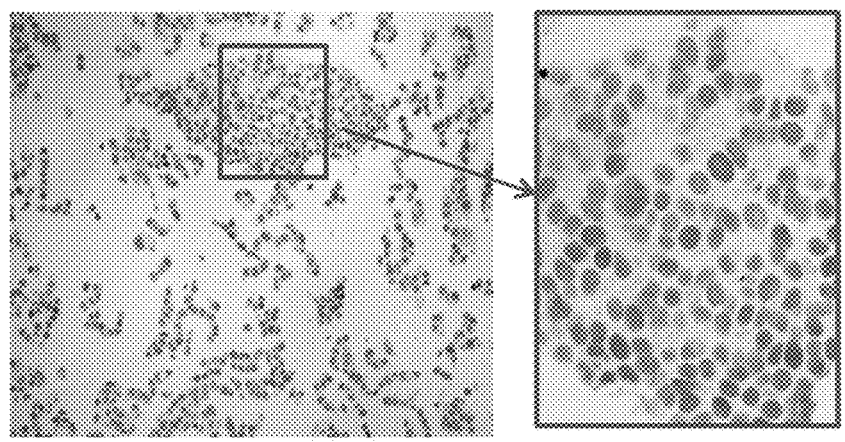
MV3 Xenograft
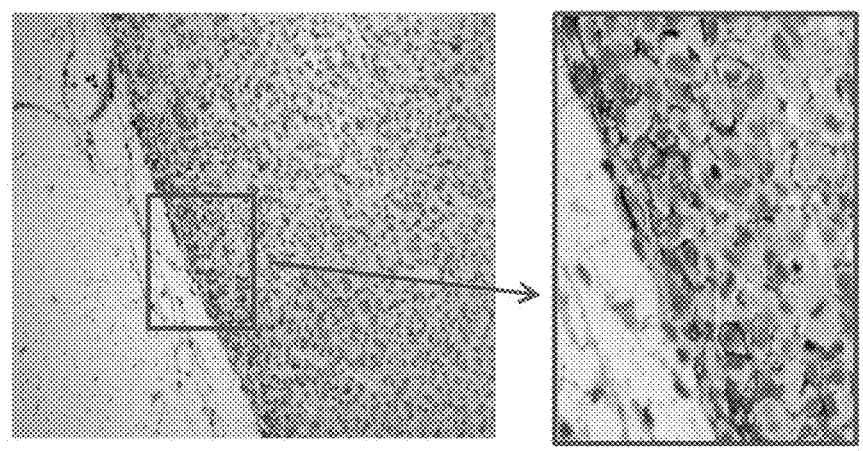

a. % density increase using control cells as a reference.

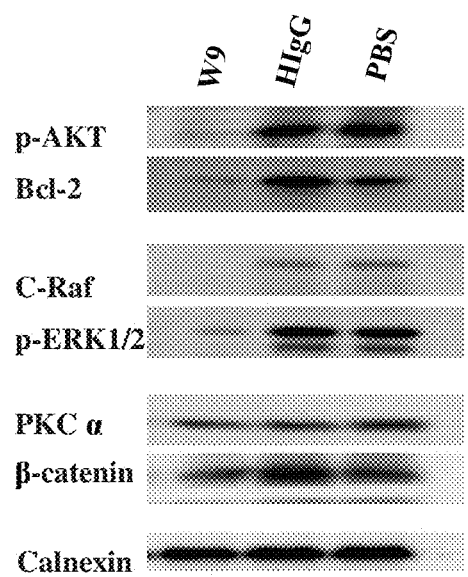
FIG. 22
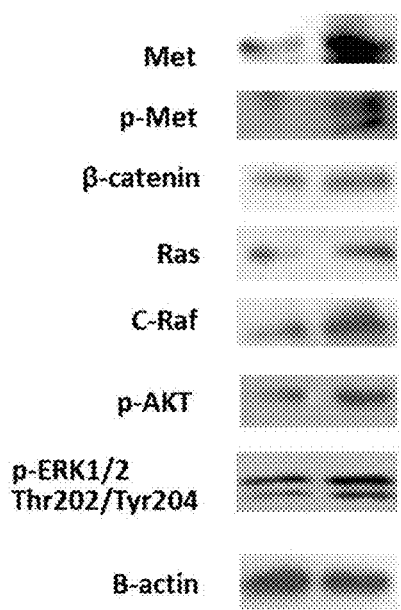

FIG. 23
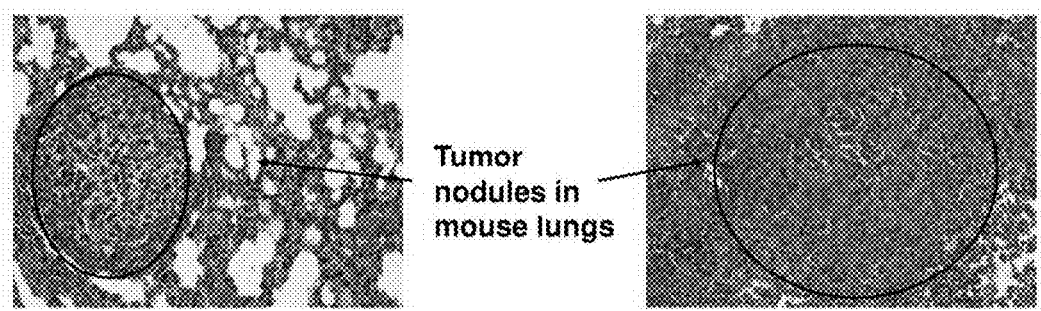
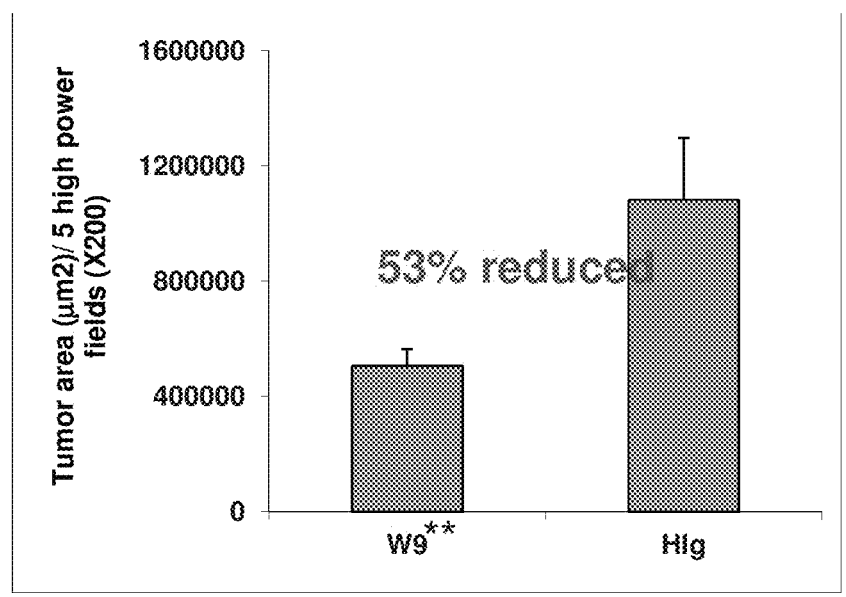

SEQUENCE LISTING

<160> NUMBER OF SEQ ID NOS: 8

<210> SEQ ID NO 1
<211> LENGTH: 445
<212> TYPE: PRT
<213> ORGANISM: Homo sapiens

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala His Phe Asp Tyr Trp Gly Gln Gly Thr Leu Val Thr Val
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

```
Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met Glu Thr His Glu Ala Leu His Asn
                420                 425                 430

His Tyr Thr Gln Lys Ser Leu Ser Leu Ser Pro Gly Lys
                435                 440                 445

<210> SEQ ID NO 2
<211> LENGTH: 213
<212> TYPE: PRT
<213> ORGANISM: Homo sapiens

<400> SEQUENCE: 2

Glu Ile Glu Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 3
<211> LENGTH: 1332
<212> TYPE: DNA
<213> ORGANISM: Homo sapiens

<400> SEQUENCE: 3
caggtgcagc tggtgcagtc tggggctgag gtgaagaagc ctggggcctc agtgaaggtt      60
tcctgcaagg cttctggata caccttcact agctatgcta tgcattgggt gcgccaggcc     120
cccggacaaa ggcttgagtg gatgggatgg atcaacgctg gcaatggtaa cacaaaatat     180
```

-continued

```
tcacagaagt tccagggcag agtcaccatt accagggaca catccgcgag cacagcctac      240
atggagctga gcagcctgag atctgaagac acggccgtgt attactgtgc aagggcccat      300
tttgactact ggggccaagg taccctggtc accgtctcgg ctagcaccaa gggcccatcg      360
gtcttccccc tggcaccctc ctccaagagc acctctgggg cacagcggc cctgggctgc       420 ctggtcaagg actacttccc cgaaccggtg acggtgtcgt ggaactcagg cgccctgacc      480
agcggcgtgc acaccttccc ggctgtccta cagtcctcag gactctactc cctcagcagc      540
gtggtgaccg tgccctccag cagcttgggc acccagacct acatctgcaa cgtgaatcac      600
aagcccagca acaccaaggt ggacaagaaa gttgagccca atcttgtga caaaactcac       660 acatgcccac cgtgcccagc acctgaactc ctggggggac cgtcagtctt cctcttcccc      720
ccaaaaccca aggacaccct catgatctcc cggacccctg aggtcacatg cgtggtggtg      780
gacgtgagcc acgaagaccc tgaggtcaag ttcaactggt acgtggacgg cgtggaggtg      840
cataatgcca agacaaagcc gcgggaggag cagtacaaca gcacgtaccg tgtggtcagc      900
gtcctcaccg tcctgcacca ggactggctg aatggcaagg agtacaagtg caaggtctcc      960
aacaaagccc tcccagcccc catcgagaaa accatctcca aagccaaagg gcagccccga     1020
gaaccacagg tgtacaccct gcccccatcc cgggaggaga tgaccaagaa ccaggtcagc     1080
ctgacctgcc tggtcaaagg cttctatccc agcgacatcg ccgtggagtg ggagagcaat     1140
gggcagccgg agaacaacta caagaccacg cctcccgtgc tggactccga cggctccttc     1200
ttcctctaca gcaagctcac cgtggacaag agcaggtggc agcaggggaa cgtcttctca     1260
tgctccgtga tgcatgaggc tctgcacaac cactacacgc agaagagcct ctccctgtct     1320
ccgggtaaat ga                                                         1332
```

<210> SEQ ID NO 4
<211> LENGTH: 642
<212> TYPE: DNA
<213> ORGANISM: Homo sapiens

<400> SEQUENCE: 4

```
gaaattgagc tcacccagtc tccatcctcc ctgtctgcat ctgtaggaga cagagtcacc       60
atcacttgcc gggcaagtca gagcattagc agctacttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta cccctccaac gttcggccaa      300
gggaccaagg tggagatcaa aacggtggct gcaccatctg tcttcatctt cccgccatct      360
gatgagcagt tgaaatctgg aactgcctct gttgtgtgcc tgctgaataa cttctatccc      420
agagaggcca aagtacagtg gaaggtggat aacgccctcc aatcgggtaa ctcccaggag      480
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttcaacagg ggagagtgtt ag                         642
```

<210> SEQ ID NO 5
<211> LENGTH: 803
<212> TYPE: PRT
<213> ORGANISM: Homo sapiens

<400> SEQUENCE: 5

Met Arg Ala Leu Trp Val Leu Gly Leu Cys Cys Val Leu Leu Thr Phe

-continued

```
1               5                   10                  15
Gly Ser Val Arg Ala Asp Asp Glu Val Asp Val Asp Gly Thr Val Glu
                20                  25                  30
Glu Asp Leu Gly Lys Ser Arg Glu Gly Ser Arg Thr Asp Asp Glu Val
                35                  40                  45
Val Gln Arg Glu Glu Ala Ile Gln Leu Asp Gly Leu Asn Ala Ser
 50                  55                  60
Gln Ile Arg Glu Leu Arg Glu Lys Ser Glu Lys Phe Ala Phe Gln Ala
 65                  70                  75                  80
Glu Val Asn Arg Met Met Lys Leu Ile Ile Asn Ser Leu Tyr Lys Asn
                85                  90                  95
Lys Glu Ile Phe Leu Arg Glu Leu Ile Ser Asn Ala Ser Asp Ala Leu
                100                 105                 110
Asp Lys Ile Arg Leu Ile Ser Leu Thr Asp Glu Asn Ala Leu Ser Gly
                115                 120                 125
Asn Glu Glu Leu Thr Val Lys Ile Lys Cys Asp Lys Glu Lys Asn Leu
 130                 135                 140
Leu His Val Thr Asp Thr Gly Val Gly Met Thr Arg Glu Glu Leu Val
145                 150                 155                 160
Lys Asn Leu Gly Thr Ile Ala Lys Ser Gly Thr Ser Glu Phe Leu Asn
                165                 170                 175
Lys Met Thr Glu Ala Gln Glu Asp Gly Gln Ser Thr Ser Glu Leu Ile
                180                 185                 190
Gly Gln Phe Gly Val Gly Phe Tyr Ser Ala Phe Leu Val Ala Asp Lys
                195                 200                 205
Val Ile Val Thr Ser Lys His Asn Asn Asp Thr Gln His Ile Trp Glu
 210                 215                 220
Ser Asp Ser Asn Glu Phe Ser Val Ile Ala Asp Pro Arg Gly Asn Thr
225                 230                 235                 240
Leu Gly Arg Gly Thr Thr Ile Thr Leu Val Leu Lys Glu Glu Ala Ser
                245                 250                 255
Asp Tyr Leu Glu Leu Asp Thr Ile Lys Asn Leu Val Lys Lys Tyr Ser
                260                 265                 270
Gln Phe Ile Asn Phe Pro Ile Tyr Val Trp Ser Ser Lys Thr Glu Thr
                275                 280                 285
Val Glu Glu Pro Met Glu Glu Glu Ala Ala Lys Glu Glu Lys Glu
                290                 295                 300
Glu Ser Asp Asp Glu Ala Ala Val Glu Glu Glu Glu Glu Lys Lys
305                 310                 315                 320
Pro Lys Thr Lys Lys Val Glu Lys Thr Val Trp Asp Trp Glu Leu Met
                325                 330                 335
Asn Asp Ile Lys Pro Ile Trp Gln Arg Pro Ser Lys Glu Val Glu Glu
                340                 345                 350
Asp Glu Tyr Lys Ala Phe Tyr Lys Ser Phe Ser Lys Glu Ser Asp Asp
                355                 360                 365
Pro Met Ala Tyr Ile His Phe Thr Ala Glu Gly Glu Val Thr Phe Lys
 370                 375                 380
Ser Ile Leu Phe Val Pro Thr Ser Ala Pro Arg Gly Leu Phe Asp Glu
385                 390                 395                 400
Tyr Gly Ser Lys Lys Ser Asp Tyr Ile Lys Leu Tyr Val Arg Arg Val
                405                 410                 415
Phe Ile Thr Asp Asp Phe His Asp Met Met Pro Lys Tyr Leu Asn Phe
                420                 425                 430
```

Val Lys Gly Val Val Asp Ser Asp Asp Leu Pro Leu Asn Val Ser Arg
        435                 440                 445

Glu Thr Leu Gln Gln His Lys Leu Leu Lys Val Ile Arg Lys Lys Leu
    450                 455                 460

Val Arg Lys Thr Leu Asp Met Ile Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
                500                 505                 510

Gln Ser Ser His His Pro Thr Asp Ile Thr Ser Leu Asp Gln Tyr Val
            515                 520                 525

Glu Arg Met Lys Glu Lys Gln Asp Lys Ile Tyr Phe Met Ala Gly Ser
        530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
                580                 585                 590

Lys Glu Gly Val Lys Phe Asp Glu Ser Glu Lys Thr Lys Glu Ser Arg
            595                 600                 605

Glu Ala Val Glu Lys Glu Phe Glu Pro Leu Leu Asn Trp Met Lys Asp
        610                 615                 620

Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Gly Trp Ser Gly
                645                 650                 655

Asn Met Glu Arg Ile Met Lys Ala Gln Ala Tyr Gln Thr Gly Lys Asp
                660                 665                 670

Ile Ser Thr Asn Tyr Tyr Ala Ser Gln Lys Lys Thr Phe Glu Ile Asn
            675                 680                 685

Pro Arg His Pro Leu Ile Arg Asp Met Leu Arg Arg Ile Lys Glu Asp
        690                 695                 700

Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
                740                 745                 750

Ala Lys Val Glu Glu Glu Pro Glu Glu Glu Pro Glu Glu Thr Ala Glu
            755                 760                 765

Asp Thr Thr Glu Asp Thr Glu Gln Asp Glu Asp Glu Glu Met Asp Val
        770                 775                 780

Gly Thr Asp Glu Glu Glu Glu Thr Ala Lys Glu Ser Thr Ala Glu Lys
785                 790                 795                 800

Asp Glu Leu

<210> SEQ ID NO 6
<211> LENGTH: 2780
<212> TYPE: DNA
<213> ORGANISM: Homo sapiens

<400> SEQUENCE: 6

-continued

```
gtgggcggac cgcgcggctg gaggtgtgag gatccgaacc cagggtgggg gggtggaggc      60
ggctcctgcg atcgaagggg acttgagact caccggccgc acgccatgag ggccctgtgg     120
gtgctgggcc tctgctgcgt cctgctgacc ttcgggtcgg tcagagctga cgatgaagtt     180
gatgtggatg gtacagtaga agaggatctg ggtaaaagta gagaaggatc aaggacggat     240
gatgaagtag tacagagaga ggaagaagct attcagttgg atggattaaa tgcatcacaa     300
ataagagaac ttagagagaa gtcggaaaag tttgccttcc aagccgaagt taacagaatg     360
atgaaactta tcatcaattc attgtataaa aataaagaga ttttcctgag agaactgatt     420
tcaaatgctt ctgatgcttt agataagata aggctaatat cactgactga tgaaaatgct     480
ctttctggaa atgaggaact aacagtcaaa attaagtgtg ataaggagaa gaacctgctg     540
catgtcacag acaccggtgt aggaatgacc agagaagagt tggttaaaaa ccttggtacc     600
atagccaaat ctgggacaag cgagtttttta aacaaaatga ctgaagcaca ggaagatggc     660
cagtcaactc ctgaattgat tggccagttt ggtgtcggtt tctattccgc cttccttgta     720
gcagataagg ttattgtcac ttcaaaacac aacaacgata cccagcacat ctgggagtct     780
gactccaatg aattttctgt aattgctgac ccaagaggaa acactctagg acggggaacg     840
acaattaccc ttgtcttaaa agaagaagca tctgattacc ttgaattgga tacaattaaa     900
aatctcgtca aaaatattc acagttcata aactttccta tttatgtatg gagcagcaag     960
actgaaactg ttgaggagcc catggaggaa gaagaagcag ccaaagaaga gaaagaagaa    1020
tctgatgatg aagctgcagt agaggaagaa gaagaagaaa agaaaccaaa gactaaaaaa    1080
gttgaaaaaa ctgtctggga ctgggaactt atgaatgata tcaaaccaat atggcagaga    1140
ccatcaaaag aagtagaaga agatgaatac aaagctttct acaaatcatt ttcaaaggaa    1200
agtgatgacc ccatggctta tattcacttt actgctgaag gggaagttac cttcaaatca    1260
attttatttg tacccacatc tgctccacgt ggtctgtttg acgaatatgg atctaaaaag    1320
agcgattaca ttaagctcta tgtgcgccgt gtattcatca cagacgactt ccatgatatg    1380
atgcctaaat acctcaattt tgtcaagggg gtggtggact cagatgatct ccccttgaat    1440
gtttcccgcg agactcttca gcaacataaa ctgcttaagg tgattaggaa gaagcttgtt    1500
cgtaaaacgc tggacatgat caagaagatt gctgatgata aatacaatga tactttttgg    1560
aaagaatttg gtaccaacat caagcttggt gtgattgaag accactcgaa tcgaacacgt    1620
cttgctaaac ttcttaggtt ccagtcttct catcatccaa ctgacattac tagcctagac    1680
cagtatgtgg aaagaatgaa ggaaaaacaa gacaaaatct acttcatggc tgggtccagc    1740
agaaaagagg ctgaatcttc tccatttgtt gagcgacttc tgaaaaaggg ctatgaagtt    1800
atttacctca cagaacctgt ggatgaatac tgtattcagg cccttcccga atttgatggg    1860
aagaggttcc agaatgttgc caaggaagga gtgaagttcg atgaaagtga gaaaactaag    1920
gagagtcgtg aagcagttga gaaagaattt gagcctctgc tgaattggat gaaagataaa    1980
gcccttaagg acaagattga aaaggctgtg gtgtctcagc gcctgacaga atctccgtgt    2040
gctttggtgg ccagccagta cggatggtct ggcaacatgg agagaatcat gaaagcacaa    2100
gcgtaccaaa cgggcaagga catctctaca aattactatg cgagtcagaa gaaaacatttt    2160 gaaattaatc ccagacaccc gctgatcaga gacatgcttc gacgaattaa ggaagatgaa    2220
gatgataaaa cagttttgga tcttgctgtg gttttgtttg aaacagcaac gcttcggtca    2280
gggtatcttt taccagacac taaagcatat ggagatagaa tagaaagaat gcttcgcctc    2340
```

```
agtttgaaca ttgaccctga tgcaaaggtg gaagaagagc ccgaagaaga acctgaagag    2400
acagcagaag acacaacaga agacacagag caagacgaag atgaagaaat ggatgtggga    2460
acagatgaag aagaagaaac agcaaaggaa tctacagctg aaaaagatga attgtaaatt    2520
atactctcac catttggatc ctgtgtggag agggaatgtg aaatttacat catttctttt    2580
tgggagagac ttgttttgga tgccccctaa tccccttctc ccctgcactg taaaatgtgg    2640
gattatgggt cacaggaaaa agtgggtttt ttagttgaat tttttttaac attcctcatg    2700
aatgtaaatt tgtactattt aactgactat tcttgatgta aaatcttgtc atgtgtataa    2760
aaataaaaaa gatcccaaat                                                2780

<210> SEQ ID NO 7
<211> LENGTH: 12
<212> TYPE: PRT
<213> ORGANISM: Homo sapiens

<400> SEQUENCE: 7

Glu Leu Ile Ser Asn Ala Ser Asp Ala Leu Asp Lys
1               5                   10

<210> SEQ ID NO 8
<211> LENGTH: 14
<212> TYPE: PRT
<213> ORGANISM: Homo sapiens

<400> SEQUENCE: 8

Gly Val Val Asp Ser Asp Asp Leu Pro Leu Asn Val Ser Arg
1               5                   10
```

ANTIBODIES TO ENDOPLASMIN AND THEIR USE

PRIORITY CLAIM

This is a continuation of U.S. patent application Ser. No. 15/092,520, filed on Apr. 6, 2016, which is a continuation of U.S. patent application Ser. No. 13/929,671, filed Jun. 27, 2013, issued as U.S. Pat. No. 9,340,608, which is a continuation of U.S. patent application Ser. No. 13/161,432, filed Jun. 15, 2011, issued as U.S. Pat. No. 8,497,354, which claims the benefit of U.S. Provisional Application No. 61/355,516, filed Jun. 16, 2010. The prior applications are incorporated by reference herein.

STATEMENT OF GOVERNMENT SUPPORT

This invention was made with government support under to Grant No. CA105500 and Grant No. CA138188 awarded by the National Institutes of Health. The government has certain rights in the invention.

FIELD

This relates to the field of antibodies, specifically to fully human antibodies that specifically bind endoplasmin.

BACKGROUND

Melanomas are aggressive, frequently metastatic tumors derived from either melanocytes or melanocyte related nevus cells ("Cellular and Molecular Immunology" (1991) (eds.) Abbas A. K., Lechtman, A. H., Pober, J. S.; W. B. Saunders Company, Philadelphia: pages 340-341). Melanomas make up approximately three percent of all skin cancers and the worldwide increase in melanoma is unsurpassed by any other neoplasm with the exception of lung cancer in women ("Cellular and Molecular Immunology" (1991) (eds.) Abbas, A. K., Lechtiman, A. H., Pober, J. S.; W. B. Saunders Company Philadelphia pages: 340-342; Kirkwood and Agarwala (1993) *Principles and Practice of Oncology* 7:1-16). Even when melanoma is apparently localized to the skin, up to 30% of the patients will develop systemic metastasis and the majority will die (Kirkwood and Agarwala (1993) *Principles and Practice of Oncology* 7:1-16). Classic modalities of treating melanoma include surgery, radiation and chemotherapy. In the past decade, immunotherapy and other molecular methods have emerged as new and promising methods for treating melanoma.

Strong evidence that an immune response to cancer exists in humans is provided by the existence of lymphocytes within melanoma deposits. These lymphocytes, when isolated, are capable of recognizing specific tumor antigens on autologous and allogeneic melanomas in a major histocompatibility complex (MHC)-restricted fashion (Itoh et al. (1986), *Cancer Res.* 46: 3011-3017; Muul et al. (1987), *J. Immunol.* 138:989-995); Topalian et al. (1989) *J. Immunol.* 142: 3714-3725; Darrow et al. (1989) *J. Immunol.* 142: 3329-3335; Hom et al. (1991) *J. Immunother.* 10:153-164; Kawakami et al. (1992) *J. Immunol.* 148: 638-643; Hom et al. (1993) *J. Immunother.* 13:18-30; O'Neil et al. (1993) *J. Immunol.* 151: 1410-1418). Tumor infiltrating lymphocytes (TIL) from patients with metastatic melanoma recognize shared antigens including melanocyte-melanoma lineage specific tissue antigens in vitro (Kawakami et al. (1993) *J. Immunother.* 14: 88-93; Anichini et al. (1993) *J. Exp. Med.* 177: 989-998). The fact that many melanoma patients mount cellular and humoral responses against these tumors and that melanomas express both MHC antigens and tumor associated antigens (TAA) suggests that identification and characterization of additional melanoma antigens will be important for immunotherapy of patients with melanoma. However, there remains a need for new modalities for the treatment of melanoma and other cancers.

SUMMARY

Isolated monoclonal antibodies and antigen binding fragments of these antibodies are disclosed herein that specifically bind endoplasmin (Grp94). In some embodiments these antibodies are fully human. These antibodies have a high affinity for human endoplamin and can be used to treat and/or diagnose cancer. In one example, the monoclonal antibody is an scFv.

In some embodiments the disclosed antibodies are of use for detecting tumors that express endoplasmin, such as melanoma, breast cancer, head and neck squamous cell carcinoma, renal cancer, lung cancer, glioma, bladder cancer, ovarian cancer or pancreatic cancer. In other embodiments, the disclosed antibodies are of use for treating a tumor, such as melanoma, breast cancer, head and neck squamous cell carcinoma, renal cancer, lung cancer, glioma, bladder cancer, ovarian cancer or pancreatic cancer.

Recombinant nucleic acids encoding these antibodies, expression vectors including these nucleic acids, and host cells transformed with these expression vectors are also disclosed herein.

The foregoing and other features and advantages will become more apparent from the following detailed description of several embodiments, which proceeds with reference to the accompanying figures.

BRIEF DESCRIPTION OF THE FIGURES

FIG. 4. Role of carbohydrates in the expression of the determinant recognized by scFv W9. COLO38 cells were cultured for 72 hours in the presence of 0.5 µg/ml of tunicamycin. Cells incubated in medium with DMSO alone, and the mAb TP25.99 were used as controls. Cells were tested by ELISA for the binding of scFv W9. Cells were incubated with scFv W9 for 2 hours at 4° C. The binding of scFv was detected using mAb 9E10 and HPR-goat anti-mouse IgG antibodies. Absorbance was read at 450 nm Tunicamycin treatment induced a strong decrease of scFv W9 binding to COLO38 cells. Thus, carbohydrates play a role in the expression of the determinant recognized by scFv W9.

FIGS. 5A and 5B. Specificity of the reactivity of scFv W9 to recombinant canine Endoplasmin (Grp94). Recombinant canine endoplasmin (Grp94), which displays a 98.5% homology in the amino acid sequence with human enodplasmin (Grp94), was immobilized in a 96-well plate at 20 µg/well and incubated with scFv W9 for 2 hours at room temperature. The binding of scFv was detected using mAb 9E10 and HPR-goat anti-mouse IgG antibodies. Absorbance was read at 450 nm. scFv 119 and BSA were used as negative controls. scFv W9 recognizes a determinant of endoplasmin expressed on the cell membrane.

FIG. 12. IHC staining analysis of endoplasmin (Grp94) expression on human basal breast cancer MDA-MB-231 and human melanoma xenograft MV3 by using mAb W9. Formalin fixed and paraffin embedded human basal breast cancer MDA-MB-231 cells, human luminal breast cancer MCF-7 cells and human melanoma xenograft MV3 were stained with mAb W9 (5 µg/ml) (×200). Immunoistochemical staining with mAb W9 showed that MDA-MB-231 cells and MV3 xenograft were strongly stained by mAb W9 (5 µg/ml). No staining was detected in the MCF-7 cells.

FIG. 21. Inhibition by mAb W9 of signaling pathways in human melanoma M21 cells. The human melanoma M21 cells were seeded at the concentration of $1.0 \times 10^5$ per well in a 6-well plate in RPMI 1640 medium with 5% FCS and incubated with mAb W9 (5 μg/ml) for 72 hrs. Cell lysate were tested in western blot with anti-phosphorylated (p)-AKT, Bcl-2, C-Raf, (p)-ERK1/2, PKCα, β-catenin mAbs. Human Ig (HIg) and PBS were used as negative controls. Calnexin was used as the loading control.

FIG. 22. Inhibition by mAb W9 of signaling pathways in human melanoma MV3 cells. Human melanoma MV3 cells were incubated with mAb W9 for 6 hrs at 37° C. in RPMI 1640. Cell lysate were then prepared and tested in western blot with anti-RAS, Met, p-Met, β-catenin, Ras, C-RAF, p-AKT, and p-ERK1/2. Thr202/Tyr204. β-actin was used as the loading control. Cells incubated with HIg were used as controls.

FIG. 23. Reduction of established lung metastasis in mice treated with mAb W9. MV3 melanoma cells ($1.4 \times 10^8$/mice) were injected i.v.. After 15 days mice were treated with mAb W9 (100 μg/mice, i.v.) every 48 hrs. On day 25, mice were sacrificed, lungs were harvested, formalin fixed and H&E stained for the analysis of tumor areas. The values shown are the mean tumor area of each group.** indicates p value<0.01.

Cells were analyzed by flow cytometry. Non-irradiated cells and human Ig (HIg) were used as controls.

Figure 30:
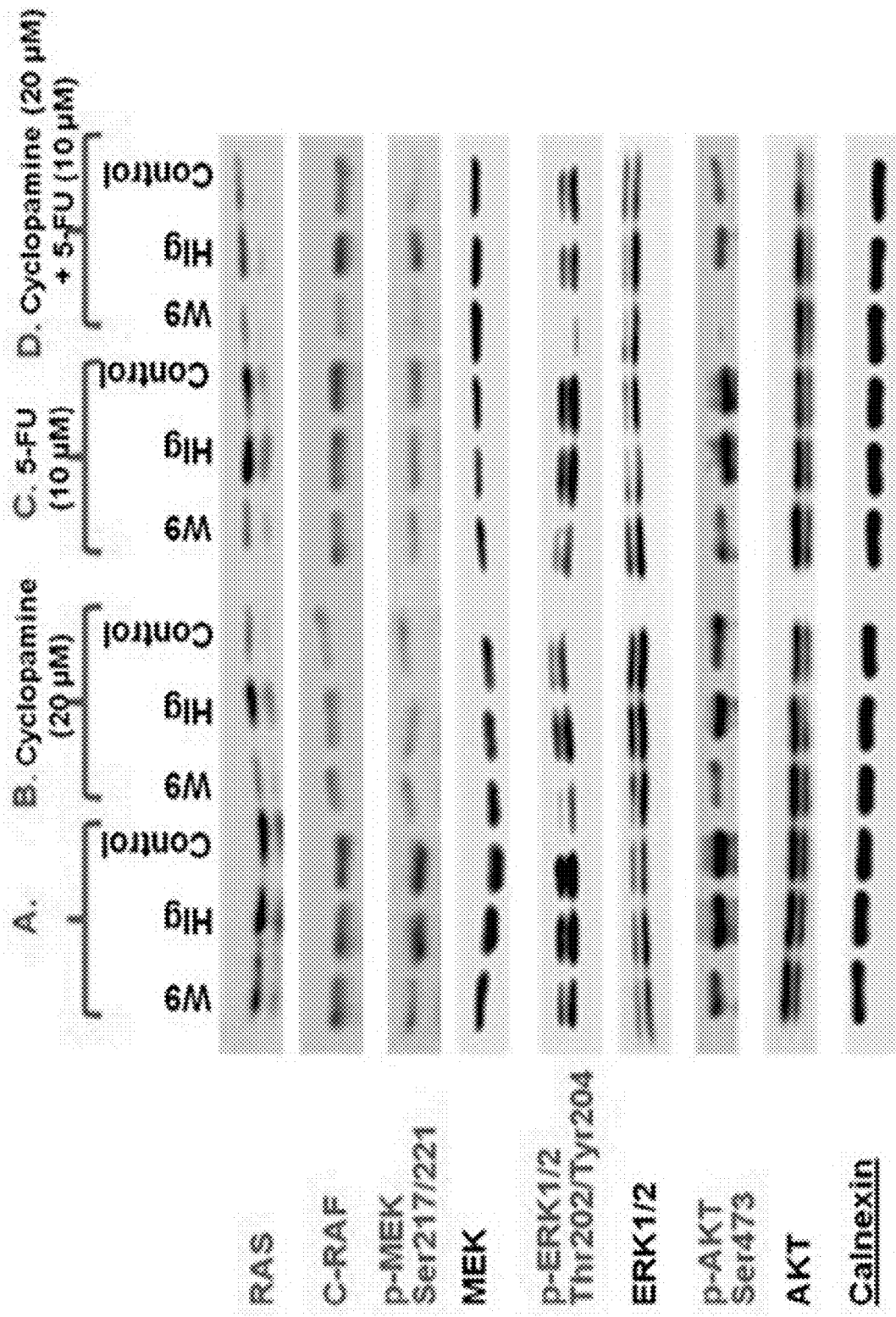

FIG. 30. Inhibition by mAb W9 in combination with 5-FU and cyclopamine of signaling pathways in human pancreatic adenocarcinoma MIAPaCa-2 cells. Human pancreatic adenocarcinoma MIA PaCa-2 cells were incubated with the mAb W9, cyclopamine (20 µM) and 5-FU (10 µM) for 2 days at 37° C. (panel D). Cell lysate were then prepared and tested in western blot with anti-RAS, C-Raf, phosphorylated (p)-MEK (Ser217/221), MEK, pERK(Thr202/Tyr204), ERK, p-AKT (Ser473), AKT mAbs. Calnexin was used as the loading control. Cells incubated with mAb W9 alone (panel A), with mAb W9 and cyclopamine (panel B), and with mAb W9 and 5 FU (panel C) were used as controls.

Figure 31:
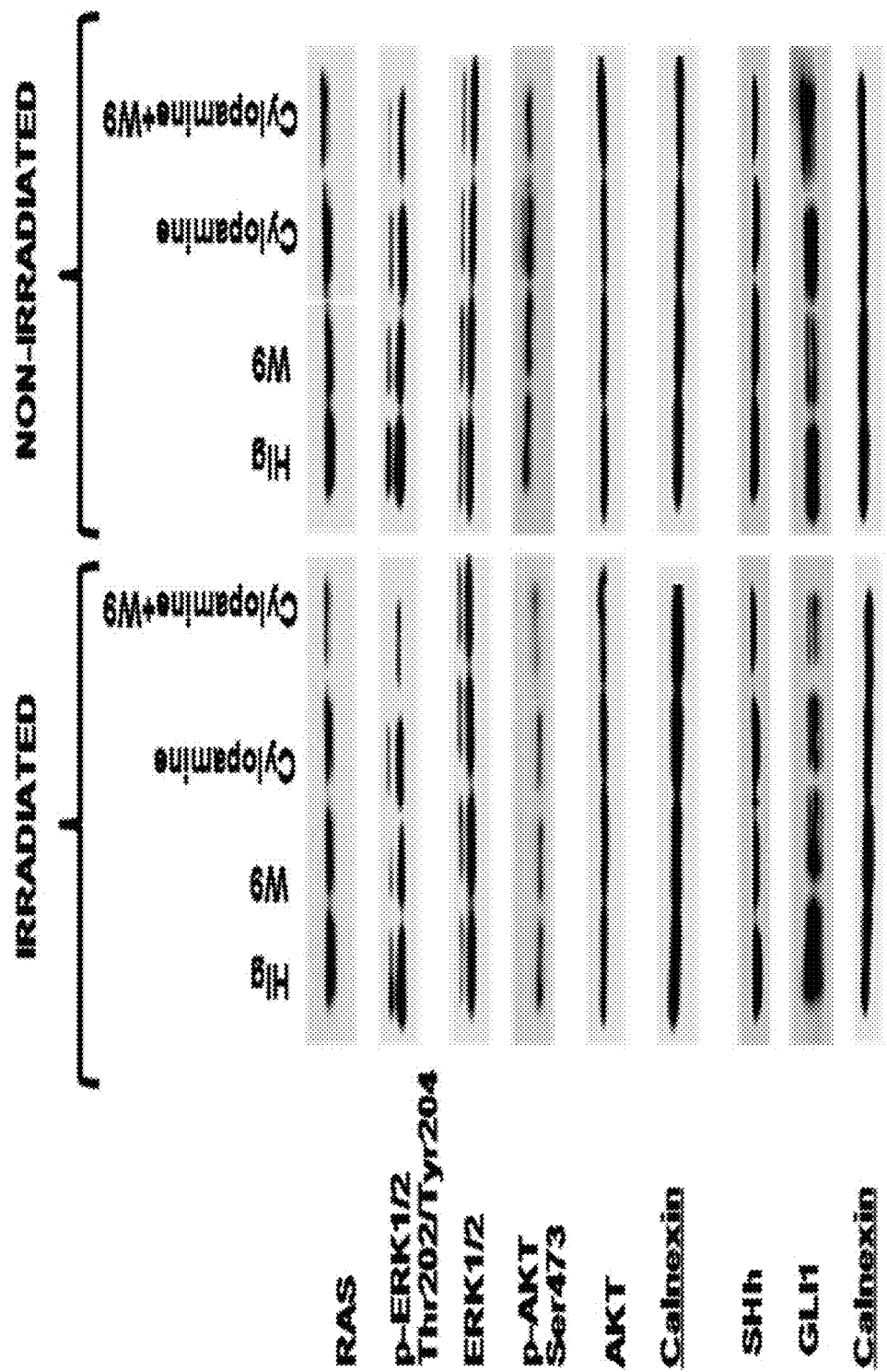

FIG. 31. Inhibition by mAb W9 in combination with radiation and cyclopamine of signaling pathways in human pancreatic adenocarcinoma MIAPaCa-2 cells. Human pancreatic adenocarcinoma MIAPaCa-2 cells were irradiated at the dose of 20Gy and incubated with mAb W9 (10 µg/ml) and cyclopamine (20 µM) for 48 hrs at 37° C. Cell lysates were then prepared and tested by western blot with anti-RAS, phosphorylated (p)-ERK(Thr202/Tyr204), ERK, p-AKT (Ser473), AKT, SHh, GLI1 mAbs. Calnexin was used as the loading control Calnexin and β-actin were used as the loading control.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [8123-85229-29_Sequence-_Listing.txt, Jan. 12, 2018, 19.5 KB], which is incorporated by reference herein.

SEQ ID NO: 1 is the amino acid sequence of the heavy chain of an antibody that specifically binds endoplasmin SEQ ID NO: 2 is the amino acid sequence of the light chain of an antibody that specifically binds endoplasmin SEQ ID NO: 3 is a nucleic acid sequence encoding the heavy chain of an antibody that specifically binds endoplasmin.

SEQ ID NO: 4 is a nucleic acid sequence of the light chain of an antibody that specifically binds endoplasmin SEQ ID NO: 5 is an amino acid sequence of a human endoplasmin.

SEQ ID NO: 6 is a nucleic acid sequence encoding human endoplasmin.

SEQ ID NOs: 7 and 8 are amino acid sequences of endoplasmin polypeptides.

DETAILED DESCRIPTION

I. Abbreviations

5-FU: Fluorouracil
ADCC: antibody-dependent cell-mediated cytotoxicity
Ag: antigen
ALDH$^{bright}$: Aldehyde Dehydrogenase (bright)
Annexin V: Annexin A5
β-catenin: cadherin-associated protein
B-Raf: Serine/threonine-protein kinase B-Raf
CDC: complement-directed cytotoxicity
CDR: complementarity determining region
C-Raf: RAF proto-oncogene serine/threonine-protein kinase
DEAB: 4-(diethylamino)benzaldehyde
DMEM: Dulbecco's modified Eagle's medium
ER: endoplasmic reticulum
ERK1/2: extracellular signal-regulated kinase1/2
FAK: focal adhesion kinase
FBS: fetal bovine serum
FR: framework region
GLI1: Glioma-associated oncogene homolog 1
Grp: Glucose-regulated protein
Gy: Gray
HRP: horse radish peroxidase
Ig: immunoglobulin
mAb: monoclonal antibody
MEK: Mitogen-activated protein kinase kinase
Met: c-Met
O.D.: optical density
PBS: phosphate buffered saline
p-ERK1/2: phosphorylated extracellular signal-regulated kinase1/2
p-FAK: phosphoryalted focal adhesion kinase
PI: Propidium iodide
RAS: RAt Sarcoma
scFv: single chain variable regions of both $V_H$ and $V_L$
SHH: Sonic hedgehog homolog
$V_H$: variable heavy chain region
$V_L$: variable light chain region II. Terms Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Antibody: A polypeptide ligand comprising at least a light chain or heavy chain immunoglobulin variable region which specifically recognizes and specifically binds an epitope of an antigen, such as endoplasmin, or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants. Functional fragments (antigen-binding fragments) of antibodies, that specifically bind an antigen, such as endoplamin, are well known in the art, such as Fab fragments, Fab' fragments, F(ab)'$_2$ fragments, single chain Fv proteins ("scFv"), and disulfide stabilized Fv proteins ("dsFv") that specifically bind the target antigen. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997. Functional fragments are also termed "antigen-binding" fragments, since they specifically bind the target antigen, such as human endoplasmin.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined (see, Kabat et al., *Sequences of Proteins of Immunological Interest*, U.S. Department of Health and Human Services, 1991, which is hereby incorporated by reference). The Kabat database is now maintained online and CDR sequences can be determined, for example, see IMGT/V-QUEST programme version: 3.2.18., Mar. 29, 2011, available on the internet and Brochet, X. et al., Nucl. Acids Res. 36, W503-508, 2008). The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds endoplasmin generally will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds endoplasmin.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. An exemplary antigen is endoplasmin. The term "antigen" includes all related antigenic epitopes. "Epitope" or "antigenic determinant" refers to a site on an antigen to which B and/or T cells respond. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least three, and more usually, at least five or eight to ten amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. Specific, non-limiting examples of a tissue specific antigen are a melanoma specific antigen, or a glioma, breast, lung, prostate, renal or bladder specific antigen. A disease-specific antigen is expressed coincidentally with a disease process, such as melanoma or another type of cancer. Specific non-limiting examples of a disease-specific antigen are an antigen whose expression correlates with, or is predictive of, tumor formation, such as melanoma and/or glioma, and/or another type of cancer (for example, endoplasmin). A disease specific antigen may be an antigen recognized by T cells or B cells.

Amplification: Of a nucleic acid molecule (e.g., a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals, including non-human primates. Similarly, the term "subject" includes both human and veterinary subjects.

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. An antibody that "specifically binds" an antigen, such as endoplasmin with a high affinity and does not significantly bind other unrelated antigens.

Breast cancer: A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV).

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In some embodiments, a chemotherapeutic agent is an agent of use in treating breast, melanoma, and/or gliomas. In one embodiment, a chemotherapeutic agent is radioactive compound. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). Combination chemotherapy is the administration of more than one agent to treat cancer, such as the administration of antibodies that specifically bind endoplasmin in combination with a radioactive or chemical compound to a subject.

Chimeric antibody: An antibody that includes sequences derived from two different antibodies, which typically are of different species. Most typically, chimeric antibodies include human and murine antibody domains, generally human constant regions and murine variable regions, murine CDRs and/or murine SDRs.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Chemotherapeutic agent: An agent with therapeutic usefulness in the treatment of diseases characterized by abnormal cell growth (e.g., an anti-neoplastic agent). Such diseases include tumors, neoplasms, and cancer, as well as diseases characterized by hyperplastic growth such as psoriasis. In one embodiment, a chemotherapeutic agent is an agent of use in treating neoplasms such as solid tumors. Chemotherapeutic agents can be protein or non-protein agents, such as small molecule drugs, antibodies, peptides, proteins, and immunomodulators. In one embodiment, a chemotherapeutic agent is a radioactive molecule. One of skill in the art can readily identify a chemotherapeutic agent (for instance, see Slapak and Kufe, *Principles of Cancer Therapy*, Chapter 86 in *Harrison's Principles of Internal Medicine*, 14th edition; Perry et al., *Chemotherapy, Ch. 17* in Abeloff, *Clinical Oncology $2^{nd}$ ed.*, 2000 Churchill Livingstone, Inc; Baltzer L, Berkery R (eds): *Oncology Pocket Guide to Chemotherapy*, 2nd ed. St. Louis, Mosby-Year Book, 1995; Fischer D S, Knobf M F, Durivage H J (eds): *The Cancer Chemotherapy Handbook*, 4th ed. St. Louis, Mosby-Year Book, 1993).

Conservative variants: "Conservative" amino acid substitutions are those substitutions that do not substantially affect or decrease the affinity of an antibody to specifically bind endoplasmin. For example, a human antibody that specifically binds endoplasmin can include at most about 1, at most about 2, at most about 5, and most about 10, or at most about 15 conservative substitutions and specifically bind the original endoplasmin polypeptide. The term conservative variation also includes the use of a substituted amino acid in place of an unsubstituted parent amino acid, provided that antibody specifically binds endoplasmin. Non-conservative substitutions are those that reduce an activity or binding to endoplasmin.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Complementarity determining region (CDR): Amino acid sequences which together define the binding affinity and specificity of the natural Fv region of a native Ig binding site.

The light and heavy chains of an Ig each have three CDRs, designated L-CDR1, L-CDR2, L-CDR3 and H-CDR1, H-CDR2, H-CDR3, respectively.

Contacting: Placement in direct physical association; includes both in solid and liquid form.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant: A polynucleotide encoding an endoplasmin polypeptide that includes a sequence that is degenerate as a result of the genetic code. There are 20 natural amino acids, most of which are specified by more than one codon. Therefore, all degenerate nucleotide sequences are included in this disclosure as long as the amino acid sequence of the endoplasmin polypeptide encoded by the nucleotide sequence is unchanged.

Diagnostic: Identifying the presence or nature of a pathologic condition, such as, but not limited to, melanoma, ovarian cancer, breast cancer or a glioma. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as a cancer or metastasis.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-endoplasmin antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm. Ther.* 28:341-365, 1985). Diagnostic agents or moieties include radioisotopes and other detectable labels. Detectable labels useful for such purposes are also well known in the art, and include radioactive isotopes such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}TC$, $^{111}In$ and $^{125}I$, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least five or eight to ten amino acids in a unique spatial conformation. Methods of determining spatial conformation of epitopes include, for example, x-ray crystallography and 2-dimensional nuclear magnetic resonance. See, e.g., *Epitope Mapping Protocols* in *Methods in Molecular Biology*, Vol. 66, Glenn E. Morris, Ed (1996). An epitope can be glycosylated. Thus, an antibody can specifically bind a glycosylated form (or an unglycosylated form) of a protein.

Endoplasmin: A protein also known as Glucose-regulated protein (Grp) 94 (Grp94), which is the endoplasmic reticulum (ER)-resident member of the heat-shock-protein 90 (Hsp90) family. In vivo, hsp90 and endoplasmin interact with client proteins and function to protect them from ubiquitin-dependent proteasomal degradation. Although the endoplasmin protein is expressed constitutively in all cell types, its expression is up-regulated under various stress conditions including low glucose levels, low extracellular pH, expression of mutated proteins, and viral infections. Heat-shock proteins have a cytoprotective function and modulate apoptosis directly or indirectly.

It has been shown that cell surface expression of endoplasmin is increased in tumor cells, including hepatocellular carcinoma, colorectal carcinoma and lung cancer cells, and that endoplasmin has an anti-apoptotic effect on some tumor cells. Moreover, increased levels of endoplasmin were observed when a chronic hepatitis B virus (HBV) infection progressed to cirrhosis and hepatocellular carcinoma (HCC). Inhibitors of Hsp90 and endoplasmin (such as geldanamycin (GA) and its less toxic derivative 17-AAG) have been investigated for efficacy in cancer treatment.

Exemplary nucleic acids encoding endoplasmin (Grp94) include, but are not limited to: GENBANK® Accession Nos. NM_003299, BC066656 (*Homo sapiens*); NM_011631 (*Mus musculus*); NM_001045763: (*Xenopus* (Silurana) *tropicalis*); NM_214103 (*Sus scrofa*) NM_98210 (*Danio rerio*); NM_001012197 (*Rattus norvegicus*); NM_001134101: *Pongo abelii*; NM_001003327 (*Canis lupus familiaris*) heat shock protein 90 kDa beta (Grp94); NM_204289 (*Gallus gallus*).

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Expressed: Translation of a nucleic acid into a protein. Proteins may be expressed and remain intracellular, become a component of the cell surface membrane, or be secreted into the extracellular matrix or medium.

Framework region: Amino acid sequences interposed between CDRs. Framework regions include variable light and variable heavy framework regions. The framework regions serve to hold the CDRs in an appropriate orientation for antigen binding.

Glioma: A tumor composed of neuroglia in any developmental state. Gliomas include all intrinsic neoplasms of the brain and spinal cord, such as astrocytomas, ependymomas, and oligodendrogliomas. "Low-grade" gliomas are well-differentiated (not anaplastic); these are benign and portend a better prognosis for the patient. "High-grade" gliomas are undifferentiated or anaplastic; these are malignant and carry a worse prognosis.

Glycosylation: The covalent attachment of a carbohydrate to a protein, such as an antigen. Glycosylation includes N-linked glycosylation, O-linked glycosylation and C-linked glycosylation.

HAMA (human anti-murine antibody) response: An immune response in a human subject to the variable and constant regions of a murine antibody that has been administered to the patient. Repeated antibody administration may lead to an increased rate of clearance of the antibody from the patient's serum and may also elicit allergic reactions in the patient.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunoconjugate: A covalent linkage of an effector molecule to an antibody or functional fragment thereof that specifically binds an antigen of interest, such as human endoplasm. The effector molecule can be a detectable label, an immunotoxin, a cytokine or a chemokine. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule. In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule.

Immunogenic peptide: A peptide which comprises an allele-specific motif or other sequence, such as an N-terminal repeat, such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide. In one specific non-limiting example, an immunogenic polypeptide includes a region of endoplasmin, or a fragment thereof, wherein the polypeptide that is expressed on the cell surface of a host cell that expresses the full-length endoplasmin polypeptide.

Immunogenic composition: A composition comprising a polypeptide, such as an endoplasmin polypeptide, that induces a measurable CTL response against cells expressing endoplasmin polypeptide, or induces a measurable B cell response (such as production of antibodies) against an endoplasmin polypeptide. An immunogenic composition can also induce cytokine production. It further refers to isolated nucleic acids encoding an endoplasmin polypeptide that can be used to express the endoplasmin polypeptide (and thus be used to elicit an immune response against this polypeptide). For in vitro use, an immunogenic composition may consist of the isolated protein or peptide epitope. For in vivo use, the immunogenic composition will typically comprise the protein or immunogenic peptide in pharmaceutically acceptable carriers, and/or other agents. Any particular peptide, such as an endoplasmin polypeptide, or nucleic acid encoding the polypeptide, can be readily tested for its ability to induce a CTL or B cell response by art-recognized assays Immunogenic compositions can include adjuvants, which are well known to one of skill in the art.

Immunologically reactive conditions: Includes reference to conditions which allow an antibody raised against a particular epitope to bind to that epitope to a detectably greater degree than, and/or to the substantial exclusion of, binding to substantially all other epitopes Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (such as temperature, osmolarity, and pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Mammal: This term includes both human and non-human mammals. Similarly, the term "subject" includes both human and veterinary subjects.

Major histocompatibility complex (MHC): Generic designation meant to encompass the histocompatibility antigen systems described in different species, including the human leukocyte antigens ("HLA"). The term "motif" refers to the pattern of residues in a peptide of defined length, usually about 8 to about 11 amino acids, which is recognized by a particular MHC allele. The peptide motifs are typically different for each MHC allele and differ in the pattern of the highly conserved residues and negative binding residues.

Melanoma: A form of cancer that originates in melanocytes (cells that make the pigment melanin). Melanocytes are found primary in the skin, but are also present in the bowel and eye. Melanoma in the skin includes superficial spreading melanoma, nodular melanoma, acral lentiginous melanoma, and lentigo maligna (melanoma). Any of the above types may produce melanin or can be amelanotic. Similarly, any subtype may show desmoplasia (dense fibrous reaction with neurotropism) which is a marker of aggressive behavior and a tendency to local recurrence. Other melanomas include clear cell sarcoma, mucosal melanoma and uveal melanoma.

Features that affect prognosis are tumor thickness in millimeters (Breslow's depth), depth related to skin structures (Clark level), type of melanoma, presence of ulceration, presence of lymphatic/perineural invasion, presence of tumor infiltrating lymphocytes (if present, prognosis is better), location of lesion, presence of satellite lesions, and presence of regional or distant metastasis. When melanomas have spread to the lymph nodes, one of the most important factors is the number of nodes with malignancy. The extent of malignancy within a node is also important; micrometastases in which malignancy is only microscopic have a more favorable prognosis than macrometastases. When there is distant metastasis, the five year survival rate is less than 10 percent; the median survival is 6 to 12 months. Metastases to skin and lungs have a better prognosis. Metastases to brain, bone and liver are associated with a worse prognosis.

Melanoma can be staged as follows:
Stage 0: Melanoma in Situ (Clark Level I), 100% Survival
Stage I/II: Invasive Melanoma, 85-95% Survival
    T1a: Less than 1.00 mm primary, w/o Ulceration, Clark Level II-III
    T1b: Less than 1.00 mm primary, w/Ulceration or Clark Level IV-V
    T2a: 1.00-2.00 mm primary, w/o Ulceration
Stage II: High Risk Melanoma, 40-85% Survival
    T2b: 1.00-2.00 mm primary, w/Ulceration
    T3a: 2.00-4.00 mm primary, w/o Ulceration
    T3b: 2.00-4.00 mm primary, w/Ulceration
    T4a: 4.00 mm or greater primary w/o Ulceration
    T4b: 4.00 mm or greater primary w/Ulceration
Stage III: Regional Metastasis, 25-60% Survival
    N1: Single Positive Lymph Node
    N2: 2-3 Positive Lymph Nodes OR Regional Skin/In-Transit Metastasis
    N3: 4 Positive Lymph Nodes OR Lymph Node and Regional Skin/In Transit Metastases
Stage IV: Distant Metastasis, 9-15% Survival
    M1a: Distant Skin Metastasis, Normal lactate dehydrogenase (LDH)
    M1b: Lung Metastasis, Normal LDH
    M1c: Other Distant Metastasis OR Any Distant Metastasis with Elevated LDH Monoclonal antibody: An antibody produced by a single clone of B-lymphocytes, by a cell into which the light and heavy chain genes of a single antibody have been transfected, or by a specific phage in an antibody library such that the monoclonal antibody includes a defined set of CDRs and specifically binds a target antigen of interest. Monoclonal antibodies are produced by methods known to those of skill in the art, for instance (but not limited to) by making hybrid antibody-forming cells from a fusion of myeloma cells with immune spleen cells or selection from a phage display library of antibody sequences. Monoclonal antibodies include humanized and fully human monoclonal antibodies. As used herein, a functional fragment of a monoclonal antibody includes antibody fragments that specifically bind the target protein (antigen-binding) for the monoclonal antibody, such as, but not limited to scFv, Fv, dsRv, or Fab. Monoclonal antibodies specifically bind an antigenic epitope, such as a glycosylated epitope. Monoclonal antibodies include bi-functional antibodies wherein one or more sets of CDRs specifically binds a target antigen, such as endoplasmin, and effector function enhanced Fc and other glycol-engineered antibodies.

Neoplasia, malignancy, cancer or tumor: The result of abnormal and uncontrolled growth of cells. Neoplasia, malignancy, cancer and tumor are often used interchangeably. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In several examples, a tumor is melanoma, breast cancer, renal cancer, glioma or a squamous cell carcinoma, such as head and neck cancer.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information website. The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Oligonucleotide: A linear polynucleotide sequence of up to about 100 nucleotide bases in length.

Open reading frame (ORF): A series of nucleotide triplets (codons) coding for amino acids without any termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter, such as a heterologous promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (such as glycosylation or phosphorylation). In one embodiment, the polypeptide is endoplasmin polypeptide. A "residue" refers to an amino acid or amino acid mimetic incorporated in a polypeptide by an amide bond or amide bond mimetic. A polypeptide has an amino terminal (N-terminal) end and a carboxy terminal (C-terminal) end.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a deacrease in the number of size of metastases. "Ameliorating" refers to the reduction in the number or severity of signs or symptoms of a disease, such as cancer.

Probes and primers: A probe comprises an isolated nucleic acid attached to a detectable label or reporter molecule. Primers are short nucleic acids, preferably DNA oligonucleotides, 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers can be selected that comprise 20, 25, 30, 35, 40, 50 or more consecutive nucleotides.

Promoter: A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancers or repressor elements which can be located as much as several thousand base pairs from the start site of transcription. Both constitutive and inducible promoters are included (see e.g., Bitter et al., *Methods in Enzymology* 153:516-544, 1987).

Specific, non-limiting examples of promoters include promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells Purified: The term purified does not require absolute purity; rather, it is intended as a relative term. Thus, for example, a purified nucleic acid is one in which the nucleic acid is more enriched than the nucleic acid in its natural environment within a cell. Similarly, a purified peptide preparation is one in which the peptide or protein is more enriched than the peptide or protein is in its natural environment within a cell. Substantial purification denotes purification from other proteins or cellular components. In one embodiment, a preparation is purified (or isolated) such that the protein or peptide represents at least 50% (such as, but not limited to, 70%, 80%, 90%, 95%, 98% or 99%) of the total peptide or protein content of the preparation. The endoplasmin polypeptides disclosed herein can be purified (and/or synthesized) by any of the means known in the art (see, e.g., *Guide to Protein Purification*, ed. Deutscher, *Meth. Enzymol.* 185, Academic Press, San Diego, 1990; and Scopes, *Protein Purification: Principles and Practice*, Springer Verlag, N.Y., 1982).

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Recombinant toxins: Chimeric proteins in which a cell targeting moiety is fused to a toxin (Pastan et al., *Science*, 254:1173-1177, 1991). If the cell targeting moiety is the Fv portion of an antibody, the molecule is termed a recombinant immunotoxin (Chaudhary et al., *Nature*, 339:394-397, 1989). The toxin moiety is genetically altered so that it cannot bind to the toxin receptor present on most normal cells. Recombinant immunotoxins selectively kill cells which are recognized by the antigen binding domain. These recombinant toxins and immunotoxins can be used to treat cancer, for example, a cancer in which endoplasmin is expressed.

Selectively hybridize: Hybridization under moderately or highly stringent conditions that excludes non-related nucleotide sequences.

In nucleic acid hybridization reactions, the conditions used to achieve a particular level of stringency, will vary depending on the nature of the nucleic acids being hybridized. For example, the length, degree of complementarity, nucleotide sequence composition (e.g., GC v. AT content), and nucleic acid type (e.g., RNA versus DNA) of the hybridizing regions of the nucleic acids can be considered in selecting hybridization conditions. An additional consideration is whether one of the nucleic acids is immobilized, for example, on a filter.

A specific, non-limiting example of progressively higher stringency conditions is as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual*, 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologues or variants of an endoplasmin polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of an endoplasmin polypeptide are typically characterized by possession of at least 75%, for example at least 80%, sequence identity counted over the full length alignment with the amino acid sequence of endoplasmin using the NCBI Blast 2.0, gapped blastp set to default parameters. For comparisons of amino acid sequences of greater than about 30 amino acids, the Blast 2 sequences function is employed using the default BLOSUM62 matrix set to default parameters (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95%, depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus an endoplasmin specific binding agent is an agent that binds substantially to an endoplasmin polypeptide. In one embodiment, the specific binding agent is a monoclonal or polyclonal antibody that specifically binds endoplasmin.

Squamous cell carcinoma: A type of cancer that originates in squamous cells, thin, flat cells that form the surface of the skin, eyes, various internal organs, and the lining of hollow organs and ducts of some glands. Squamous cell carcinoma is also referred to as epidermoid carcinoma. One type of squamous cell carcinoma is head and neck head squamous cell carcinoma (HNSCC). Head and neck squamous cell carcinoma includes cancers of the nasal cavity, sinuses, lips, mouth, salivary glands, throat and larynx.

HNSCC can be staged as follows:
- Stage 0: No evidence of tumor.
- Stage I: Tumor is 2 cm or less in greatest dimension; no evidence of regional lymph node involvement or distant metastasis.
- Stage II: Tumor is more than 2 cm, but no larger than 4 cm; no evidence of regional lymph node involvement or distant metastasis.
- Stage III: Tumor is larger than 4 cm; in some cases, the tumor has spread to the lymph nodes; no evidence of distant metastasis.
- Stage IV: Tumor has spread to the lymph nodes; in some cases, distant metastases are present.

Subject: Living multi-cellular vertebrate organisms, a category that includes both human and veterinary subjects, including human and non-human mammals.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, often called "helper" T cells, help orchestrate the immune response, including antibody responses as well as killer T cell responses. $CD8^+$ T cells carry the "cluster of differentiation 8" (CD8) marker. In one embodiment, a CD8 T cell is a cytotoxic T lymphocytes. In another embodiment, a CD8 cell is a suppressor T cell.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate a tumor or decrease the number or size of metastases. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Human Monoclonal Antibodies that Specifically Bind Endoplasmin

Antibodies have been produced that specifically bind endoplasmin (Grp94), including monoclonal antibodies, such as fully human monoclonal antibodies. These antibodies and/or antigen-biding fragments thereof can be used to isolate endoplasmin, and can be used to detect and/or treat tumors that express endoplasmin, such as, but not limited to, melanoma, breast cancer, head and neck squamous cell carcinoma, renal cancer, lung cancer, glioma, bladder cancer or pancreatic cancer. These antibodies can be conjugated to detectable labels or effector molecules.

In one embodiment, the antibodies specifically bind glycosylated endoplasmin Thus, in this embodiment, the antibodies do not specifically bind un-glycosylated endoplasmin or unrelated antigens.

Disclosed herein are human monoclonal antibodies and antigen-biding fragments thereof that specifically bind endoplasmin. In one example, human endoplasmin has an amino acid sequence set forth as:

MRALWVLGLCCVLLTFGSVRADDEVDVDGTVEEDLGKSREGSRTD

DEVVQREEEAIQLDGLNASQIRELREKSEKFAFQAEVNRMMKLIINSLYK

NKEIFLRELISNASDALDKIRLISLTDENALSGNEELTVKIKCDKEKNLL

HVTDTGVGMTREELVKNLGTIAKSGTSEFLNKMTEAQEDGQSTSELIGQF

GVGFYSAFLVADKVIVTSKHNNDTQHIWESDSNEFSVIADPRGNTLGRGT

TITLVLKEEASDYLELDTIKNLVKKYSQFINFPIYVWSSKTETVEEPMEE

EEAAKEEKEESDDEAAVEEEEEEKKPKTKKVEKTVWDWELMNDIKPIWQR

PSKEVEEDEYKAFYKSFSKESDDPMAYIHFTAEGEVTFKSILFVPTSAPR

GLFDEYGSKKSDYIKLYVRRVFITDDFHDMMPKYLNFVKGVVDSDDLPLN

VSRETLQQHKLLKVIRKKLVRKTLDMIKKIADDKYNDTFWKEFGTNIKLG

VIEDHSNRTRLAKLLRFQSSHHPTDITSLDQYVERMKEKQDKIYFMAGSS

RKEAESSPFVERLLKKGYEVIYLTEPVDEYCIQALPEFDGKRFQNVAKEG

VKFDESEKTKESREAVEKEFEPLLNWMKDKALKDKIEKAVVSQRLTESPC

ALVASQYGWSGNMERIMKAQAYQTGKDISTNYYASQKKTFEINPRHPLIR

DMLRRIKEDEDDKTVLDLAVVLFETATLRSGYLLPDTKAYGDRIERMLRL

SLNIDPDAKVEEEPEEEPEETAEDTTEDTEQDEDEEMDVGTDEEEETAKE

STAEKDEL

SEQ ID NO: 5, See also GENBANK® Accession No. NM_003299, as available on Jun. 16, 2010 incorporated herein by reference).

In another example, the Endoplasmin is encoded by the nucleic acid sequence set forth as:

gtgggcggac cgcgcggctg gaggtgtgag gatccgaacc caggggtggg gggtggaggc ggctcctgcg atcgaagggg acttgagact caccggccgc acgccatgag ggccctgtgg gtgctgggcc tctgctgcgt cctgctgacc ttcgggtcgg tcagagctga cgatgaagtt gatgtggatg gtacagtaga agaggatctg ggtaaaagta gagaaggatc aaggacggat gatgaagtag tacagagaga ggaagaagct attcagttgg atggattaaa tgcatcacaa ataagagaac ttagagagaa gtcggaaaag tttgccttcc aagccgaagt taacagaatg atgaaactta tcatcaattc atttgtataa aataaagaga ttttcctgag agaactgatt tcaaatgctt ctgatgcttt agataagata aggctaatat cactgactga tgaaaatgct ctttctggaa atgaggaact aacagtcaaa attaagtgtg -continued

```
ataaggagaa gaacctgctg catgtcacag acaccggtgt aggaatgacc agagaagagt tggttaaaaa ccttggtacc atagccaaat ctgggacaag cgagttttta aacaaaatga ctgaagcaca ggaagatggc cagtcaactt ctgaattgat tggccagttt ggtgtcggtt tctattccgc cttccttgta gcagataagg ttattgtcac ttcaaaacac aacaacgata cccagcacat ctgggagtct gactccaatg aattttctgt aattgctgac ccaagaggaa acactctagg acggggaacg acaattaccc ttgtcttaaa agaagaagca tctgattacc ttgaattgga tacaattaaa aatctcgtca aaaaatattc acagttcata aactttccta tttatgtatg gagcagcaag actgaaactg ttgaggagcc catggaggaa gaagaagcag ccaaagaaga gaaagaagaa tctgatgatg aagctgcagt agaggaagaa gaagaagaaa agaaaccaaa gactaaaaaa gttgaaaaaa ctgtctggga ctgggaactt atgaatgata tcaaaccaat atggcagaga ccatcaaaag aagtagaaga agatgaatac aaagctttct acaaatcatt ttcaaaggaa agtgatgacc ccatggctta tttttcacat actgctgaag gggaagttac cttcaaatca attttatttg tacccacatc tgctccacgt ggtctgtttg acgaatatgg atctaaaaag agcgattaca ttaagctcta tgtgcgccgt gtattcatca cagacgactt ccatgatatg atgcctaaat acctcaattt tgtcaagggt gtggtggact cagatgatct ccccttgaat gtttcccgcg agactcttca gcaacataaa ctgcttaagg tgattaggaa gaagcttgtt cgtaaaacgc tggacatgat caagaagatt gctgatgata aatacaatga tacttttttgg aaagaatttg gtaccaacat caagcttggt gtgattgaag accactcgaa tcgaacacgt cttgctaaac ttcttaggtt ccagtcttct catcatccaa ctgacattac tagcctagac cagtatgtgg aaagaatgaa ggaaaaacaa gacaaaatct acttcatggc tgggtccagc agaaaagagg ctgaatcttc tccatttgtt gagcgacttc tgaaaaaggg ctatgaagtt atttacctca cagaacctgt ggatgaatac tgtattcagg cccttcccga atttgatggg aagaggttcc agaatgttgc caaggaagga gtgaagttcg atgaaagtga gaaaactaag gagagtcgtg aagcagttga gaaagaattt gagcctctgc tgaattggat gaaagataaa gcccttaagg acaagattga aaaggctgtg gtgtctcagc gcctgacaga atctccgtgt gctttggtgg ccagccagta cggatggtct ggcaacatgg agagaatcat gaaagcacaa gcgtaccaaa cgggcaagga catctctaca aattactatg cgagtcagaa gaaaacattt gaaattaatc ccagacaccc gctgatcaga gacatgcttc gacgaattaa ggaagatgaa gatgataaaa cagttttgga tcttgctgtg gttttgtttg aaacagcaac gcttcggtca gggtatcttt taccagacac taaagcatat ggagatagaa tagaaagaat gcttcgcctc agtttgaaca ttgaccctga tgcaaaggtg gaagaagagc ccgaagaaga acctgaagag acagcagaag acacaacaga agacacagag caagacgaag atgaagaaat ggatgtggga acagatgaag aagaagaaac agcaaaggaa tctacagctg aaaaagatga attgtaaatt atactctcac catttggatc ctgtgtggag agggaatgtg aaatttacat catttctttt tgggagagac ttgttttgga tgccccctaa tccccttctc ccctgcactg taaaatgtgg gattatgggt cacaggaaaa agtgggtttt ttagttgaat ttttttttaac attcctcatg aatgtaaatt tgtactattt aactgactat tcttgatgta aaatcttgtc atgtgtataa aaataaaaaa gatcccaaat
```

SEQ ID NO: 6, see also GENBANK® Accession No. NM_003299, Jun. 16, 2010, incorporated herein by reference herein.

Once of skill in the art can readily use a nucleic acid sequence to produce a polypeptide, such as endoplasmin using standard method in molecular biology (see, for example, *Molecular Cloning: A Laboratory Manual*, 2nd ed., vol. 1-3, ed. Sambrook et al., Cold Spring Harbor Laboratory Press, Cold Spring Harbor, N.Y., 1989). With the therapeutic agents and antibodies described herein, one of skill in the art can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

Described herein are isolated human monoclonal antibodies and fragments thereof that specifically bind human endoplasmin, such as glycosylated endoplasmin. In some embodiments, the human monoclonal antibody antigen-binding fragment is a scFv. Also described are compositions including the provided human monoclonal antibodies or functional fragment thereof (that specifically bind human endoplasmin) and a pharmaceutically acceptable carrier. Nucleic acids encoding these antibodies, expression vectors comprising these nucleic acids, and isolated host cells that express the nucleic acids are also provided.

Also described herein are immunoconjugates comprising the human monoclonal antibodies or antigen-binding fragment thereof that specifically binds human endoplasmin. The immunoconjugates can comprise any therapeutic agent, toxin or other moiety. In one example, the toxin is PE or a variant or fragment thereof. Compositions comprising the immunoconjugates are also described.

Compositions comprising the human monoclonal antibodies that specifically bind endoplasmin or antigen-binding fragment thereof can be used for screening, research, detection and therapeutic purposes. For example, the human monoclonal antibodies or antigen-binding fragment thereof can be used to identify other antibodies that specifically bind endoplasmin, such as in competitive immunoassays.

Compositions comprising the human monoclonal antibodies that specifically bind endoplasmin or an antigen-binding fragment thereof can be used to treat a subject diagnosed with cancer, such as a cancer that exhibits increased expression of endoplasmin relative to normal cells. For example, the antibodies can be used to treat melanoma, breast cancer, head and neck squamous cell carcinoma, renal cancer, lung cancer, glioma, bladder cancer, ovarian cancer or pancreatic cancer. Melanoma includes spreading melanoma, nodular melanoma, acral lentiginous melanoma, and lentigo maligna (melanoma). Squamous cells carcinomas include, but are not limited to head and neck squamous cell carcinoma, and squamous cell cancers of the lung.

Compositions comprising the endoplasmin antibodies can also be used to prevent metastasis or decrease the number of micrometastases, such as micrometastases to regional lymph nodes. Immunoconjugates comprising the endoplasmin antibodies also can be used to treat a patient diagnosed with cancer. The human monoclonal antibodies can also be used to diagnose cancer in a subject, including the detection of a metastasis. For example, the human monoclonal antibodies can be contacted with a sample from the patient, such as a serum sample, to detect elevated levels of endoplasmin. The antibodies and compositions provided herein can also be used to detect cancer in a subject or to confirm the diagnosis of cancer in a patient.

Disclosed herein are fully human monoclonal antibodies that specifically bind human endoplasmin and functional fragments thereof (antigen-binding fragments) that specifically bind endoplasmin. A major limitation in the clinical use of mouse monoclonal antibodies is the development of a human anti-murine antibody (HAMA) response in the patients receiving the treatments. The HAMA response can involve allergic reactions and an increased rate of clearance of the administered antibody from the serum. Various types of modified monoclonal antibodies have been developed to minimize the HAMA response while trying to maintain the antigen binding affinity of the parent monoclonal antibody. One type of modified monoclonal antibody is a human-mouse chimera in which a murine antigen-binding variable region is coupled to a human constant domain (Morrison and Schlom, *Important Advances in Oncology*, Rosenberg, S. A. (Ed.), 1989). A second type of modified monoclonal antibody is the complementarity determining region (CDR)-grafted, or humanized, monoclonal antibody (Winter and Harris, *Immunol. Today* 14:243-246, 1993). However, the antibodies disclosed herein are fully human; both the framework region and the CDRs are derived from human sequences. Thus, a HAMA is not induced when these antibodies are administered to a human subject.

In some embodiments, the human monoclonal antibody or antigen-binding fragment thereof comprises at least a portion of the variable chain of the heavy chain amino acid sequence set forth as SEQ ID NO: 1 and specifically binds endoplasmin. For example, the human monoclonal antibody can include the SDRs (specificity determining residues, the CDRs, or the variable region. In the amino acid sequence shown below, the constant region is in bold, and the CDRs are underlined:

```
                                              (SEQ ID NO: 1)
QVQLVQSGAEVKKPGASVKVSCKAS...........MHW

VRQAPGQRLEWMGW...............KYSQKFQGRVTITR

DTSASTAYMELSSLRSEDTAVYYC.........WGQGTL

VTVSASTKGPSVFPLAPSSKSTSGGTAALGCLVKDYF

PEPVTVSWNSGALTSGVHTFPAVLQSSGLYSLSSVVT

VPSSSLGTQTYICNVNHKPSNTKVDKKVEPKSCDKT

HTCPPCPAPELLGGPSVFLFPPKPKDTLMISRTPEVT

CVVVDVSHEDPEVKFNWYVDGVEVHNAKTKPREEQ

YNSTYRVVSVLTVLHQDWLNGKEYKCKVSNKALPA

PIEKTISKAKGQPREPQVYTLPPSREEMTKNQVSLT

CLVKGFYPSDIAVEWESNGQPENNYKTTPPVLDSDG

SFFLYSKLTVDKSRWQQGNVFSCSVMetHEALHNHYT

QKSLSLSPGK
```

In some embodiments, the human monoclonal antibody, or antigen-binding fragment thereof, comprises at least a portion of the heavy chain amino acid sequence set forth as SEQ ID NO: 1 and specifically binds endoplasmin. In some examples, at least one of the CDRs of the light chain of the antibody comprises one or more of the amino acid sequences set forth as amino acids 26-33 of SEQ ID NO: 1 (CDR1), amino acids 51-58 of SEQ ID NO: 1 (CDR2), and amino acids 97-103 of SEQ ID NO: 1 (CDR3). In additional examples, the heavy chain of the antibody comprises the amino acid sequence set forth as amino acids 26-33 of SEQ ID NO: 1 (CDR1), amino acids 51-58 of SEQ ID NO: 1 (CDR2), and amino acids 97-103 of SEQ ID NO: 1 (CDR3). In some examples, the variable region of the heavy chain of the antibody can include, or consist of, amino acids 1-113 of SEQ ID NO: 1. The heavy chain of the antibody can include, or consist of, SEQ ID NO: 1.

In some embodiments, the human monoclonal antibody, or antigen-binding fragment thereof, comprises at least a portion of the variable region of the light chain amino acid sequence set forth as SEQ ID NO: 2 and specifically binds endoplasmin. In the amino acid sequence shown below, the constant region is in bold, and the CDRs are underlined:

```
                                              (SEQ ID NO: 2)
EIELTQSPSSLSASVGDRVTITCRASQ.........LNWYQQK

PGKAPKLLIY......SLQSGVPSRFSGSGSGTDFTLTISSL

QPEDFATYYC...........FGQGTKVEIKTVAAPSVFI

FPPSDEQLKSGTASVVCLLNNFYPREAKVQWKVDNA

LQSGNSQESVTEQDSKDSTYSLSSTLTLSKADYEKH

KVYACEVTHQGLSSPVTKSFNRGEC
```

In some examples, at least one of the CDRs of the light chain of the antibody comprises one or more of the amino acid sequences set forth as amino acids 27-32 of SEQ ID NO: 2 (CDR1), amino acids 50-52 of SEQ ID NO: 2 (CDR2), and amino acids 89-97 of SEQ ID NO: 2 (CDR3). In additional examples, the light chain of the antibody comprises amino acids amino acids 27-32 of SEQ ID NO: 2 (CDR1), amino acids 50-52 of SEQ ID NO: 2 (CDR2), and amino acids 89-97 of SEQ ID NO: 2 (CDR3). The variable region of the light chain of the antibody can include, or consist of, amino acids 1-107 of SEQ ID NO: 2. The light chain of the antibody can include, or consist of, SEQ ID NO: 2.

In some embodiments, the human monoclonal antibody is labeled. In some examples, the label is a fluorescence, enzymatic, or radioactive label.

The monoclonal antibody can be of any isotype. The monoclonal antibody can be, for example, an IgA, IgM or an IgG antibody, such as $IgG_1$ or an IgG2. The class of an antibody that specifically binds endoplasmin can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds endoplasmin that was originally IgM may be class switched to an IgG. Class switching can be used to convert one IgG subclass to another, such as from $IgG_1$ to $IgG_2$.

Fully human monoclonal antibodies include human framework regions. The human framework regions can include the framework regions disclosed in one or both of SEQ ID NO: 1 or SEQ ID NO: 2 (these sequences include CDR sequences as well as framework sequences). However, the framework regions can be from another source. Additional examples of framework sequences that can be used include the amino acid framework sequences of the heavy and light chains disclosed in PCT Publication No. WO 2006/074071 (see, for example, SEQ ID NOs: 1-16), which is herein incorporated by reference.

Antibody fragments are encompassed by the present disclosure, such as Fab, F(ab')$_2$, scFv and Fv which include a heavy chain and light chain variable region and bind the epitopic determinant on endoplasmin. These antibody fragments retain the ability to specifically bind with the antigen, namely human endoplasmin, and thus are antigen-binding fragments. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

(6) A dimer of a single chain antibody (scFV$_2$), defined as a dimer of a scFV. This has also been termed a "miniantibody."

Methods of making these fragments are known in the art (see for example, Harlow and Lane, *Antibodies: A Laboratory Manual*, Cold Spring Harbor Laboratory, New York, 1988).

In a further group of embodiments, the antibodies are Fv antibodies, which are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra). Dimers of a single chain antibody (scFV$_2$), are also contemplated.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced that specifically bind human endoplasmin Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

IV. Use in Therapeutic and Diagnostic Moieties

The human monoclonal antibodies, or functional fragments thereof that specifically bind human endoplasmin can be used in therapeutic and diagnostic methods, such as for the treatment and detection of melanoma, breast cancer, head and neck squamous cell carcinoma, renal cancer, lung cancer, glioma, bladder cancer, ovarian cancer or pancreatic cancer. For therapeutic use, the methods can include administering to subject a therapeutically effective amount of an antibody that specifically binds endoplasmin, or an antigen-binding fragment thereof, such as for the treatment of melanoma, breast cancer, head and neck squamous cell carcinoma, renal cancer, lung cancer, glioma, bladder cancer, ovarian cancer or pancreatic cancer, such as pancreatic adenocarcinoma.

In several embodiments, the human monoclonal antibodies or antigen-binding fragments thereof described herein can be conjugated to a therapeutic agent. Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified Pseudomonas exotoxin or Diphtheria toxin, encapsulating agents (such as liposomes) which themselves contain pharmacological compositions, radioactive agents such as $^{125}I$, $^{32}P$, $^{14}C$, $^{3}H$ and $^{35}S$ and other labels, target moieties and ligands.

Toxins can be employed with the endoplasmin-specific human monoclonal antibodies, and antigen-binding fragments thereof, that are described herein, to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is Pseudomonas exotoxin (PE) (U.S. Pat. No. 5,602,095). As used herein "Pseudomonas exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989). In one embodiment, the cytotoxic fragment of PE retains at least 50%, at least 75%, at least 90%, or at least 95% of the cytotoxicity of native PE. In some examples, the cytotoxic fragment is more toxic than native PE.

Native *Pseudomonas* exotoxin A (PE) is an extremely active monomeric protein (molecular weight 66 kD), secreted by *Pseudomonas aeruginosa*, which inhibits protein synthesis in eukaryotic cells. The method of PE action is inactivation of the ADP-ribosylation of elongation factor 2 (EF-2). The exotoxin contains three structural domains that act in concert to cause cytotoxicity. Domain la mediates cell binding. Domain II is responsible for translocation into the cytosol and domain III mediates ADP ribosylation of elongation factor 2. The function of domain Ib is unknown. PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; PCT Publication No. WO 99/51643; Pai et al., *Proc. Natl Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997, each of which is herein incorporated by reference.

The antibodies and antigen-binding fragments thereof described herein can also be used to target any number of different diagnostic or therapeutic compounds to cells expressing endoplasmin on their surface. Thus, an antibody of the present disclosure can be attached directly or via a linker to a drug that is to be delivered directly to cells expressing cell-surface endoplasmin. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-endoplasmin antibody can be an encapsulation system, such as a liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

The antibodies disclosed herein can be conjugated to an additional therapeutic agent and/or can be used in conjunction with an addition agent, using sequential or simultaneous administration. The choice of a particular therapeutic agent depends on the particular target molecule or cell, and the desired biological effect. Thus, for example, the therapeutic agent can be a cytotoxin that is used to bring about the death of a particular target cell. Conversely, where it is desired to invoke a non-lethal biological response, the therapeutic agent can be conjugated to a non-lethal pharmacological agent or a liposome containing a non-lethal pharmacological agent.

The therapeutic agent can also be a cytokine or a chemokine. A "cytokine" is class of proteins or peptides released by one cell population which act on another cell as intercellular mediators. Cytokines can act as an immune-modulating agent. Examples of cytokines include lymphokines, monokines, growth factors and traditional polypeptide hormones. Thus, embodiments utilize an interferon (e.g., IFN-α, IFN-β, and IFN-γ); tumor necrosis factor super family (TNFSF) member; human growth hormone; thyroxine; insulin; proinsulin; relaxin; prorelaxin; follicle stimulating hormone (FSH); thyroid stimulating hormone (TSH); luteinizing hormone (LH); hepatic growth factor; prostaglandin, fibroblast growth factor; prolactin; placental lactogen, OB protein; TNF-α; TNF-β; integrin; thrombopoietin (TPO); a nerve growth factor such as NGF-β; platelet-growth factor; TGF-α; TGF-β; insulin-like growth factor-I and -II; erythropoietin (EPO); colony stimulating factors (CSFs) such as macrophage-CSF (M-CSF); granulocyte-macrophage-CSF (GM-CSF); and granulocyte-CSF (G-CSF); an interleukin (IL-1 to IL-21), kit-ligand or FLT-3, angiostatin, thrombospondin, or endostatin. These cytokine include proteins from natural sources or from recombinant cell culture and biologically active equivalents of the native sequence cytokines.

Chemokines can also be conjugated to the antibodies disclosed herein. Chemokines are a superfamily of small (approximately about 4 to about 14 kDa), inducible and secreted pro-inflammatory cytokines that act primarily as chemoattractants and activators of specific leukocyte cell subtypes. Chemokine production is induced by inflammatory cytokines, growth factors and pathogenic stimuli. The chemokine proteins are divided into subfamilies (alpha, beta, and delta) based on conserved amino acid sequence motifs and are classified into four highly conserved groups—CXC, CC, C and CX3C, based on the position of the first two cysteines that are adjacent to the amino terminus. To date, more than 50 chemokines have been discovered and there are at least 18 human seven-transmembrane-domain (7TM) chemokine receptors. Chemokines of use include, but are not limited to, RANTES, MCAF, MCP-1, and fractalkine.

The therapeutic agent can be a chemotherapeutic agent. In one embodiment, the chemotherapeutic agent is radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy, Ch.* 17 in Abeloff, Clinical Oncology 2$^{nd}$ ed., © 2000 Churchill Livingstone, Inc; Baltzer L., Berkery R. (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). Chemotherapeutic agents include those known by those skilled in the art, including but not limited to: 5-fluorouracil (5-FU), azathioprine, cyclopamine, cyclophosphamide, antimetabolites (such as Fludarabine), antineoplastics (such as etoposide, doxorubicin, methotrexate, and vincristine), carboplatin, cis-platinum, dacarbazine, temozolomide, PARP inhibitors and the taxanes, such as taxol. Rapamycin has also been used as a chemotherapeutic agent.

Effector molecules, such as, but not limited to, radionucleotide, cytokines, chemokines and chemotherapeutic agents, can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, label (such as enzymes or fluorescent molecules) drugs, toxins, polypeptides and other agents to antibodies one skilled in the art will be able to determine a suitable method for attaching a given agent to an antibody or other polypeptide.

The antibodies or antibody fragments that specifically bind endoplasmin disclosed herein can be derivatized or linked to another molecule (such as another peptide or protein). In general, the antibodies or portion thereof is derivatized such that the binding to endoplasmin is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

Methods for the detection of endoplasmin are provided herein, including methods for detecting cells expressing endoplasmin, such as melanoma, breast cancer, head and neck squamous cell carcinoma, renal cancer, lung cancer, glioma, bladder cancer, ovarian cancer or pancreatic cancer cells. These methods can include contacting a sample from a subject with an antibody that specifically binds endoplasmin, or antigen-binding fragment thereof, as disclosed herein. The methods can be used to detect a primary tumor, or can be used to detect metastases.

In some embodiments, methods are provided for detecting cancer or confirming the diagnosis of cancer in a subject. The method includes contacting a biological sample from the subject with an isolated antibody that specifically binds endoplasmin or antigen-biding fragment thereof and detecting binding of the isolated human monoclonal antibody, or antigen-binding fragment thereof to the sample. An increase in binding of the isolated human monoclonal antibody, or antigen-binding fragment thereof to the sample as compared to binding of the isolated human monoclonal antibody, or antigen-binding fragment thereof, to a control sample detects cancer in the subject or confirms the diagnosis of cancer in the subject. The control can be a sample from a subject known not to have cancer, or a standard value.

The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, and spinal fluid.

In some embodiments, the human antibody that specifically binds endoplasmin (the first antibody) is unlabeled and a second antibody or other molecule that can bind the antibody that specifically binds endoplasmin is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

A human antibody that specifically binds endoplasmin or antigen binding fragment thereof can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect endoplasmin by x-ray, emission spectra, magnetic resonance imaging (MRI), commuted tomography (CT) scan, positron emission tomography (PET), or other diagnostic techniques. Examples of labels for polypeptides include, but are not limited to, the following radioisotopes or radionucleotides: $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^{3}H$, $^{125}I$, $^{35}S$, $^{14}C$, or $^{32}P$), enzymes (such as horseradish peroxidase, alkaline phosphatase and others commonly used in an ELISA), and colorimetric labels such as colloidal gold or colored glass or plastic (such as polystyrene, polypropylene, latex, and the like) beads. These antibodies can be used in a variety of immunoassays, including Fluorescence activated cells sorting (FACS), immunohistochemistry, radio-immune assays (RIAs), and enzyme-linked immunosorbant assays (ELISA).

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

In one embodiment, a kit is provided for detecting endoplasmin in a biological sample, such as a blood sample. Kits for detecting a polypeptide will typically comprise a human antibody that specifically binds endoplasmin, such as any of the antibodies disclosed herein. In some embodiments, an antibody fragment, such as an Fv fragment is included in the kit. For in vivo uses, the antibody can be a scFv fragment. In a further embodiment, the antibody is labeled (for example, with a fluorescent, radioactive, or an enzymatic label).

In one embodiment, a kit includes instructional materials disclosing means of use of an antibody that specifically binds endoplasmin. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting endoplasmin in a biological sample generally includes the steps of contacting the biological sample with an antibody which specifically reacts, under immunologically reactive conditions, to endoplasmin. The antibody is allowed to specifically bind under immunologically reactive conditions to form an immune complex, and the presence of the immune complex (bound antibody) is detected directly or indirectly.

V. Endoplasmin Antibody Polynucleotides and Polypeptides

Nucleic acid molecules (also referred to as polynucleotides) encoding the polypeptides provided herein (including, but not limited to antibodies, antigen-binding fragments thereof, immunoconjugates and fusion proteins) can readily be produced by one of skill in the art, using the amino acid sequences provided herein, sequences available in the art, and the genetic code. In addition, one of skill can readily construct a variety of clones containing functionally equivalent nucleic acids, such as nucleic acids which differ in sequence but which encode the same effector molecule or antibody sequence. Thus, nucleic acids encoding antibodies, conjugates and fusion proteins are provided herein.

In some embodiments, the endoplasmin human monoclonal antibodies have a $V_H$ domain encoded by a nucleotide sequence comprising SEQ ID NO: 3. In some embodiments, the endoplasmin human monoclonal antibodies have a $V_L$ domain encoded by the nucleotide sequence comprising SEQ ID NO: 4. Exemplary nucleic acid sequences are provided below:

W9 VH sequence (hIgG1 Constant Heavy region in bold):

```
                                         (SEQ ID NO: 3)
CAGGTGCAGCTGGTGCAGTCTGGGGCTGAGGTGAAGAAGCCTGGGGCCT

CAGTGAAGGTTTCCTGCAAGGCTTCTGGATACACCTTCACTAGCTATGCT

ATGCATTGGGTGCGCCAGGCCCCCGGACAAAGGCTTGAGTGGATGGAT

GGATCAACGCTGGCAATGGTAACACAAAATATTCACAGAAGTTCCAGGG

CAGAGTCACCATTACCAGGGACACATCCGCGAGCACAGCCTACATGGAG

CTGAGCAGCCTGAGATCTGAAGACACGGCCGTGTATTACTGTGCAAGGG

CCCATTTTGACTACTGGGGCCAAGGTACCCTGGTCACCGTCTCGGCTAG

CACCAAGGGCCCATCGGTCTTCCCCCTGGCACCCTCCTCCAAGAGC

ACCTCTGGGGGCACAGCGGCCCTGGGCTGCCTGGTCAAGGACTACT

TCCCCGAACCGGTGACGGTGTCGTGGAACTCAGGCGCCCTGACCAG

CGGCGTGCACACCTTCCCGGCTGTCCTACAGTCCTCAGGACTCTACT

CCCTCAGCAGCGTGGTGACCGTGCCCTCCAGCAGCTTGGGCACCCA

GACCTACATCTGCAACGTGAATCACAAGCCCAGCAACACCAAGGTG

GACAAGAAAGTTGAGCCCAAATCTTGTGACAAAACTCACACATGCCC

ACCGTGCCCAGCACCTGAACTCCTGGGGGGACCGTCAGTCTTCCTC

TTCCCCCCAAAACCCAAGGACACCCTCATGATCTCCCGGACCCCTGA

GGTCACATGCGTGGTGGTGGACGTGAGCCACGAAGACCCTGAGGTC

AAGTTCAACTGGTACGTGGACGGCGTGGAGGTGCATAATGCCAAGA

CAAAGCCGCGGGAGGAGCAGTACAACAGCACGTACCGTGTGGTCAG

CGTCCTCACCGTCCTGCACCAGGACTGGCTGAATGGCAAGGAGTAC

AAGTGCAAGGTCTCCAACAAAGCCCTCCCAGCCCCCATCGAGAAAA

CCATCTCCAAAGCCAAAGGGCAGCCCCGAGAACCACAGGTGTACAC

CCTGCCCCCATCCCGGGAGGAGATGACCAAGAACCAGGTCAGCCTG

ACCTGCCTGGTCAAAGGCTTCTATCCCAGCGACATCGCCGTGGAGT

GGGAGAGCAATGGGCAGCCGGAGAACAACTACAAGACCACGCCTCC

CGTGCTGGACTCCGACGGCTCCTTCTTCCTCTACAGCAAGCTCACCG

TGGACAAGAGCAGGTGGCAGCAGGGGAACGTCTTCTCATGCTCCGT

GATGCATGAGGCTCTGCACAACCACTACACGCAGAAGAGCCTCTCC

CTGTCTCCGGGTAAATGA
```

W9 VL sequence (Human Kappa Constant Light region in bold):

```
                                         (SEQ ID NO: 4)
GAAATTGAGCTCACCCAGTCTCCATCCTCCCTGTCTGCATCTGTAGGAGA

CAGAGTCACCATCACTTGCCGGGCAAGTCAGAGCATTAGCAGCTACTTA

AATTGGTATCAGCAGAAACCAGGGAAAGCCCCTAAGCTCCTGATCTATG

CTGCATCCAGTTTGCAAAGTGGGGTCCCATCAAGGTTCAGTGGCAGTGG

ATCTGGGACAGATTTCACTCTCACCATCAGCAGTCTGCAACCTGAAGATT

TTGCAACTTACTACTGTCAACAGAGTTACAGTACCCCTCCAACGTTCGGC

CAAGGGACCAAGGTGGAGATCAAAACGGTGGCTGCACCATCTGTCTT

CATCTTCCCGCCATCTGATGAGCAGTTGAAATCTGGAACTGCCTCTG

TTGTGTGCCTGCTGAATAACTTCTATCCCAGAGAGGCCAAAGTACAG

TGGAAGGTGGATAACGCCCTCCAATCGGGTAACTCCCAGGAGAGTG

TCACAGAGCAGGACAGCAAGGACAGCACCTACAGCCTCAGCAGCAC

CCTGACGCTGAGCAAAGCAGACTACGAGAAACACAAAGTCTACGCC

TGCGAAGTCACCCATCAGGGCCTGAGCTCGCCCGTCACAAAGAGCT

TCAACAGGGGAGAGTGTTAG
```

Nucleic acid sequences encoding the human antibodies that specifically bind endoplasmin, or antigen-binding fragments thereof that specifically bind endoplasmin, can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding human antibodies that specifically bind endoplasmin, or functional fragments thereof that specifically bind endoplasmin, can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids encoding native effector molecule (EM) or anti-endoplasmin antibodies can be modified to form the EM, antibodies, or immunoconjugates of the present disclosure. Modification by site-directed mutagenesis is well known in the art. Nucleic acids can also be prepared by amplification methods Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one embodiment, immunoconjugates are prepared by inserting the cDNA which encodes a human endoplasmin-specific monoclonal antibody or antigen-binding fragment thereof into a vector which comprises the cDNA encoding the EM. The insertion is made so that the antibody and the EM are read in frame, that is in one continuous polypeptide which contains a functional antibody region and a functional EM region. In one embodiment, cDNA encoding an EM, label or enzyme is ligated to an antibody so that the EM, label or enzyme is located at the carboxyl terminus of the antibody. In another embodiment, the EM, label or enzyme is located at the amino terminus of the antibody. In a another example, cDNA encoding the EM, label or enzyme is ligated to a heavy chain variable region of an antibody, so that the EM, label or enzyme is located at the carboxyl terminus of the heavy chain variable region. The heavy chain-variable region can subsequently be ligated to a light chain variable region of the antibody using disulfide bonds. In a yet another example, cDNA encoding an EM, label or enzyme is ligated to a light chain variable region of an antibody, so that the EM, label or enzyme is located at the carboxyl terminus of the light chain variable region. The light chain-variable region can subsequently be ligated to a heavy chain variable region of the antibody using disulfide bonds.

Once the nucleic acids encoding an EM, anti-endoplasmin antibody, antigen-binding fragment thereof, or an immunoconjugate, are isolated and cloned, the desired protein can be expressed in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines.

One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

The expression of nucleic acids encoding the isolated antibodies and antibody fragments described herein can be achieved by operably linking the DNA or cDNA to a heterologous promoter (which is either constitutive or inducible), followed by incorporation into an expression cassette. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, maintenance of the correct reading frame of that gene to permit proper translation of mRNA, and stop codons.

To obtain high level expression of a cloned gene, it is desirable to construct expression cassettes which contain, at the minimum, a strong promoter to direct transcription, a ribosome binding site for translational initiation, and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, SV40 or cytomegalovirus, and a polyadenylation sequence, and can further include splice donor and acceptor sequences. The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or antigen-binding fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Modifications can be made to a nucleic acid encoding a polypeptide described herein (i.e., a human endoplasmin-specific monoclonal antibody or an immunoconjugate comprising the antibody) without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the recombinant immunoconjugates, antibodies, and/or effector molecules can be purified according to standard procedures of the art, including ammonium sulfate precipitation, affinity columns, column chromatography, and the like (see, generally, R. Scopes, PROTEIN PURIFICATION, Springer-Verlag, N.Y., 1982). The antibodies, immunoconjugates and effector molecules need not be 100% pure. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989, all incorporated by reference herein.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, incorporated by reference herein, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies and antigen-binding fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis, 2nd ed.*, Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

VI. Compositions and Therapeutic Methods

Compositions are provided herein that include a carrier and one or more of the antibodies that specifically bind endoplasmin, or antigen-binding fragment thereof that specifically binds endoplasmin. Compositions comprising immunoconjugates or immunotoxins are also provided. The compositions can be prepared in unit dosage forms for administration to a subject. The amount and timing of administration are at the discretion of the treating physician to achieve the desired purposes. The antibody can be formulated for systemic or local (such as intra-tumor) administration. In one example, the antibody that specifically binds endoplasmin is formulated for parenteral administration, such as intravenous administration.

The compositions for administration can include a solution of the antibody that specifically binds endoplasmin (or a functional fragment thereof that specifically binds endoplasmin) dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997.

Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

The antibody that specifically binds endoplasmin (or antigen-binding fragment thereof or immunoconjugate thereof) can be administered to slow or inhibit the growth of cells, such as cancer cells. In these applications, a therapeutically effective amount of an antibody is administered to a subject in an amount sufficient to inhibit growth, replication or metastasis of cancer cells, or to inhibit a sign or a symptom of the cancer. In some embodiments, the antibodies are administered to a subject to inhibit or prevent the development of metastasis, or to decrease the size or number of metasases, such as micrometastases, for example micrometastases to the regional lymph nodes (Goto et al., Clin. Cancer Res. 14(11):3401-3407, 2008).

Suitable subjects may include those diagnosed with a cancer that expresses endoplasmin, such as, but not limited to, melanoma, breast cancer, head and neck squamous cell carcinoma, renal cancer, lung cancer, glioma, bladder cancer, ovarian cancer or pancreatic cancer. A therapeutically effective amount of a human endoplasmin-specific antibody will depend upon the severity of the disease and the general state of the patient's health. A therapeutically effective amount of the antibody is that which provides either subjective relief of a symptom(s) or an objectively identifiable improvement as noted by the clinician or other qualified observer. These compositions can be administered in conjunction with another chemotherapeutic agent, either simultaneously or sequentially.

Many chemotherapeutic agents are presently known in the art. In one embodiment, the chemotherapeutic agents is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of the invention. Examples of useful COX-II inhibitors include CELEBREX™(alecoxib), valdecoxib, and rofecoxib. Examples of useful matrix metalloproteinase inhibitors are described in PCT Publication No. WO 96/33172 (published Oct. 24, 1996), PCT Publication No. WO 96/27583 (published Mar. 7, 1996), European Patent Application No. 97304971.1 (filed Jul. 8, 1997), European Patent Application No. 99308617.2 (filed Oct. 29, 1999), PCT Publication No. WO 98/07697 (published Feb. 26, 1998), PCT Publication No WO 98/03516 (published Jan. 29, 1998), PCT Publication No WO 98/34918 (published Aug. 13, 1998), PCT Publication No WO 98/34915 (published Aug. 13, 1998), PCT Publication No WO 98/33768 (published Aug. 6, 1998), PCT Publication No WO 98/30566 (published Jul. 16, 1998), European Patent Publication 606,046 (published Jul. 13, 1994), European Patent Publication 931,788 (published Jul. 28, 1999), PCT Publication No WO 90/05719 (published May 31, 1990), PCT Publication No WO 99/52910 (published Oct. 21, 1999), PCT Publication No WO 99/52889 (published Oct. 21, 1999), PCT Publication No WO 99/29667 (published Jun. 17, 1999), PCT International Application No. PCT/IB98/01113 (filed Jul. 21, 1998), European Patent Application No. 99302232.1 (filed Mar. 25, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997). In one example, the MMP inhibitors do not induce arthralgia upon administration. In another example, the MMP inhibitor selectively inhibits MMP-2 and/or MMP-9 relative to the other matrix-metalloproteinases (such as MMP-1, MMP-3, MMP-4, MMP-5, MMP-6, MMP-7, MMP-8, MMP-10, MMP-11, MMP-12, and MMP-13). Some specific examples of MMP inhibitors of use are AG-3340, RO 32-3555, RS 13-0830, 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R, 3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R, 3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxaicyclo [3.2.1]octane-3-carboxylic acid hydroxyamide; 3-endo-3-[4-(4-fluoro-phenoxy)-benzenesulfonylamino]-8-oxa-icyclo [3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

The antibodies that specifically bind endoplasmin can also be used with signal transduction inhibitors, such as agents that can inhibit EGF-R (epidermal growth factor receptor) responses, such as EGF-R antibodies, EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc.). EGF-R inhibitors are described in, for example in PCT Publication Nos. WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents also include, but are not limited to, the monoclonal antibodies C225 and anti-EGFR 22Mab (ImClone Systems Incorporated), ABX-EGF (Abgenix/Cell Genesys), EMD-7200 (Merck KgaA), EMD-5590 (Merck KgaA), MDX-447/H-477 (Medarex Inc. and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), C1-1033 (Warner Lambert Parke Davis), C1-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co.), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGF-R Vaccine (York Medical/Centro de Immunologia Molecular (CIM)).

VEGF inhibitors, for example SU-5416 and SU-6668 (Sugen Inc.), SH-268 (Schering), and NX-1838 (NeXstar) can also be used in conjunction with an antibody that specifically binds endoplasmin. VEGF inhibitors are described in, for example in PCT Publication No. WO 99/24440 (published May 20, 1999), PCT International Application PCT/IB99/00797 (filed May 3, 1999), PCT Publication No. WO 95/21613 (published Aug. 17, 1995), PCT Publication No. WO 99/61422 (published Dec. 2, 1999), U.S. Pat. No. 5,834,504 (issued Nov. 10, 1998), PCT Publication No. WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), PCT Publication No. WO 99/10349 (published Mar. 4, 1999), PCT Publication No. WO 97/32856 (published Sep. 12, 1997), PCT Publication No. WO 97/22596 (published Jun. 26, 1997), PCT Publication No. WO 98/54093 (published Dec. 3, 1998), PCT Publication No. WO 98/02438 (published Jan. 22, 1998), WO 99/16755 (published Apr. 8, 1999), and PCT Publication No. WO 98/02437 (published Jan. 22, 1998). Other examples of some specific VEGF inhibitors are IM862 (Cytran Inc.); anti-VEGF monoclonal antibody of Genentech, Inc.; and angiozyme, a synthetic ribozyme from Ribozyme and Chiron. These and other VEGF inhibitors can be used in conjunction with an antibody that specifically binds endoplasmin.

ErbB2 receptor inhibitors, such as GW-282974 (Glaxo Wellcome plc), and the monoclonal antibodies AR-209 (Aronex Pharmaceuticals Inc.) and 2B-1 (Chiron), can furthermore be combined with the compound of the invention, for example those indicated in PCT Publication No. WO 98/02434 (published Jan. 22, 1998), PCT Publication No. WO 99/35146 (published Jul. 15, 1999), PCT Publication No. WO 99/35132 (published Jul. 15, 1999), PCT Publication No. WO 98/02437 (published Jan. 22, 1998), PCT Publication No. WO 97/13760 (published Apr. 17, 1997), PCT Publication No. WO 95/19970 (published Jul. 27, 1995), U.S. Pat. No. 5,587,458 (issued Dec. 24, 1996), and U.S. Pat. No. 5,877,305 (issued Mar. 2, 1999). ErbB2 receptor inhibitors of use are also described in U.S. Provisional Application No. 60/117,341, filed Jan. 27, 1999, and in U.S. Provisional Application No. 60/117,346, filed Jan. 27, 1999.

The antibodies that specifically bind endoplasmin (or an antigen-binding fragment thereof) can be used with, and/or conjugated to, a cytokine or a chemokine, or can be conjugated to a cytokine or a chemokine. Exemplary cytokines include, but are not limited to, interferons (IFNs), such as IFN-α, IFN-β, and IFN-γ); tumor necrosis factor super family (TNFSF) members; human growth hormone; thyroxine; insulin; proinsulin; relaxin; prorelaxin; follicle stimulating hormone (FSH); thyroid stimulating hormone (TSH); luteinizing hormone (LH); hepatic growth factor; prostaglandin, fibroblast growth factor; prolactin; placental lactogen, OB protein; tumor necrosis faction (TNF)-α; TNF-β; integrin; thrombopoietin (TPO); nerve growth factors (NGFs) such as NGF-β; platelet-growth factor; transforming growth factor (TGF)-α; TGF-β; insulin-like growth factor-I and -II; erythropoietin (EPO); colony stimulating factors (CSFs) such as macrophage-CSF (M-CSF); granulocyte-macrophage-CSF (GM-CSF); and granulocyte-CSF (G-CSF); interleukins (IL-1 to IL-21), kit-ligand or FLT-3, angiostatin, thrombospondin, and endostatin. Suitable chemokines include, but are not limited to, RANTES, MCAF, MCP-1, and fractalkine.

For the treatment of cancer, such as melanoma, the antibodies disclosed herein can be used with surgical treatment, or with another therapeutic including dacarbazine (also termed DTIC), temozolomide, PARP inhibitors or interleukin-2 (IL-2) or interferon, such as interferon (IFN), or combinations of these agents. For the treatment of a superficial melanoma, the antibodies can be used in conjunction with Imiquimod. For the treatment of head and neck squamous cell carcinoma, the antibodies provided herein can be used in conjunction with surgery, radiation therapy, chemotherapy, other antibodies (such as cetuximab and bevacizumab) or small-molecule therapeutics (such as erlotinib).

Single or multiple administrations of the compositions are administered depending on the dosage and frequency as required and tolerated by the patient. In any event, the composition should provide a sufficient quantity of at least one of the antibodies (or antigen-binding fragments thereof) disclosed herein to effectively treat the patient. The dosage can be administered once but may be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems, J. Kreuter, ed., Marcel Dekker, Inc., New York, N.Y.*, pp. 219-342 (1994); and Tice & Tabibi, *Treatise on Controlled Drug Delivery*, A. Kydonieus, ed., Marcel Dekker, Inc. New York, N.Y., pp. 315-339, (1992) both of which are incorporated herein by reference.

Polymers can be used for ion-controlled release of the antibody compositions disclosed herein. Various degradable and nondegradable polymeric matrices for use in controlled drug delivery are known in the art (Langer, *Accounts Chem.*

Res. 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

Fully human monoclonal antibodies that specifically bind endoplasmin, or a antigen-binding fragment thereof, covalently linked to an effector molecule can be used for a variety of purposes, including for radioimmunotherapy or radioimmunoguided surgery. For example, an endoplasmin antibody can be linked to a radioactive isotope and used in immunotherapy to treat a tumor expressing endoplasmin A human endoplasmin antibody covalently linked to a radioactive isotope is of use to localize a tumor in radioimmunoguided surgery, such that the tumor can be surgically removed. In one embodiment, about 10 mCi of a radiolabeled human endoplasmin monoclonal antibody is administered to a subject. In other embodiments, about 15 mCi, about 20 mCi, about 50 mCi, about 75 mCi or about 100 mCi of a radiolabeled human endoplasmin monoclonal antibody is administered to a subject. In other embodiments, about 100 mCi to about 100 mCi of a radiolabled human endoplasmin monoclonal antibody is administered to a subject.

A method of detecting tumors in a subject in vivo includes the administration of a human antibody that specifically binds endoplasmin, or antigen-binding fragment thereof, complexed to an effector molecule, such as a radioactive isotope. After a sufficient amount of time has elapsed to allow for the administered radiolabeled antibody to localize to the tumor, the tumor is detected. In one specific, non-limiting example, a radiolabeled immune complex is detected using a hand held gamma detection probe. In some embodiments, the tumor is detected by MRI, CT scan or PET scan. Primary tumors, metastasized tumors, or cells expressing endoplasmin can be detected. For example, a human endoplasmin monoclonal antibody complexed to an effector molecule, such as a radioactive isotope, is administered to a subject prior to surgery or treatment. In one specific embodiment, the detection step is performed prior to surgery to localize the tumor. In another embodiment, the detection step is performed during surgery, for example to detect the location of the tumor prior to removing it, as in radioimmunoguided surgery. A human endoplasmin monoclonal antibody complexed to an effector molecule, such as a radioactive isotope, can also be administered to a subject following surgery or treatment, to determine the effectiveness of the treatment, such as to ensure the complete removal of the tumor, or to detect a recurrence of the tumor. Thus, the antibodies are of use as therapeutic agents (such as for immunotherapy against tumors) or for carrying out radioimmunoguided surgery.

VI. Diagnostic Methods and Kits

A method is provided herein for the detection of the expression of endoplasmin in vitro. In one example, expression of endoplasmin is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine.

In several embodiments, a method is provided for detecting a malignancy such as squamous cell carcinoma (such as head and neck squamous cell carcinoma), melanoma, renal cancer, lung cancer, glioma, bladder cancer, ovarian cancer or pancreatic cancer. Antibodies that specifically bind endoplasmin, or antigen-binding fragments thereof, can be used to detect endoplasmin in a serum sample from a subject to detect cancer in the subject, or confirm a diagnosis of cancer in a subject. The antibodies can also be used to identify the original of a metastatic lesion.

The disclosure provides a method for detecting endoplasmin in a biological sample, wherein the method includes contacting a biological sample with a human antibody that binds endoplasmin, or an antigen-binding fragment thereof, under conditions conducive to the formation of an immune complex, and detecting the immune complex, to detect the endoplasmin in the biological sample. In one example, the detection of endoplasmin in the sample indicates that the subject has a malignancy. In another example, detection of endoplasmin in the sample confirms a diagnosis of cancer in a subject. In a further example, detection of endoplasmin confirms or detects the presence of metastases.

In some embodiments, the fully human monoclonal antibody that specifically binds endoplasmin, or antigen-binding fragment thereof, is used for detection or diagnosis of a tumor in a subject, such as confirming the diagnosis of a tumor in a subject. In other embodiments, the fully human monoclonal antibody that specifically binds endoplasmin, or antigen-binding fragment thereof, is used to detect the efficacy of a therapy. For example, a subject with a known malignancy that expresses endoplasmin is administered a therapeutic agent. The method can include contacting a biological sample with a human antibody that binds endoplasmin, or an antigen-binding fragment thereof, under conditions conducive to the formation of an immune complex, and detecting the immune complex, to detect the endoplasmin in the biological sample. A decrease in the amount of endoplasmin, as compared to a control, such as a sample from the subject prior to treatment or a reference standard, indicates that the therapeutic agent is effective at treating the malignancy. In some examples, an increase in the amount of endoplasmin, as compared to the control indicates that the therapeutic agent is not effective for treating the malignancy.

In some embodiments, the detection can be in vivo. The human monoclonal antibody that specifically binds endoplasmin, or antigen-binding fragment thereof, can be complexed to a radioactive isotope. After a sufficient amount of time has elapsed to allow for the administered radiolabeled antibody to localize to the tumor, the tumor is detected, such as by MRI, CT scan or PET scan (see above).

In one embodiment, the human antibody that specifically binds endoplasmin or antigen-binding fragment thereof is directly labeled with a detectable label. In another embodiment, the human antibody that specifically binds endoplasmin or antigen-binding fragment thereof (the first antibody) is unlabeled and a second antibody or other molecule that can bind the human antibody that specifically binds endoplasmin is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$.

In an alternative embodiment, endoplasmin can be assayed in a biological sample by a competition immunoassay utilizing endoplasmin standards labeled with a detectable substance and an unlabeled human antibody that specifically binds endoplasmin. In this assay, the biological sample, the labeled endoplasmin standards and the human antibody that specifically bind endoplasmin or antigen-binding fragment thereof are combined and the amount of labeled endoplasmin standard bound to the unlabeled antibody is determined. The amount of endoplasmin in the biological sample is inversely proportional to the amount of labeled endoplasmin standard bound to the antibody that specifically binds endoplasmin, or antigen-binding fragment thereof.

The immunoassays and methods disclosed herein can be used for a number of purposes. In one embodiment, the human antibody that specifically binds endoplasmin or antigen-binding fragment thereof may be used to detect the production of endoplasmin in cells in cell culture. In another embodiment, the antibody can be used to detect the amount of endoplasmin in a biological sample. Increased expression of endoplasmin is associated with several types of cancer, including, but not limited to melanoma, breast cancer, head and neck squamous cell carcinoma, renal cancer, lung cancer, glioma, bladder cancer, ovarian cancer or pancreatic cancer. In one embodiment, a kit is provided for detecting endoplasmin in a biological sample, such as a serum sample or tissue sample. For example, to confirm a cancer diagnosis in a subject, a biopsy can be performed to obtain a tissue sample for histological examination. Alternatively, a serum sample can be obtained to detect the presence of endoplasmin protein. Kits for detecting a polypeptide will typically comprise a human antibody that specifically binds endoplasmin, such as any of the antibodies disclosed herein. In some embodiments, an antibody fragment, such as an Fv fragment or scFv, or a Fab is included in the kit. In a further embodiment, the antibody is labeled (for example, with a fluorescent, radioactive, or an enzymatic label).

In one embodiment, a kit includes instructional materials disclosing means of use of an antibody that specifically binds endoplasmin. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting endoplasmin in a biological sample generally includes the steps of contacting the biological sample with an antibody or antibody fragment which specifically reacts, under immunologically reactive conditions, to an endoplasmin polypeptide. The antibody is allowed to specifically bind under immunologically reactive conditions to form an immune complex, and the presence of the immune complex (bound antibody) is detected directly or indirectly.

When the antibody is used to detect cancer or confirm diagnosis of cancer in a subject, the information about the diagnosis can be displayed on a medium of expression, such as an electronic or paper medium. An electronic medium can include, for example, a computer database, a display monitor, or an electronic medical record. A paper medium includes, for example, a test result or paper record as recorded by a laboratory or clinician.

In some embodiments, once a diagnosis of the tumor (such as the melanoma) is made, the subject is treated for the tumor (such as the melanoma). For example, the treatment of can include surgical excision of a primary or metastatic lesion and/or administration of a chemotherapeutic regimen for the treatment of the disease.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radio-immunoassays (RIAs), enzyme linked immunosorbent assays (ELISA), or immunohistochemical assays. The antibodies can also be used for fluorescence microscopy or fluorescence activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620). Any of the human antibodies that specifically bind endoplasmin, as disclosed herein, can be used in these assays. Thus, the antibodies can be used in a conventional immunoassay, including, without limitation, an ELISA, an RIA, FACS, tissue immunohistochemistry, Western blot or immunoprecipitation.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

The disclosure is illustrated by the following non-limiting Examples.

EXAMPLES

Convincing clinical evidence has shown that antibody-based immunotherapy can be effective in the treatment of hematological malignancies and solid tumors. To eliminate the influence of the immunogenicity of tumor antigens on the specificity of the developed antibodies, a synthetic phage single chain variable region (scFv) library was used to isolate human antibodies which recognize cell-surface molecules that are up-regulated on malignant cells. Antibodies were isolated that specifically bind endoplasmin.

Panning of the synthetic phage scFv library with the human melanoma cell line WM1158 has resulted in the isolation of a scFv fragment, named W9, which displays high reactivity with a large panel of human cell lines. SDS-PAGE analysis of the antigen immunoprecipitated by scFv W9 from cell lines identified a 94-KDa component. The determinant recognized by scFv W9 includes carbohydrates, since its expression was markedly reduced on cells incubated with tunicamycin. Mass spectrometry-based analysis of the band immunoprecipitated by scFv W9 from various cell lines identified the 94-KDa component as endoplasmin, a member of the 90-KDa molecular chaperone family. This conclusion was corroborated by the reactivity of scFv W9 with the endoplasmin (Grp94) recombinant canine protein, which displays a 98.5% homology in the amino acid sequence with human endoplasmin (Grp94). The determinant recognized by scFv W9 is not expressed on normal cells. The antibody was effective in inducing apoptosis and inhibited cancer cell growth. Thus, the results disclosed herein document that antibodies that specifically bind endoplasmin, such as scFv W9, are of use for the immunotherapy of malignant diseases. These antibodies also can be used to detect malignant disease.

Example 1

Materials and Methods

The following materials and methods were used in the below examples:

Cell Lines: The human melanoma cell lines WM1158, MV3, COLO38, SK-MEL-28, M14, and FO-1, the human breast carcinoma cell lines SUM149, MDA-MB-435s, MCF-7, T47D, the human head and neck cancer cell line PCI-13, human pancreatic cell lines Panc 2.03, Panc 3.27, Panc 10.05, the human colon cancer cell line 40-16, the human renal cancer cell line SLR21, the human prostate cancer cell line Du145, the human ovarian cancer cell line OVCAR3, the human glioma cancer cell line U-138, the human cervical cancer cell line HeLa and the human B lymphoid cell line LG2 were maintained in RPMI 1640 medium (Cellgro, Mediatech, Washington, D.C., USA) supplemented with 10% fetal bovine serum (FBS: BioWhittaker, Walkersville, Md., USA) and and 2 mM L-glutamine (BioWhittaker). The human bladder cancer cell line T24, the human lung cancer cell line A549, the human epidermoid cancer cell line A431, the human glioma cancer cell line A-172 and human 293 cell line were grown in DMEM medium (Lonza, Verviers, Belgium) supplemented wityh 10% FBS. Cells were cultured at 37° C. in a 5% $CO_2$ atmosphere.

Monoclonal antibodies, scFv antibodies and reagents: The C-myc oncoprotein-specific mouse mAb 9E10 (Evan, et al., Mol Cell Biol, 1985 December; 5(12):3610-6). and the HLA-class I antigen-specific mouse mAb TP25.99 (D'Urso et al., J Clin Invest. 1991 January; 87(1): 284-292) have been previously described. The anti-anti-id scFv #119 (Wang et al., 1997. *The anti-idiotypic approach to active specific immunotherapy of malignant melanoma*. In idiotypes in Medicine: Autoimmunity, Infection and Cancer. Y. Shoenfeld, R. Kennedy, and S. Ferrone, eds. Elsevier, Amsterdam, p. 523) was isolated from the synthetic scFv library (#1) (Nissim et al., 1994. Embo J 13:692-698) by panning with the anti-id mAb MK2-23. Mouse mAb were purified from ascitic fluid by sequential ammonium sulphate and caprylic acid precipitation (Temponi et al., 1989, Hybridoma 8:85-95). The purity and activity of mAb preparations were assessed by SDS-PAGE and by testing with the corresponding antigen in a binding assay, respectively. HRP-anti-mouse IgG Fc antibodies were purchased from Jackson ImmunoResearch (Laboratories, Inc., West Grove, Pa., USA). R-phycoerythrin (RPE)-labeled F(ab')$_2$ fragments of goat anti-mouse Ig antibodies were purchased from BD Pharmingen (San Diego, Calif., USA). The endoplasmin (Grp94) recombinant canine protein was purchased from Stressgen Biothecnology Corporation (Victoria, British Columbia, Canada).

Phage display libraries: The semi-synthetic phage library of human single chain Fv (scFv) antibodies was constructed as described by Nissim et al. 1994, Embo J 13:692-698).

Selection of phage display scFv antibodies: Phage display scFv antibodies binding to melanoma cells were isolated from the phage display scFv antibody library as previously described (Noronha et al. 1998, J Immunol 161:2968-2976). Briefly phage particles ($1\times10^3$) were added to a polypropylene culture tube containing $1\times10^7$ WM1158 melanoma cells. Following a 90 min of incubation at R/T, unbound phages were removed by washing the cells six times with PBS. Bound phage were eluted by adding 200 μl of 0.1M glycine-HCl (pH=2.2). Following four rounds of panning, the isolated clones were adsorbed against human B-lymphoid cells, LG-2, to remove phages binding to Ags shared by human melanoma and lymphoid cells.

Binding Assay: The ELISA to test the reactivity of soluble scFv W9 antibody with tumor cell lines and endoplasmin (Grp94) recombinant canine protein was performed as described (Noronha et al., 1998, J Immunol 161:2968-2976). Results are expressed as absorbance of optical density (O.D.) at 450 nm.

Immunoprecipitation experiments: WM1158 cells ($3\times10^7$) were washed, pelleted, and lysed in 1.5 ml of lysis buffer (50 mmol/L Tris, 4 mmol/L EDTA, 150 mmol/L NaCl, 0.5% NP40 containing 1 mmol/L phenylmethylsulfonyl fluoride) containing protease inhibitors. Following a 30 min of incubation on ice, the cell lysate was spun at 13,000×g for 30 min at 4° C. The supernatant was collected, precleared by incubation with PG-Sepharose (Amersham Pharmacia Biotech AB, Uppsala, Sweden), and transferred to a tube containing 15 μl of packed protein G Sepharose, previously armed with 15 μg of mAb 9E10 and the periplasmic preparation of scFv W9, and 119 (negative control). Following a 2 h of incubation at 4° C., beads were washed 4 times with PBS, twice with high salt buffer (350 mmol/L NaCl, 1 mmol/L EDTA, 10 mmol/L Tris, 0.1% bovine serum albumin, 1% NP40), and 2 times with lysis buffer. Precipitated proteins were eluted in SDS sample buffer, resolved on a reducing 12% Tris-HCl SDS-polyacrylamide gel and stained with Coomassie blue.

Tunicamycin treatment: COLO38 cells were cultured in the presence of 0.5 μg/ml of tunicamycin (MP Biomedicals, Solon, Ohio, USA) for 72 hours at 37° C. in a 5% $CO_2$ atmosphere. Cells incubated in medium with DMSO alone were used as a control.

Transfection: 293 cells were transfected with 3 μg of Grp 94 HSP90B1 cDNA clone (Origene) using the Amaxa nucleofection technology and following the manufacturer's instructions (Amaxa, Cologne, Germany). The nucleofector program Q-001 was used. After transfection, cells were immediately suspended in 500 μl of pre-warmed DMEM culture medium supplemented with 10% FBS and plated in 6-well plates in a humidified 37° C., 5% $CO_2$ incubator for 24 hours. Transfection efficiency was determined by flow cytometric analysis of GFP. The pCMV6-XL4 vector was used as a control. Transfection with Lipofectamine 2000 (Invitrogen, Carlsbad, Calif., USA) was performed according to the manufacturer's instructions. The transfection of cells with endoplasmin (Grp94) siRNA and the control siRNA (Fluorescein Conjugate)-A (Santa Cruz Biotechnology, Santa Cruz, Calif., USA) was carried out according to the manufacturer's instructions.

The following materials and methods were also used (see Examples 5 and 9):

Cell lines, cell lysates and tissues. The human melanoma cell lines M21, MV3 and SK-MEL-5, the human pancreatic adenocarcinoma cell lines MiaPaCa-2 and PANC1, the human glioma cell line U1338MG, the human breast carcinoma cell lines SUM149 and MDA-MB-231, the human mesothelioma cell line Phi, the human colon cancer cell line RKO, the human ovarian cancer OVCAR3, the human sarcoma cell line HT1080, the human multiple myeloma cell line MM.8, the human B lymphoid cell line RAJI, and the mouse myeloma cell line NSO were maintained in RPMI 1640 medium supplemented with 2 mM L-glutamine (Cellgro) and 10% fetal bovine serum (FBS) (PAA Laboratories Inc). Cells were cultured at 37° C. in a 5% CO2 atmosphere. Cell lysates were prepared as described (Desai et al.. Cancer Res 1998; 58(11):2417-25).

Animals. C.B-17 SCID mice (8-10 weeks old) were obtained from Taconic Farms, Inc.

Monoclonal and polyclonal antibodies, scFv antibodies and reagents. The HLA class I antigen-specific mouse mAb TP25.99 (Desai et al., J Immunol 2000; 165(6):3275-83), the calnexin-specific mAb TO-5 (used as a loading control) were developed and characterized as described (Ogino et al., Tissue Antigens 62:385-393, 2003). Purified human immunoglobulins were purchased from Sigma-Aldrich. Antibodies specific for FAK and phosphorylated FAK (Tyr397) and for ERK1/2 and phosphorylated 44/42 ERK1/2, AKT and phosphorylated 473 AKT, MET phosphorylated MET, PKC, β-catenin, Ras, B-Raf, C-Raf, cleaved Caspase-3, cleaved Caspase-7 SHh,GLI1 and β-actin were purchased from BD Bioscience and from Cell signaling technology. The rat-anti-endoplasmin (Grp94) antibody was purchased from StressGen. Mouse mAb were purified from ascitic fluid by sequential ammonium sulphate and caprylic acid precipitation (Temponi et al., Hybridoma 1989;8(1):85-95.). The purity and activity of mAb preparations were assessed by SDS-PAGE and by testing with the corresponding antigen in a binding assay, respectively.

HRP-anti-mouse, -rabbit, and rat antibodies and RPE-labeled F(ab')$_2$ fragments of goat anti-human IgG Fcγ antibody were purchased from Jackson ImmunoResearch Laboratories Inc. RPE-labeled F(ab')$_2$ fragments of goat anti-mouse Ig antibodies were purchased from BD Pharmingen.

Construction of fully human mAb W9. The gene encoding scFv W9 variable light (VL) and heavy (VH) regions were amplified by PCR and cloned into the pFUSE2-CLIg-hk and pFUSE-CHIg-hG1, respectively (InvivoGen), utilizing the DNA Ligation Kit, MIGHTY MIX® (TAKARA Bio USA) according to the manufacturer's instructions.

Fully human mAb W9 expression and purification. Expression plasmids pFUSE2-CLIg-hk and pFUSE-CHIg-hG1 were co-transfected into the mouse myeloma cell line NSO using electroporation (GENE PULSER® II Electroporation System Bio-Rad) according to the manufacturer's instructions. The transfected cells were selected in RPMI 1640 medium supplemented with 10% FCS, Zeocin (50 μg/mL), and Blasticidin S (10 μg/mL). Cells resistant to Zeocin and Blasticidin S were then single-cell-subcloned by limiting dilution. The spent supernatants of subcloned cells were screened by ELISA for the expression of human Fc and (Fab')$_2$ and for the reactivity with the corresponding antigens.. The fully human mAb W9 was purified from either spent culture supernatant or mouse ascites, using HITRAP® protein G HP column (GE healthcare) according to the manufacturer's instructions. The purity and activity of purified mAb W9 was determined by SDS-PAGE and antigen binding assays, respectively.

Endoplasmin (Grp94) deglycosaylation. Grp94$^+$ MIAPaCa-2 cells (5×10$^5$) were incubated with or without 2 μl PNGase F, 2 μl O-Glycosidase and 2 μl α-2(3,6,8.9)-Neuraminidase (Enzymatic Protein Degylcosylation Kit, Sigma) in 50 μl RPMI1640 medium for 24 hours at 37° C. The treated cells were then stained with mAb W9 and analyzed by flow cytometry (Cyan, Beckman Coulter).

Flow cytometry analysis. Cells (2×10$^5$) were incubated for 30 min at 4° C. with 2 μg/ml of mAb W9 (diluted in a total volume of 100 μl of 2% BSA-PBS). Cells were then washed twice with 0.5% BSA-PBS and incubated for 30 min at 4° C. with an optimal amount of RPE-labeled F(ab')$_2$ fragments of goat anti-human IgG Fcγ antibody (Jackson ImmunoResearch, Inc). Following three washes, cells were fixed in 2% formaldehyde and analyzed with a CYAN™ ADP LX 9 Color flow cytometer (Dako). mAb TP25.99 and human immunoglobulins were used as a control. For cancer initiating cell binding assay cells were previously stained with ALDEFLUOR® (Stem Cell Technologies) following the manufacturer's instructions.

Immunohistochemistry. Frozen sections of surgically removed human pancreatic adenocarcinoma lesion and normal pancreas tissues were fixed by 4% formaldehyde/PBS for 20 minutes at room temperature. IHC staining of TMA slides with scFv-FcC21 was performed as described (Wang et al., Curr. Mol. Med 2010). Pictures of stained tissue microarrayslides were taken using OLYMPUS® BX51 microscope (OLYMPUS UK Ltd) at a magnification ×200 for review.

Cell proliferation and MTT assays. Cells were seeded at a density of 1×10$^4$ per well in 96-well plates were incubated with mAb W9 (5 μg/ml) in medium supplemented with 1% FCS for 3 days. The viable cell numbers at different time points were measured by adding 10 μl per well of tetrazolium component methylthiazolyldiphenyl-tetrazolium bromide (Sigma-Aldrich, Inc. St Louis, Mo.) and the mixture was incubated for approximately 3-4 hours at 37° C. Metabolically active, viable cells converted MTT into a colored formazan product that was measured in a spectrophotometric microplate reader (MTX Lab System, Inc, Vienna, Va.) at 540 nm. The results were expressed as percent inhibition of living cells, using the number of living cells incubated with PBS only as a 100% reference.

Apoptosis. Flow cytometry analysis of apoptotic and necrotic MV3 and MIAPaca-2 cells following a 6 hr incubation with mAb W9 (50 µg/mL) was performed by Annexin V-FTIC and propidium iodide (PI) staining kit (BD PharMingen), as per the manufacturer's specifications.

Western Blot. Proteins in cell lysates were separated by 8% sodium dodecyl sulfate—polyacrylamide gel electrophoresis (SDS-PAGE) and transferred onto 0.45-µm (pore size) PVDF membranes (Millipore). After blocking with 5% nonfat dry milk plus 2% BSA overnight at 4° C., membranes were sequentially incubated with the appropriate concentration of primary antibodies for overnight at 4° C. and HRP-labeled respective secondary antibodies for 45 min at room temperature. Bands were visualized with the enhanced chemiluminescence system (GE Life Science), and band density was read with the FOTO/Analyst® Investigator Eclipse system (Fotodyne Incorporate). The calnexin-specific mAb TO-5 and β-actin specific mAb were used as loading control.

Immunoprecipitation. MV3 cells ($3 \times 10^7$) were washed, pelleted, and lysed in 1.5 ml of lysis buffer (50 mmol/L Tris, 4 mmol/L EDTA, 150 mmol/L NaCl, 0.5% NP40 containing 1 mmol/L phenylmethylsulfonyl fluride) containing protease inhibitors. Following a 30 minute incubation on ice, the cell lysate was spun at 13,000×g for 30 min at 4° C. The supernatant was collected, precleared by incubation with PG-Sepharose (Amersham Pharmacia Biotech AB, Uppsala, Sweden), and transferred to a tube containing 10 µl of packed protein G Sepharose, previously armed with 10 µg of mAb mAb W9. Following 2 hours of incubation at 4° C., beads were washed 4 times with PBS, twice with high salt buffer (350 mmol/L NaCl, 1 mmol/L EDTA, 10 mmol/L Tris, 0.1% bovine serum albumin, 1% NP40), and 2 times with lysis buffer. Precipitated proteins were eluted in SDS sample buffer, resolved on a reducing 12% Tris-HCl SDS-polyacrylamide gel and transferred onto 0.45-µm (pore size) PVDF membranes (Millipore). The blotting was performed as previously described.

ADCC: MV3 cells were labeled with 50 µCi of $^{51}$Cr (Perkin Elmer) and resuspended at a density of $0.4 \times 10^6$ cells/ml. $^{51}$Cr labeled cells were mixed with mAb W9 (50, 10, and µg/ml 50 µl/well) in a 96-well tissue culture-U-bottom assay plate (BD. Falcon). Human immunoglobulins were used as a control. Following a 30 minute-incubation at 4° C., PBMC (40:1 effector to target (E:T)) were added and incubated for 4 hours at 37° C. in a $CO_2$ incubator. $^{51}$Cr release was determined by counting the cell free supernatant using Packard TOPCOUNT™ Microplate Scintillation Counter (Conroe). The experiment was performed twice in triplicate.

CDC. Target cells MV3 were labeled with 50 µCi of $^{51}$Cr and resuspended at a density of $1 \times 10^6$ cells/ml. MV3 cells were incubated with mAb W9 (50, 10, and µg/ml 50 µl/well) in presence of human serum complement (Quidel) diluted four times in RPMI 1640, 10 mM HEPES, 0.1% BSA. Human immunoglobulins were used as a control. Following a 2-hour incubation at 37° C. in a $CO_2$ incubator, $^{51}$Cr release was determined by counting the cell free supernatant using Packard TOPCOUNT™ Microplate Scintillation Counter. The experiment was performed twice in triplicate.

Treatment of mice bearing established human melanoma cell-derived lung metastasis. Eight-week-old, female SCID mice were injected intravenously (i.v.) with the human melanoma MV3 cells ($1.4 \times 10^8$ cells/mouse). Fifteen days following the i.v. injection of cells, mice were randomly divided into two groups of 13 mice each. One group of mice was injected i.v. with mAb W9 (100 µg/per mouse) every 48 hours for a total of 3 injections. The other group of mice was injected i.v. with human immunoglobulins, utilizing the same schedule. On day 25 mice were sacrificed, lungs were collected and subjected to FFPE. H&E stained lung tissue sections were examined microscopically for metastasis.

Statistical analysis. The statistical significance of the difference between the results obtained in the tested groups was analyzed using the Student's t-test. Survival statistics was analyzed using MEDCALC® software (Mariakerke, Belgium).

Example 2

Isolation of Melanoma Cell-Binding scFv Fragments

Figure 1A:
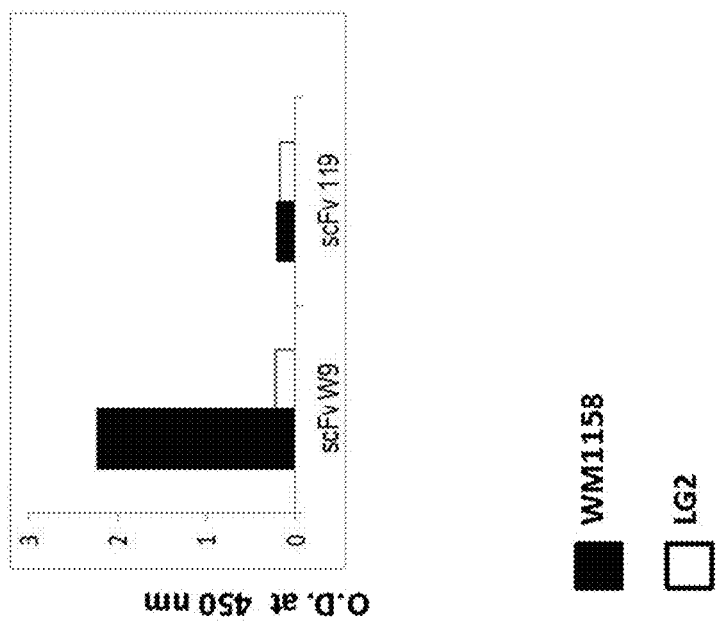
FIG. 1A. Panning of a phage display scFv library with the human melanoma cell line WM1158. The phage display scFv library contains a large of phage displaying scFv fragments with different specificity. The library was added to a tube containing WM1158 melanoma cell suspension. Following washing of the tube to remove unbound phage, bound phage were eluted at a high pH and amplified in bacterial host *E. coli* TG1. Following three rounds of panning, the isolated clones were absorbed with cultured human LG2 B lymphoid cells to remove the phage that bound to the Ags shared by human melanoma and lymphoid cells. The isolated phage were then screened for reactivity with WM1158 cells in ELISA.
Figure 1B:
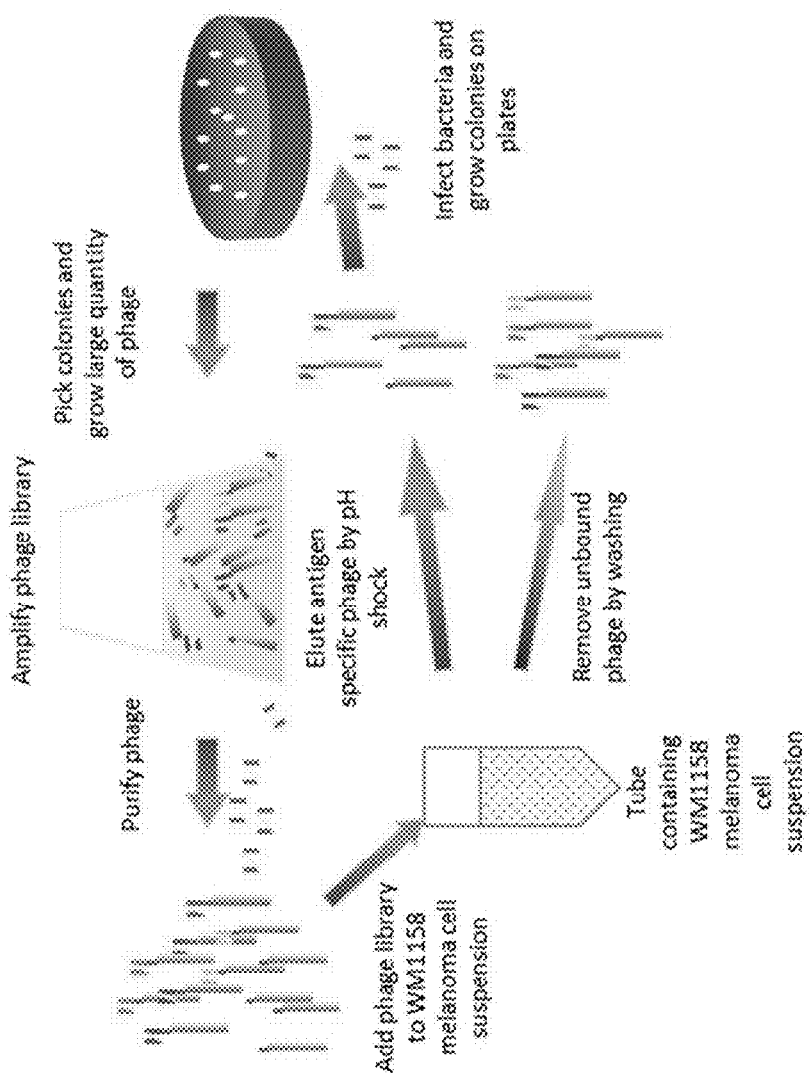
FIG. 1B. Differential reactivity with the melanoma cell line WM1158 and with the B lymphoid cell line LG2 of the scFv W9 isolated by panning a phage display antibody library with WM1158 cells. WM1158 cells were plated in a 96-well plate and incubated with scFv W9 for 2 hours at room temperature. The binding of scFv was detected using c-myc-specific mAb 9E10 and HPR-streptavidin. scFv 119, which recognizes an irrelevant antigen and LG2 cells were used as negative controls. scFv W9 reacts specifically with WM1158 cell line.

The synthetic phage scFv library (#1) was subjected to four rounds of panning with WM1158 cells. Isolated phages were absorbed with cultured human LG-2 B lymphoid cells to remove the phages binding to the Ags shared by human cells. Soluble scFvs were produced from 80 clones and tested for reactivity with melanoma cells in a cell ELISA. Among the clones tested, the scFv named W9, strongly reacted with the WM1158 cell line. The reactivity was specific since no reactivity with LG-2 cells was detected. The scFv #119, which recognizes an irrelevant antigen, was used as a negative control (FIG. 1).

Example 3

Reactivity of scFv W9

Figure 2:
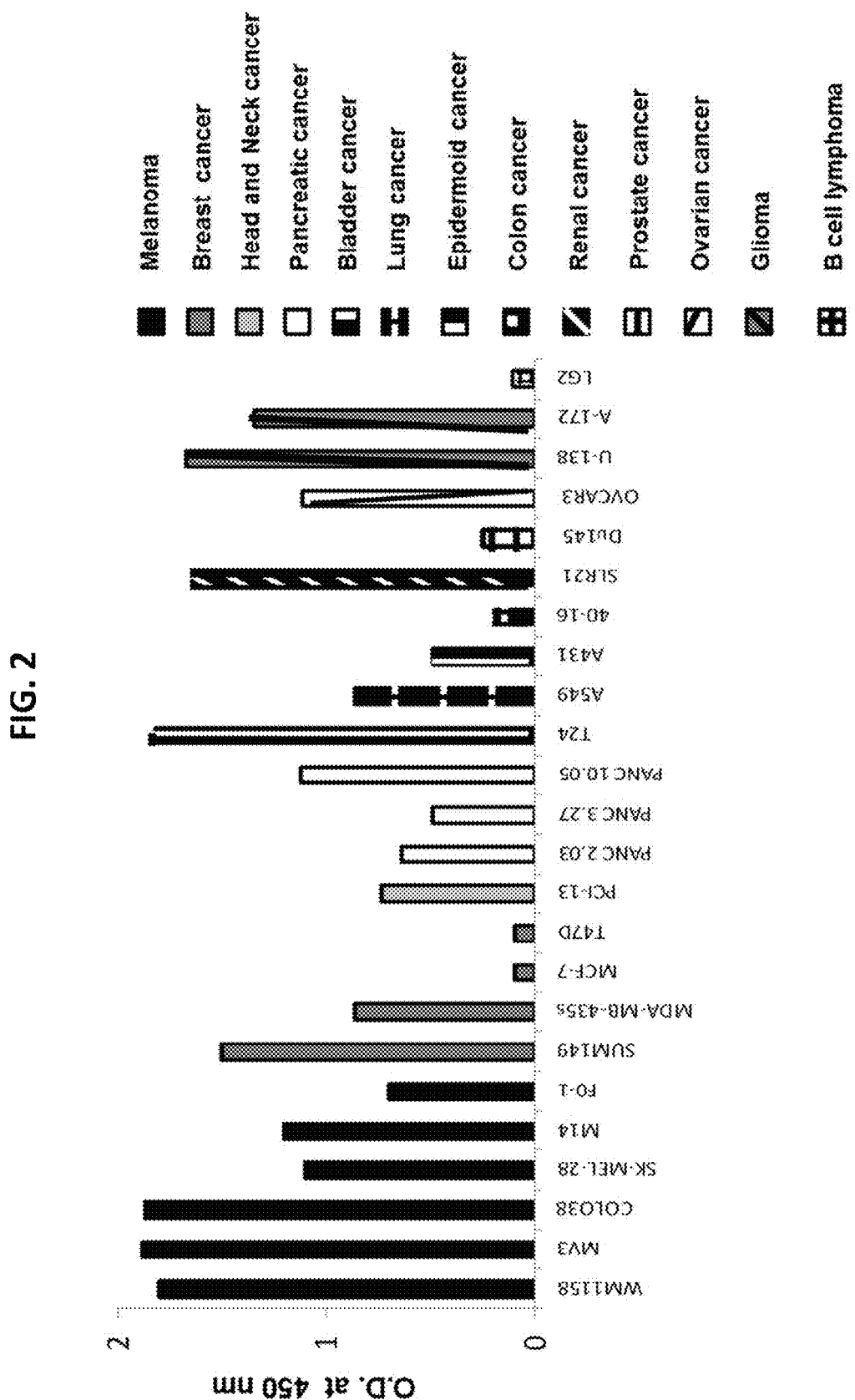
FIG. 2. Reactivity of scFv W9 with many types of human cell lines. Six melanoma, four breast, one head and neck squamous cell, three pancreas, one bladder, one lung, one epithelial, one colon, one renal, one prostate, and one ovarian cancer cell lines were plated in a 96-well plate and incubated with scFv W9 for 2 hours at room temperature. The binding of scFv was detected using c-myc-specific mAb 9E10 and HPR-streptavidin. scFv W9 reacted with all the melanoma cell lines, with two breast cancer cell lines, and with head and neck squamous cell, pancreas, bladder, lung, epithelial, renal, ovarian and glioma cancer cell lines.

When tested by ELISA with a panel of human cell lines, the soluble scFv W9 reacted with melanoma (MV3, COLO38, SK-MEL-28, M14, FO-1), basal breast cancer (SUM149, MDA-MB-435s), head and neck (PCI-13), pancreatic (PANC 2.03, PANC 3.27, PANC 10.05), bladder (T24), lung (A549), epidermoid (A431), cervical (HeLa), renal (SLR21), ovarian (OVCAR3), and glioma (U-138, A-172) cancer cell lines. The scFv fragment did not react with the luminal breast cancer cell lines (MCF-7, T47D), the colon cancer cell line 40-16, the prostate cancer cell line Du145, and the B lymphoid cell line LG-2 (FIG. 2).

The results from an immunohistochemical analysis of scFv W9 immunoreactivity with normal tissues is presented below. Results are related to biopsies of at least two patients tested ([+]Positive).

| TISSUES* | W9 |
|---|---|
| Skin | sweat gland only: + |
| Kidney | negative |
| Lung | negative |
| Liver | negative |
| Colon-rectum | negative |
| Pancreas | negative |
| Stomach | negative |
| Thyroid | negative |
| Brain Cortex | negative |
| Testis | negative |
| Parotid | acinar epithelium only: + |
| Breast | negative |

| TISSUES* | W9 |
|---|---|
| Prostate | negative |
| Spleen | negative |

Immunohistochemical staining with scFv W9 showed that endoplasmin (Grp94) is expressed by sweat gland and acinar epithelium only while it is not expressed by a variety of normal tissues.

Figure 11:
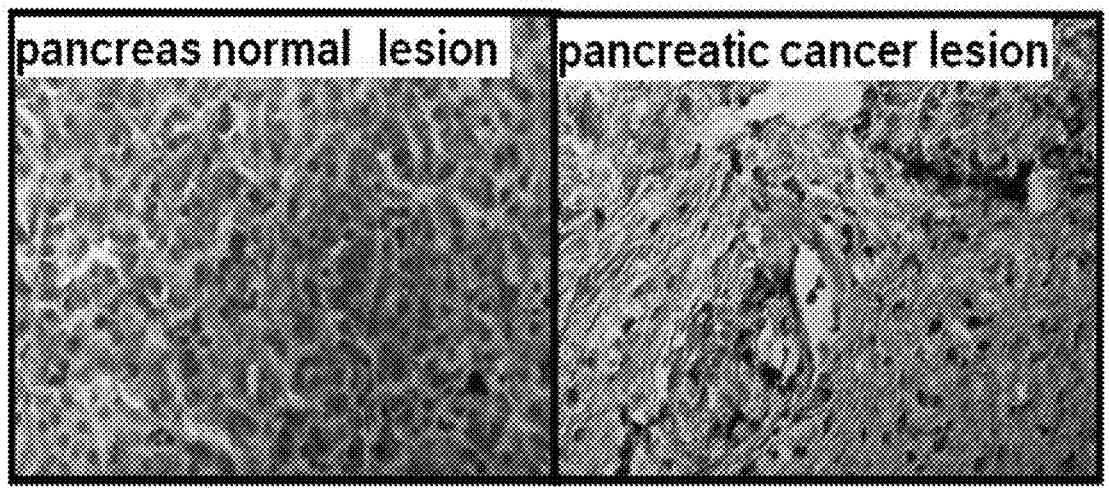
FIG. 11. Immunohistochemical staining by mAb W9 of a surgically removed human pancreatic adenocarcinoma lesion. Frozen sections of a surgically removed human pancreatic adenocarcinoma lesion and normal pancreas tissue from the same patient were stained with mAb W9 (1 µg/ml). (×200).

Immunohistochemical staining with mAb W9 showed that the endoplasmin (Grp94) epitope has a restricted distribution in normal tissue and is expressed in pancreatic adenocarcinoma lesion (FIG. 11). The immunohistochemical analysis has shown that the epitope recognized by mAb W9 has a restricted distribution in normal tissues. Moreover, mAb W9 stained only the surgically removed human pancreatic adenocarcinoma lesion while it didn't stain the normal pancreas tissue from the same patient. Furthermore MDA-MB-231 and MV3 cell line-derived xenograft, respectively, were strongly stained by mAb W9 while no staining was detected in the MCF-7 (FIG. 12).

Example 4

Figure 3A:
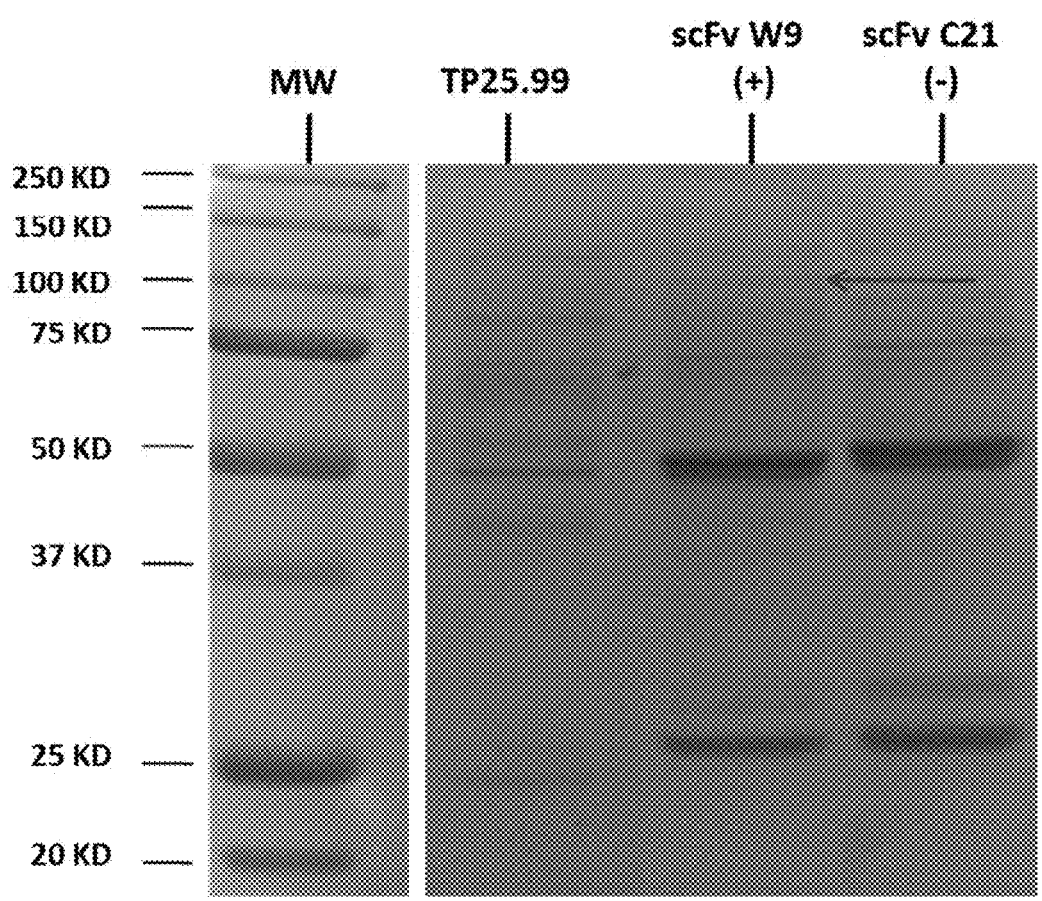
FIGS. 3A and 3B. Identification of endoplasmin as the antigen recognized by scFv W9. A WM1158 melanoma cell lysate was immunoprecipitated with scFv W9. The -HLA class I-specific mAb TP25.99, and the HMW-MAA-specific scFv C21 were used as controls. Proteins in the precipitates were resolved on a reducing 10% SDS-PAGE and stained with Coomassie blue. The 94-KDa was unique to the W9 precipitate (A). Same results were obtained from lysates of T24 (bladder cancer), SUM149 (breast cancer), and SLR21 (renal cancer) cell lines. The specific bands were excised from the SDS gel and analyzed by mass spectrometry. Amino acids 102-115 of SEQ ID NO: 5 and amino acids 434 to 449 of SEQ ID NO: 5 are shown. The human protein identified in the 94-KDa bands is endoplasmin (SEQ ID NO: 5).
Figure 3B:
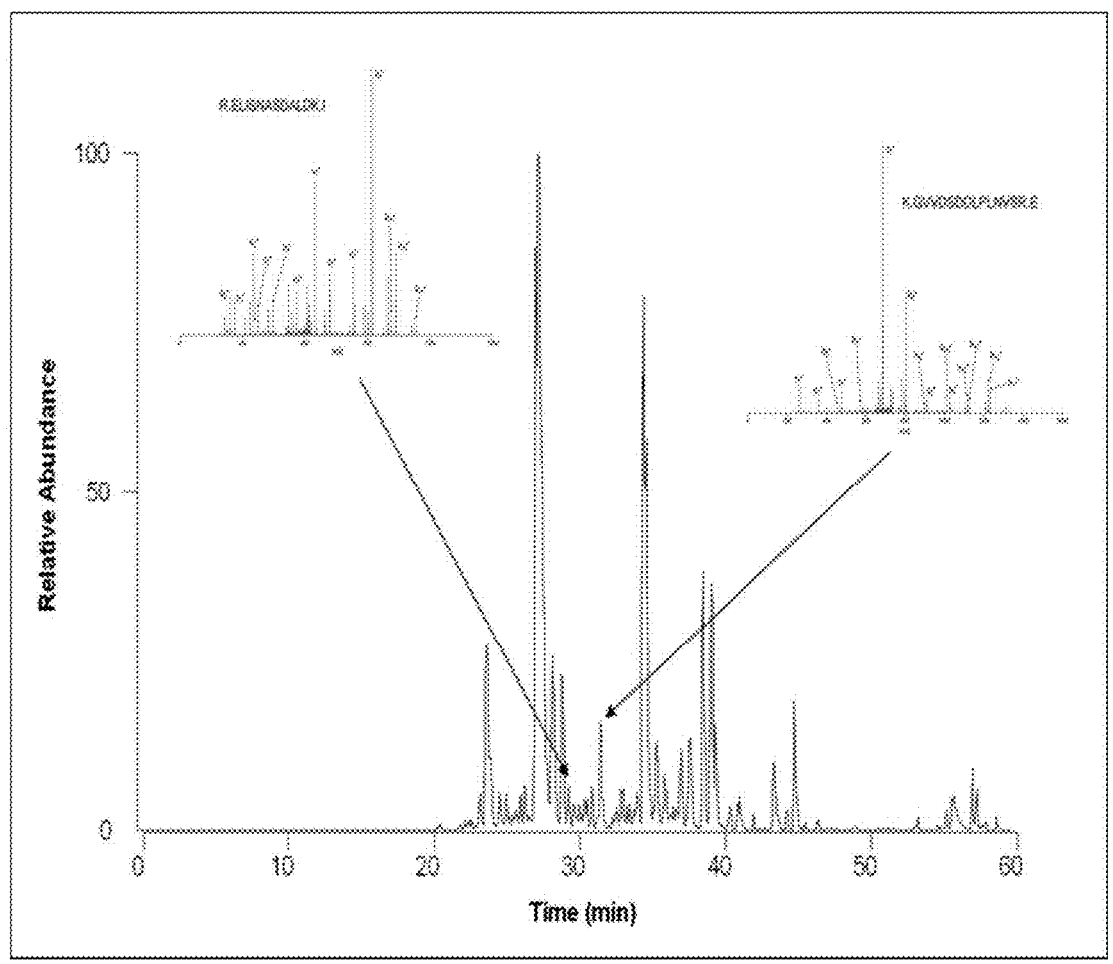

Immunochemical Analysis of the Specificity of scFv W9 and Identification of Grp94 by Tandem Mass Spectrometry The immunoprecipitation of a total cell lysate obtained from WM1158a with scFv W9 resulted in the identification of a unique band at approximately 100 KDa (FIG. 3). scFv #119 was used as a negative control. The same results were obtained utilizing lysates from MV3 (melanoma), SUM149 (basal breast cancer), T24 (bladder cancer), and SLR21 (renal cancer) cell lines. The 100 KDa specific bands immunoprecipitated by scFv W9 from the different cell lysates were excised and in-gel digested with trypsin. The analysis of resulting tryptic peptides by liquid chromatography-tandem mass spectrometry identified two tryptic peptides (ELISNASDALDK (SEQ ID NO: 7) and GVVDSDDLPLNVSR (SEQ ID NO:8)) that are derived uniquely from endoplasmin (Grp94) (FIG. 4).

Figure 9:
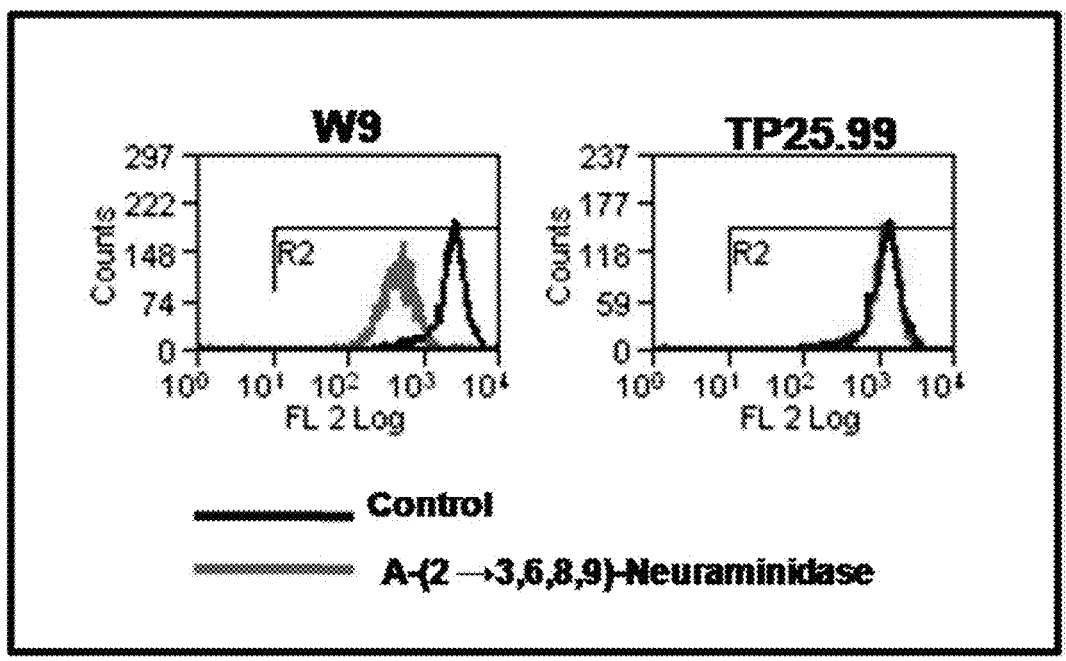
FIG. 9. Role of carbohydrates in the expression of the epitope recognized by mAb W9. Human pancreatic adenocarcinoma MIAPaCa-2 ($5\times10^5$) were incubated with or without 2 µl of α-2(3,6,8.9)-Neuraminidase in 50 µl RPMI1640 medium for 24 hours at 37° C. in a 5% CO2 incubator. The treated cells were then stained with mAb W9 and analyzed by flow cytometry. Cells treated with mAb TP25.99 were used as a control.

The epitope recognized by mAb W9 is critically dependent on sialic acid residue(s), since its reactivity with tumor cells was abrogated following incubation with neuraminidase, but was not affected by other glycosidases (FIG. 9). For these experiments, human pancreatic adenocarcinoma MIAPaCa-2 ($5\times10^5$) were incubated with or without 2 µl of α-2(3,6,8.9)-Neuraminidase in 50 µl RPM I1640 medium for 24 hours at 37° C. in a 5% CO2 incubator. The treated cells were then stained with mAb W9 and analyzed by flow cytometry. Cells treated with mAb TP25.99 were used as a control.

Figure 10:
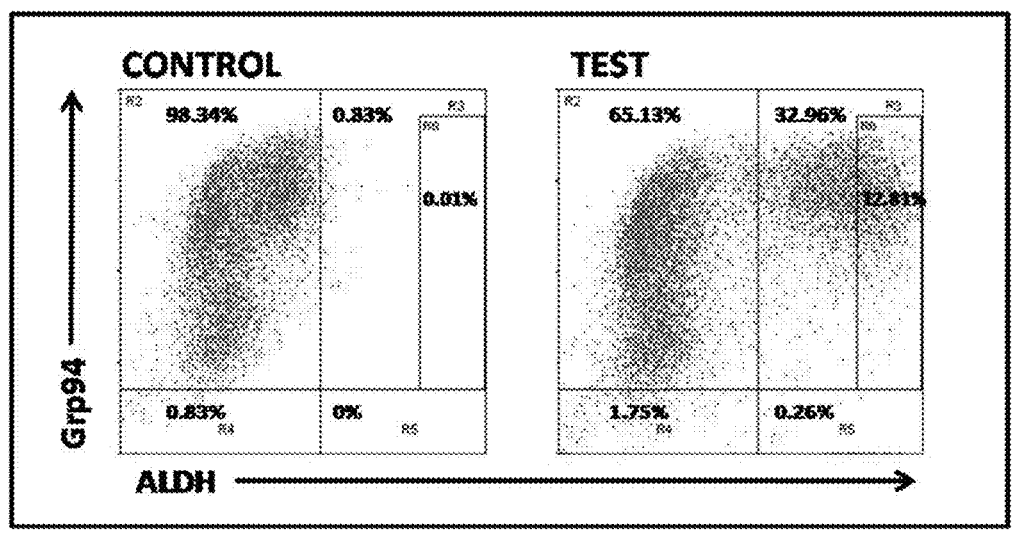
FIG. 10. Expression of the extracellular Endoplasmin (Grp94) epitope recognized by mAb W9 on human pancreatic adenocarcinoma MIAPaCa-2 cancer initiating cells. Human pancreatic adenocarcinoma MIAPaCa-2 cells were incubated with ALDEFLUOR to detect ALDH activity (TEST), and stained with mAb W9. Cells incubated with ALDEFLUOR+DAEB inhibitor and stained with mAb W9 were used as a reference (CONTROL). Human Ig (HIg) were used as a control. The percentage of cancer initiating cells, identified as ALDH$^{bright}$ cells, is indicated.

Human pancreatic adenocarcinoma MIAPaCa-2 cells were incubated with ALDEFLUOR® to detect ALDH activity (TEST), and stained with mAb W9. Cells incubated with ALDEFLUOR®+DAEB inhibitor and stained with mAb W9 were used as a reference (CONTROL). Human Ig (HIg) were used as a control. The percentage of cancer initiating cells, identified as ALDH$^{bright}$ cells, is indicated. Flow analysis showed that the epitope recognized by mAb W9 is expressed by cancer initiating cells since the same antibody bound to the identified ALDH$^{bright}$ cell population (FIG. 10).

Example 5

Effect of Tunicamycin on the Expression of the Determinant Recognized by scFv W9 and Further Characterization of the Epitope Glycosylation plays a role in the expression of the epitope recognized by scFv W9 on endoplasmin (Grp94), since this scFv fragment did not react with COLO38 cells treated with tunicamycin, an inhibitor of N-glycosylation of glycoproteins (FIG. 4). No inhibition was observed with DMSO alone. Furthermore no inhibition was observed for TP25.99 mAb (control) under the same conditions. These data suggest that carbohydrates are essential for the recognition of endoplasmin (Grp94) by scFv W9.

The epitope recognized by mAb W9 is critically dependent on sialic acid residue(s), since its reactivity with tumor cells was abrogated following incubation with neuraminidase, but was not affected by other glycosidases (FIG. 9).

Example 6

Figure 6:
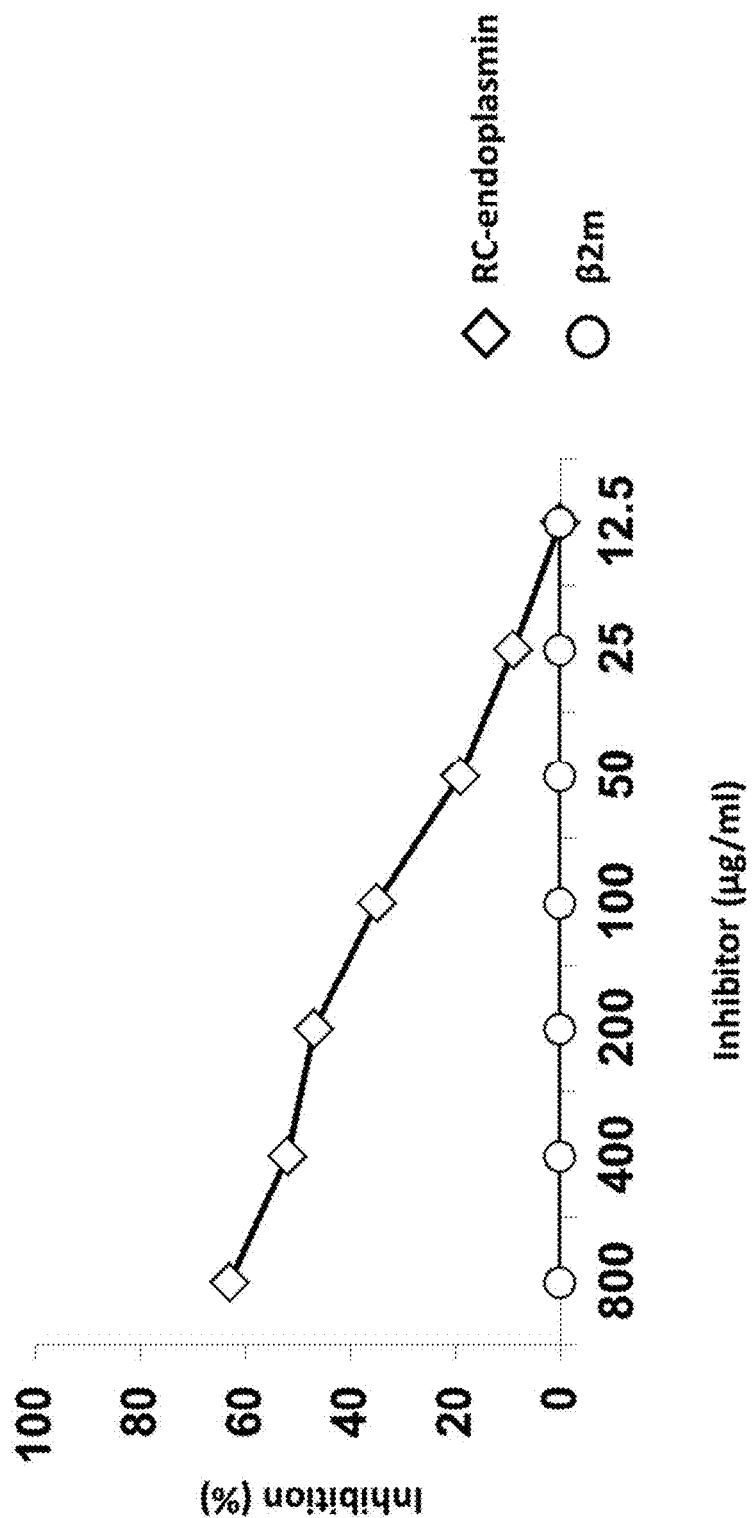
FIG. 6. Dose-dependent inhibition by recombinant canine enodplamsin (Grp94) of scFv W9 binding to COLO38 cells. Two fold dilutions of recombinant canine endoplasmin (Grp94) were preincubated with scFv W9. The mixture was added to 96-well plate seeded with COLO38 cells. The binding of scFv was detected using mAb 9E10 and HPR-goat anti-mouse IgG antibodies. Absorbance was read at 450 nm. B2m was used as a control. Recombinant canine Grp94 specifically inhibits the binding of scFv W9 to COLO38 cells.

Reactivity of scFv W9 with Endoplasmin (Grp94) Canine Recombinant Protein scFv W9 specifically reacted with the endoplasmint (Grp94) canine recombinant protein (RC-Grp94) in a dose dependent fashion (FIG. 5A), since no binding was detected with BSA (negative control, FIG. 5B). Furthermore RC-Grp94 specifically affected the binding of scFv W9 to COLO38 cells in a dose dependent fashion. The inhibition was dose dependent and specific, since β2-microglobuline (negative control) displayed no inhibitory effect (FIG. 6).

Example 7

Effect of Electroporation on Binding of scFv W9

Figure 7A:
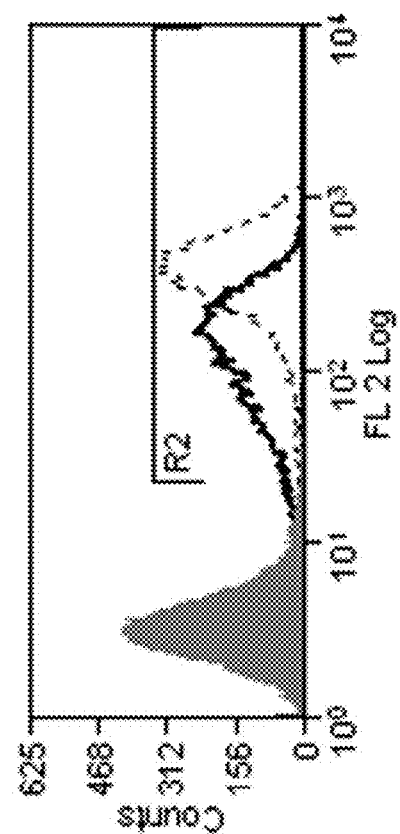
FIGS. 7A and 7B. Effect of transfection of 293 cells with endoplasmin (Grp94) cDNA on binding of scFv W9. 293 cells were transfected with 3 µg of Grp94 HSP90B1 cDNA clone by electroporation. Cells were incubated with scFv W9 and mAb 9E10, followed by incubation with FITC-goat anti-mouse IgG antibodies. Cells were analyzed by flow cytometry. The pCMV6-XL4 vector was used as a control. Untrasfected cells were used as a control. Electroporation increases the binding of scFv W9. The expression of the antigen recognized by scFv is regulated by heat shock.
Figure 7B:
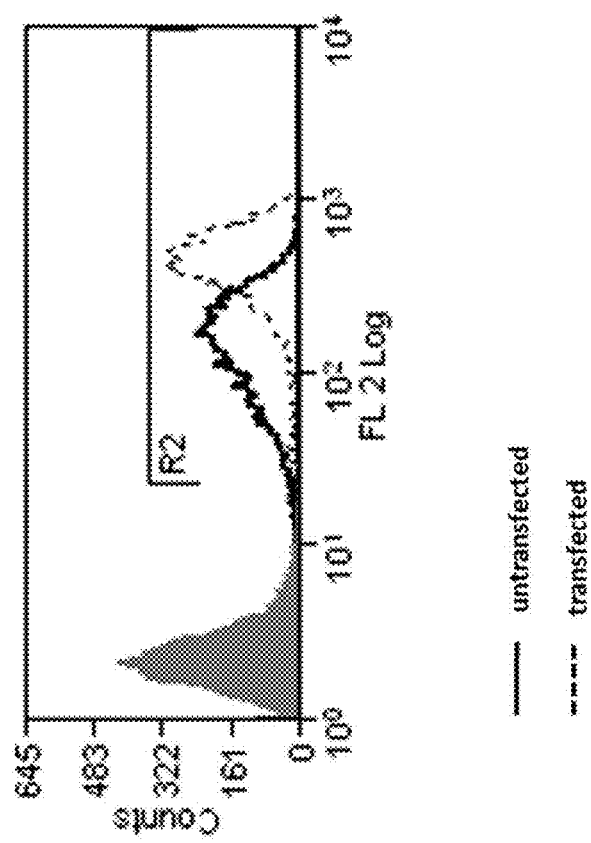

Electroporated 293 cells were transiently transfected with endoplasmin (Grp94) full length cDNA or the vector alone (pCMV-XL4, negative control). The transfection efficiency (94%) was assessed by GFP expression. Cells harvested 24 hours after transfection were incubated with scFv W9 and mAb 9E10, followed by incubation with FITC-goat anti-mouse IgG antibodies. Cells were analyzed by flow cytometry. Untransfected cells were used as a control. A strong increase in the binding of scFv W9 was observed in cells treated with endoplamsin (Grp94) (FIG. 7A) and with the plasmid alone (FIG. 7B). These data suggests that the binding of scFv was increased by electroporation and that the heat shock regulates the expression of the antigen recognized by scFv W9.

Example 8

Effect of shRNA Targeted Against Endoplasmin (Grp94) on Binding of scFv W9

Figure 8B:
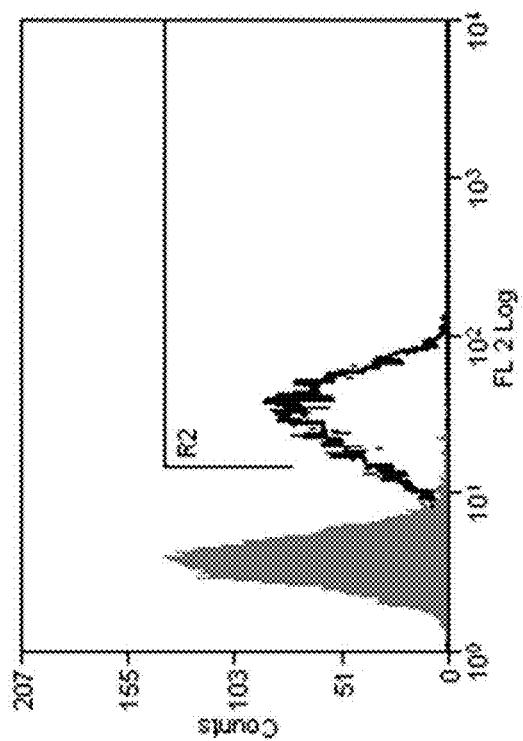
FIGS. 8A and 8B. Effect of transduction of FO-1 cells with endoplasmin (Grp94) shRNA on binding of scFv W9. FO-1 cells were transduced with endoplasmin (Grp94) shRNA and a control shRNA (ABCBS). Cells were incubated with scFv W9 and mAb 9E10, followed by incubation with FITC-goat anti-mouse IgG antibodies. Cells were then analyzed by flow cytometry. endoplasmin (Grp94) shRNA inhibited the binding of scFv W9 compared with the control shRNA.
Figure 8A:
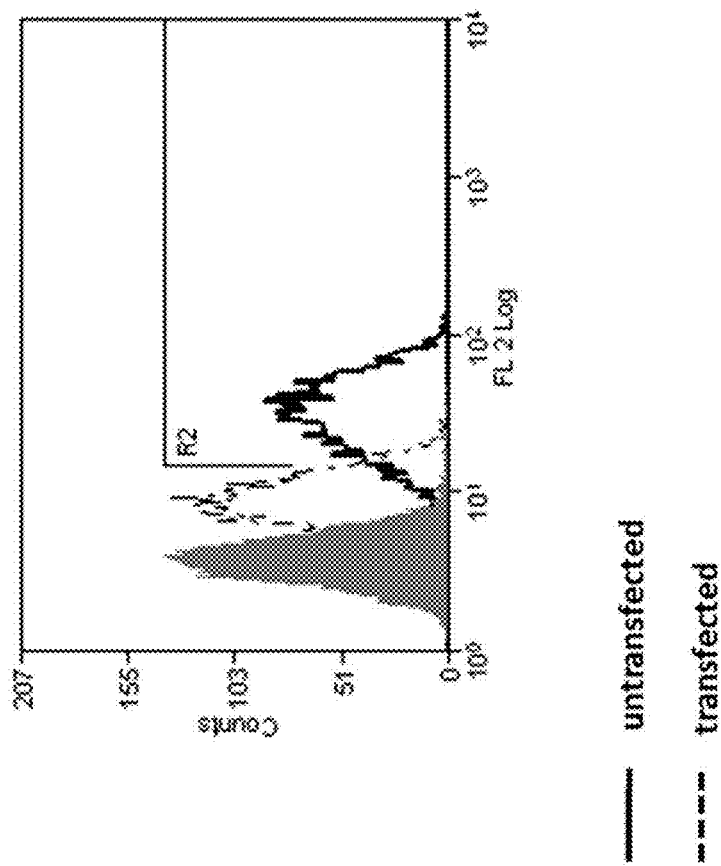

FO-1 cells were transduced with either shRNA to achieve knockdown of endoplasmin (Grp94), or ABCBS shRNA as control. After 72 hours from transduction cells were harvested, incubated with scFv W9 and mAb 9E10, followed by incubation with FITC-goat anti-mouse IgG antibodies. Cells were analyzed by flow cytometry. Grp94 shRNA (FIG. 8A) significantly inhibited the binding of scFv W9 compared with the control shRNA (FIG. 8B).

Example 9

Effect of mAb W9 on Cancer Cells

Figure 13:
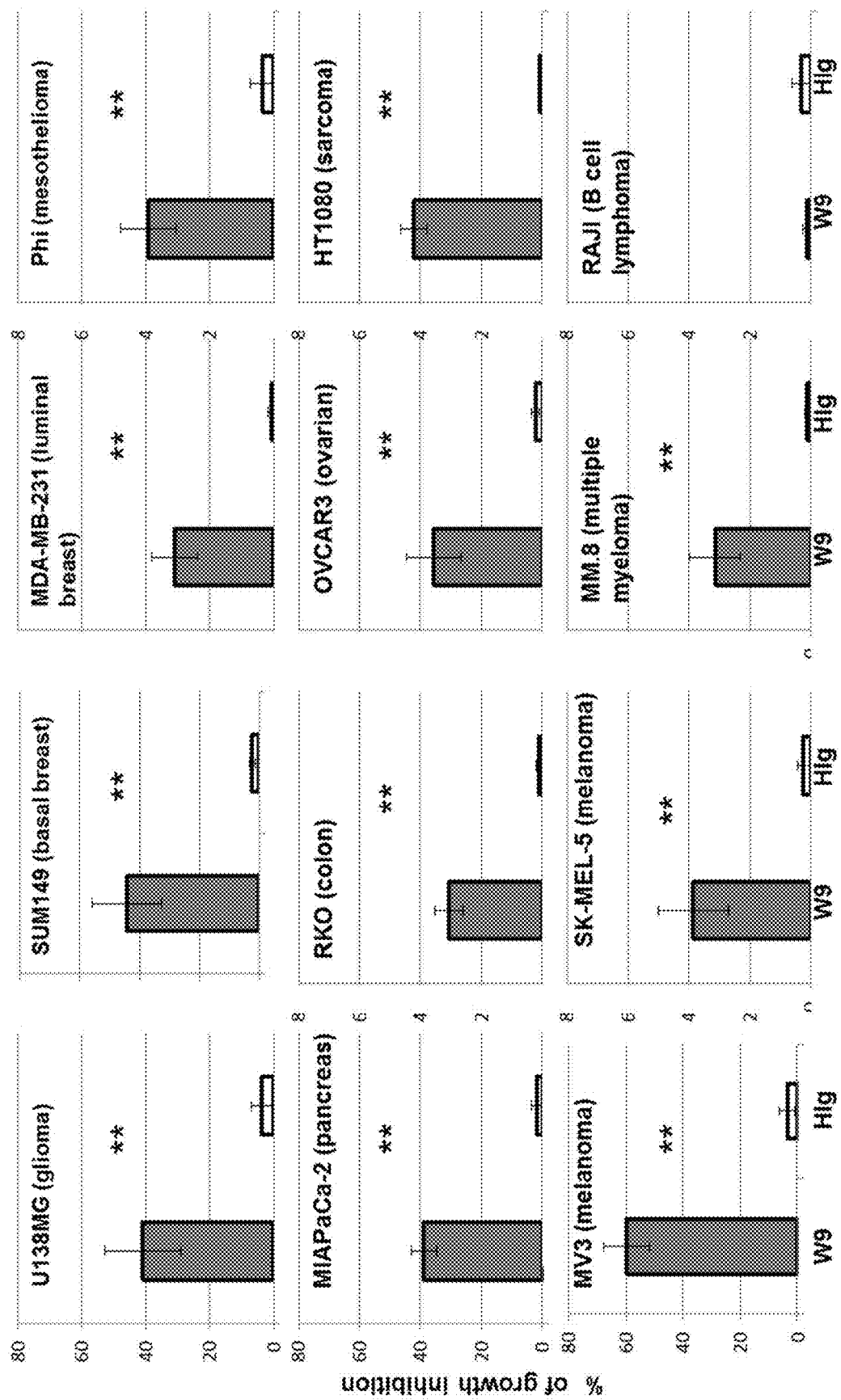
FIG. 13. mAb W9 significantly inhibited the growth of tumor cells expressing endoplasmin (Grp94). Human cancer cells ($1\times10^4$/well) were seeded in a 96-well plate (RPMI 1640 media plus 1% FCS) and treated with mAb W9 (5 µg/ml) for 72 hours. Human Ig (HIg) were used as a control. Cells were then tested by MTT assay. The results are expressed as % of growth inhibition. * p value<0.05; * *p value<0.01.

The effect of mAb W9 on cancer cells was assessed. Specifically, MTT analysis has shown that mAb W9 significantly inhibited the growth of all endoplamsin positive (Grp94+) tumor cell lines tested. However, no effect was observed in a Grp94− Raji cell line. The anti-proliferative effect was specific, since no growth inhibition was observed with human immunoglobulins used as a control (FIG. 13). Thus, mAb W9 inhibited cancer cell proliferation.

Figure 14:
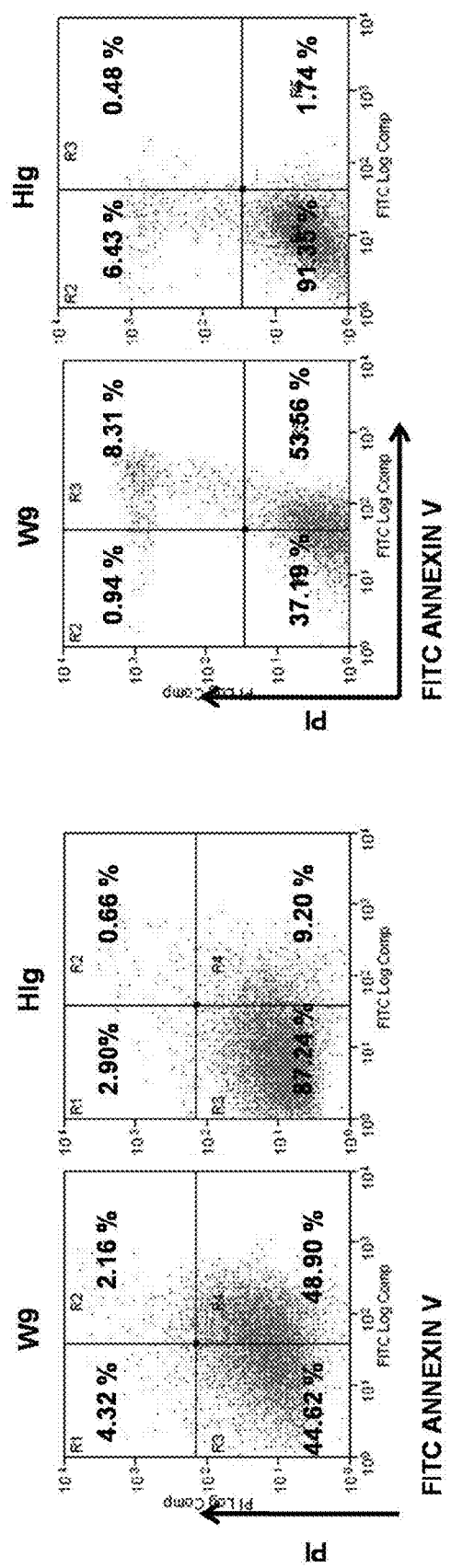
FIG. 14. Induction by mAb W9 antibody of apoptosis in cancer cells. Human MV3 (melanoma) and MIAPaCa-2 (pancreatic adenocarcinoma) cells ($4\times10^5$/ml) were starved for 24 hrs and 3 hrs respectively, then incubated with mAb W9 (50 µg/ml), in RPMI 1640 medium.containing 1.5% FCS. After 6 hrs cells were investigated for the percentage of apoptotic cells by staining with Annexin V/PI. Cells were analyzed by flow cytometry. Human Ig (HIg) were used as a negative control.
Figure 15:
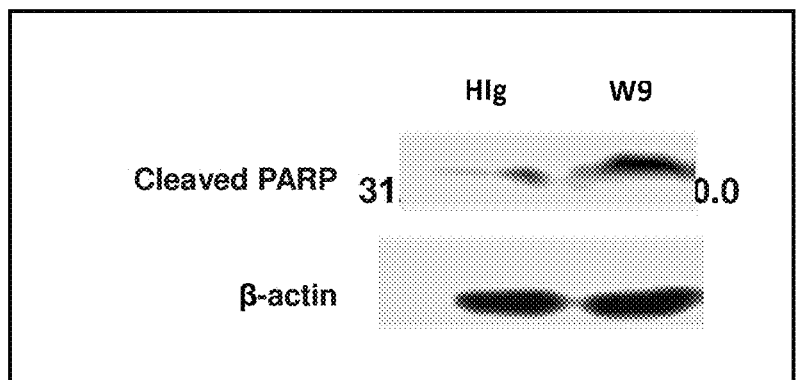
FIG. 15. Induction by mAb W9 antibody of cleaved PARP in human melanoma M21 cells. Human melanoma M21 cells ($4\times10^5$/ml) were incubated with mAb W9 (5 µg/ml), in RPMI 1640 medium containing 1.5% FCS for 72 hrs. Cell lysates were tested in a Western blot analysis for cleaved PARP. β-actin was used as the loading control. mAb W9 strongly increased the expression of cleaved PARP.
Figure 16:
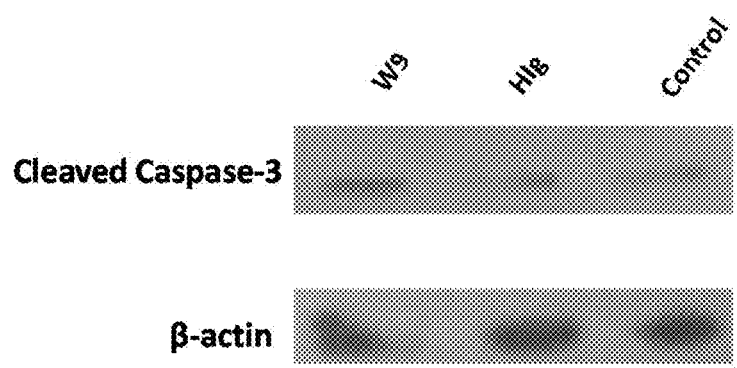
FIG. 16. Induction by mAb W9 antibody of cleaved caspase-3 in human melanoma MV3 cells. Human melanoma MV3 cells ($4\times10^5$/ml) were starved for 24 hrs, then incubated with mAb W9 (50 µg/ml), in RPMI 1640 medium containing 1.5% FCS. Cell lysates were tested in Western blot for cleaved caspase-3. β-actin was used as the loading control. The density of resultant bands was determined with IMAGJ® software, normalized to that of β-actin, are shown below the respective bands. mAb W9 strongly increased the expression of cleaved caspase-3. No effect was detected in cells treated with HIg.
Figure 17:
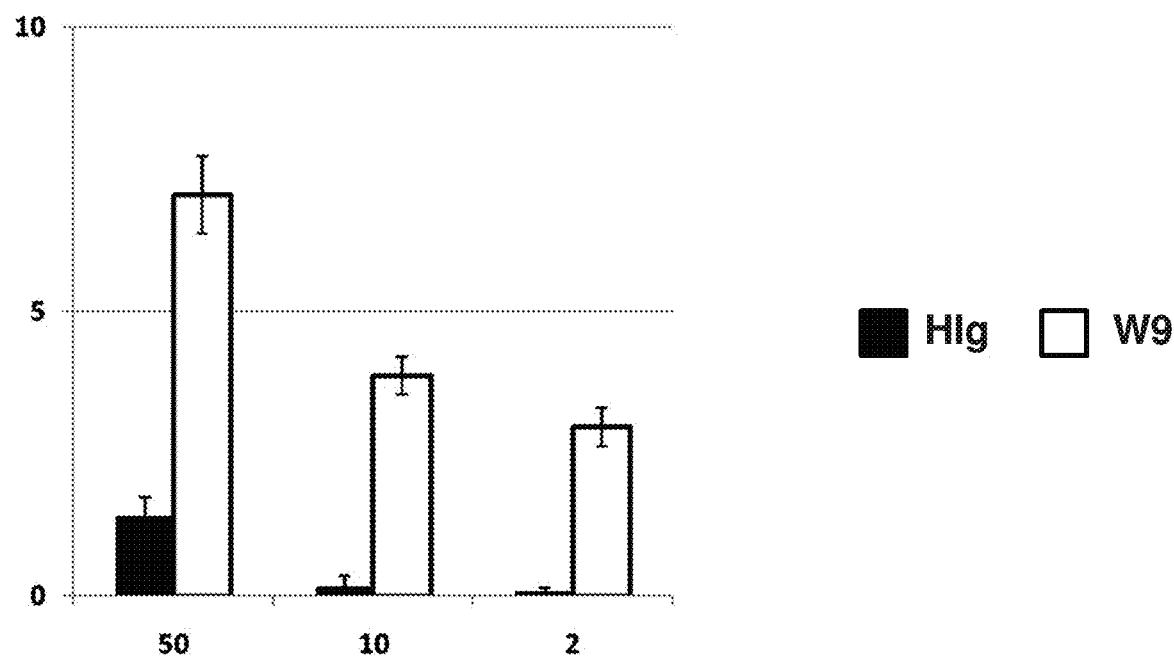
FIG. 17. Cell-dependent lysis of human melanoma MV3 cells mediated by mAb W9. Human melanoma MV3 cells were labeled with 50 μCi of $^{51}$Cr and resuspended at the density of $0.4 \times 10^6$ cells/ml and combined with mAb W9 (50, 10, 2 μg/ml) in a 96-well tissue culture-U-bottom assay plate. Human Ig (HIg) were used as a control. Following 30 minutes of incubation at 4° C., PBMC (40:1 E:T) were added and incubated for 4 hrs at 37° C. in a $CO_2$ incubator. $^{51}$Cr release was determined by counting the ell free supernatant in a Packard TOPCOUNT™ Microplate Scintillation Counter.
Figure 18:
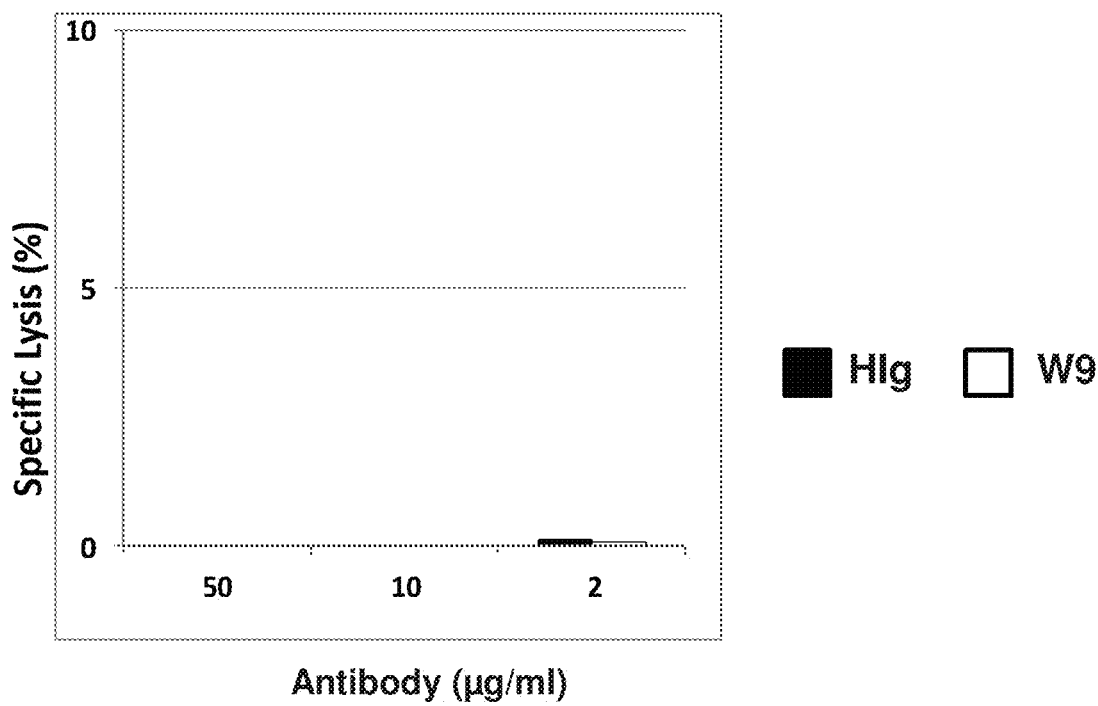
FIG. 18. Complement-dependent lysis of human melanoma MV3 cells mediated by mAb W9. Human melanoma MV3 cells were labeled with 50 μCi of $^{51}$Cr and resuspended at the density of $1 \times 10^6$ cells/ml. The target cells were incubated with mAb W9 (50, 10, 2 μg/ml) in presence of human serum complement. Human Ig (Hig) were used as control. Following 2 hrs of incubation at 37° C. in a $CO_2$ incubator, $^{51}$Cr release was determined by counting the cell free supernatant in a Packard TOPCOUNT™ Microplate Scintillation Counter.

Flow analysis has shown that mAb W9 induced apoptosis in human melanoma MV3 and pancreatic cancer MIAPaCa-2 cells (48.90% and 53.56% of apoptosis respectively). Furthermore, Western blot analyses showed a significant increase of the expression of cleaved Caspase-3 and cleaved PARP in cells treated with mAb W9 (FIGS. 14, 15 and 16). Thus, mAb W9 induced apoptosis in cancer cells. However, mAb W9 did not mediate cell-nor complement-dependent lysis of target cells (FIGS. 17 and 18).

Figure 19:
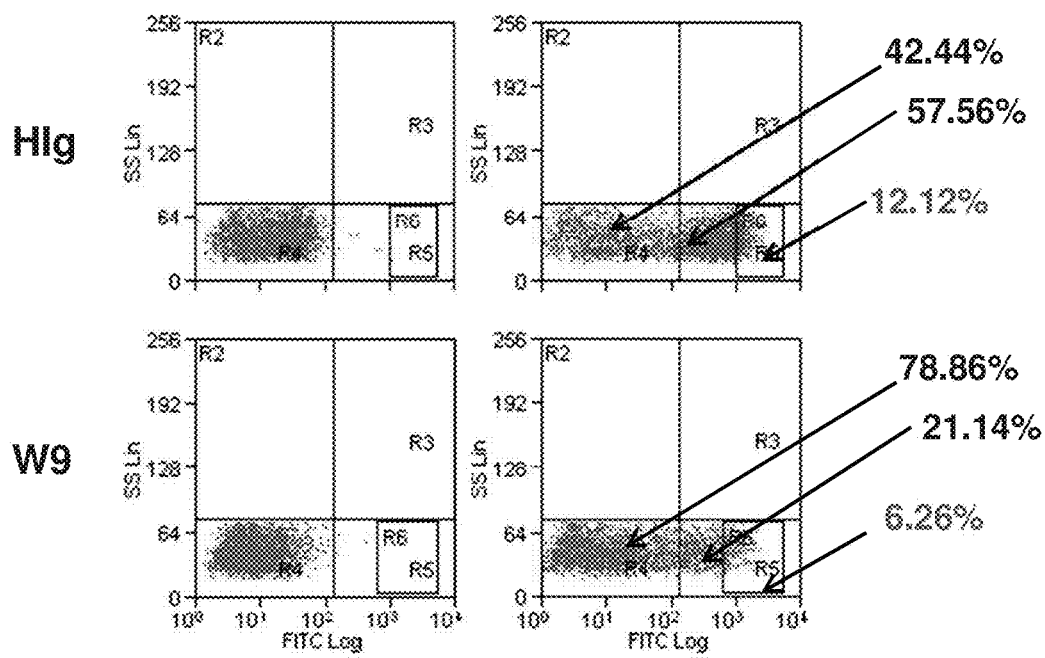
FIG. 19. Inhibition by mAb W9 of human pancreatic adenocarcinoma MIAPaCa-2 cancer initiating cell in vitro proliferation. Human pancreatic adenocarcinoma MIAPaCa-2 cells were incubated with mAb W9 (25 μg/ml), for 48 hrs at 37° C. Cells were then harvested and stained with ALDEFLUOR® (TEST). Cells stained with ALDEFLUOR®+DAEB were used as a reference (CONTROL). Human Ig (HIg) were used as a control. The percentage of cancer initiating cells, identified as ALDH$^{bright}$ cells, is indicated.
Figure 20:
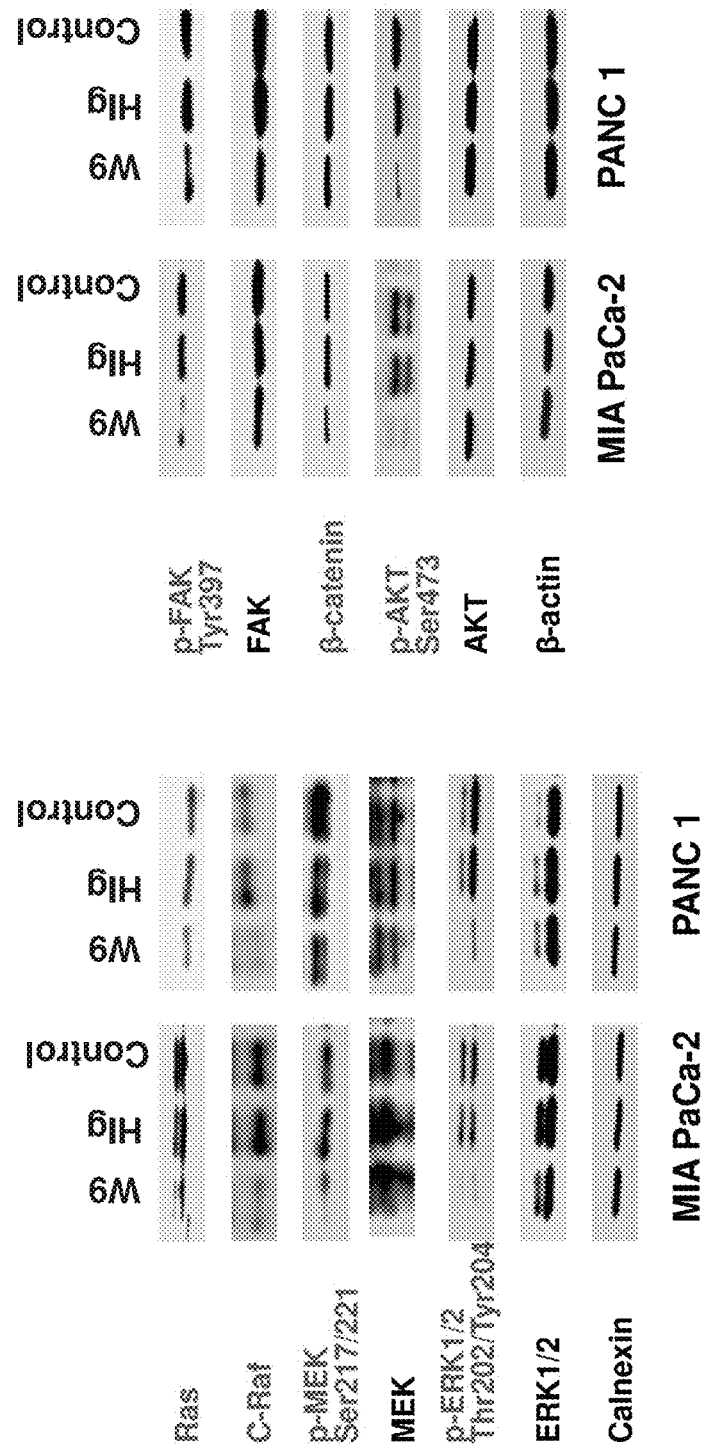
FIG. 20. Inhibition by mAb W9 of signaling pathways RAS-MEK-ERK and FAK in pancreatic MIAPaCa-2 and PANC 1 cells. The human pancreatic MIAPaCa-2 and PANC 1cells were seeded at the concentration of $1.0 \times 10^5$ per well in a 6-well plate in RPMI 1640 medium with 5% FCS and incubated with either the W9 supernatant, the control supernatant, or untreated for 48 hrs at 37° C. Cell lysate were tested in western blot with anti-RAS, C-Raf, phosphorylated (p)-ERK1/2, ERK1/2, (p)-FAK (Tyr397), FAK, β-catenin, p-AKT (Ser473) and AKT mAbs. Calnexin and β-actin was used as the loading control.

In addition, mAb W9 inhibited proliferation of human pancreatic adenocarcinoma MIAPaCa-2 cancer initiating cells. Flow analysis has shown that in cells treated with mAb W9, the percentage of cancer initiating cells, defined as $ALDH^{bright}$ cells, was reduced by 50% when compared with human immunoglobulins (negative control) (FIG. 19). mAb W9 treated cells had a decreased level of Ras, C-Raf, PCKα, β-catenin, and Bcl-2. Moreover, mAb W9 treatment inhibited the activation of Akt, Erk, Mek, Fak, and Met (FIG. 20-22). In a pull-down assay using mAb W9, endoplsmin (Grp94) was co-immuno-precipitated with Met, Ras, and C-Raf (FIG. 23).

Figure 24:
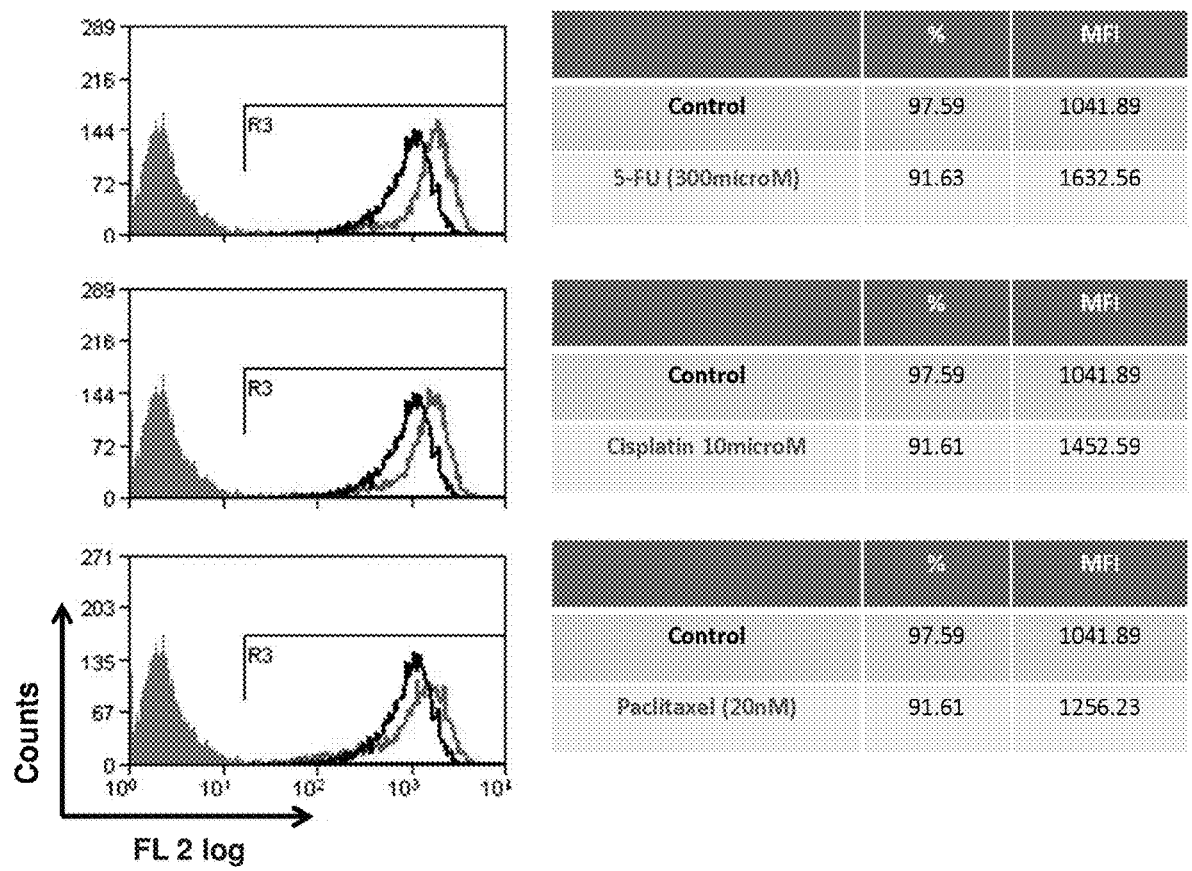
FIG. 24. Enhancement by chemotherapeutic agents of endoplasmin (Grp94) expression by UACC-257 melanoma cells. Human melanoma UACC-257 cells ($2 \times 10^5$/ml) were incubated in RPMI 1640 medium containing 10% FCS with 5-FU (300 μM), Cisplatin (10 μM), and Paclitaxel (20 nM) for 48 hrs. Cells were harvested, stained with mAb W9 and analyzed by flow cytometry. Untreated cells were used as control. Percentage of stained cells and mean fluorescence intensity (MFI) are indicated.

H&E stained tissue sections were analyzed for the cumulative area of the metastatic nodules present in 5 randomly selected, 200× fields/section using an OLYMPUS® BX51 microscope (OLYMPUS® UK Ltd.). SPOT IMAGING SOFTWARE® Advanced (Diagnostic Instruments, Inc.) was used to measure and calculate the mean tumor area for each group, and these values for MV3 tumor are provided in the bar graphs±SD. mAbW9 treated mice had a statistically significant (about 50%) reduction in the area of metastases compared to that treated with the isotype control antibody (FIG. 24).

Figures 25A, 25B:
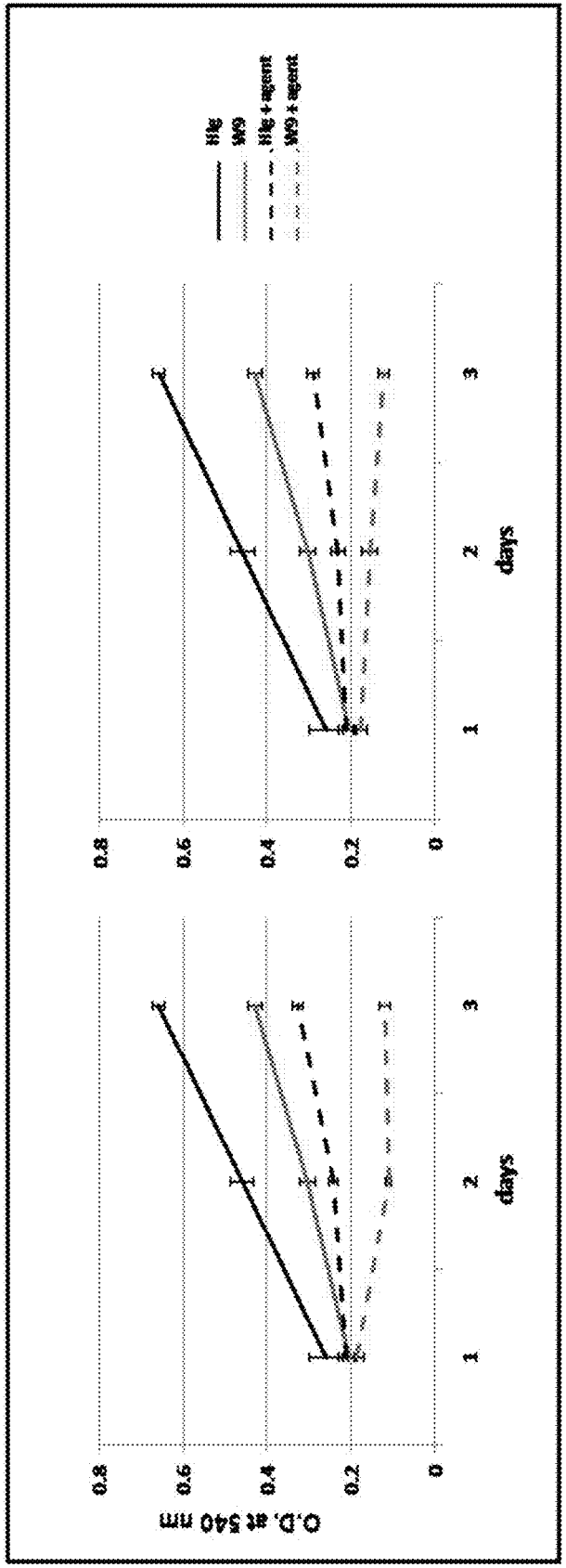
FIGS. 25A and 25B. Inhibition by mAb W9 in combination with 5-FU and cyclopamine of human pancreatic adocarcinoma MIAPaCa-2 cell proliferation. Human pancreatic adenocarcinoma MIAPaCa-2 cells were seeded ($2.5 \times 10^3$ cells per well) in a 96-well plate (RPMI 1640 media plus 5% FCS) and treated with mAb W9 (5 μg/ml) in combination with 5-FU (10 μM) (A.), or cyclopamine (20 μM) (B.) for for 1, 2, 3 days at 37° C. in a 5% CO2 atmosphere. Cells were then tested by MTT assay. The O.D. values at 540 nm indicate the living cells.
Figure 26:
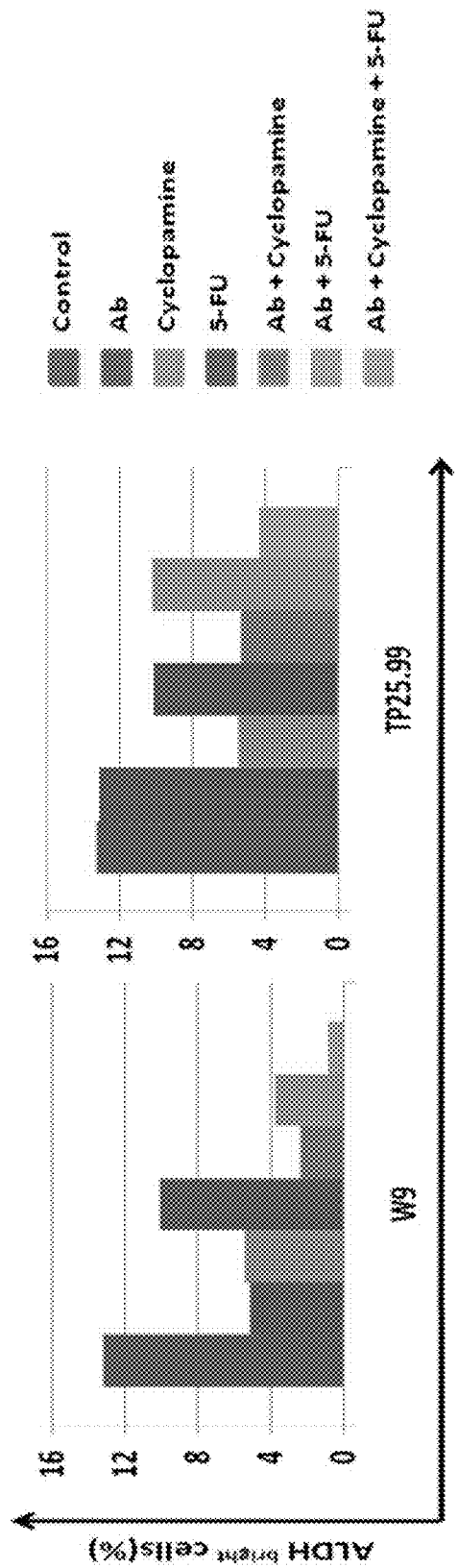
FIG. 26. Inhibition by mAb W9 in combination with 5-FU and cyclopamine of human pancreatic adenocarcinoma MIAPaCa-2 cancer initiating cell in vitro proliferation. Human pancreatic adenocarcinoma MIAPaCa-2 cells were incubated with mAb W9 (25 μg/ml), cyclopamine (20 μM), and 5-FU (10 μM) for 48 hrs at 37° C. Cells were then stained with ALDEFLUOR with or without the DEAB inhibitor to identify ALDH$^{bright}$ cells. The anti-HLA class I mAb TP25.99 was used as a control. The percentage of cancer initiating cells, identified as ALDH$^{bright}$ cells, is indicated.
Figure 27:
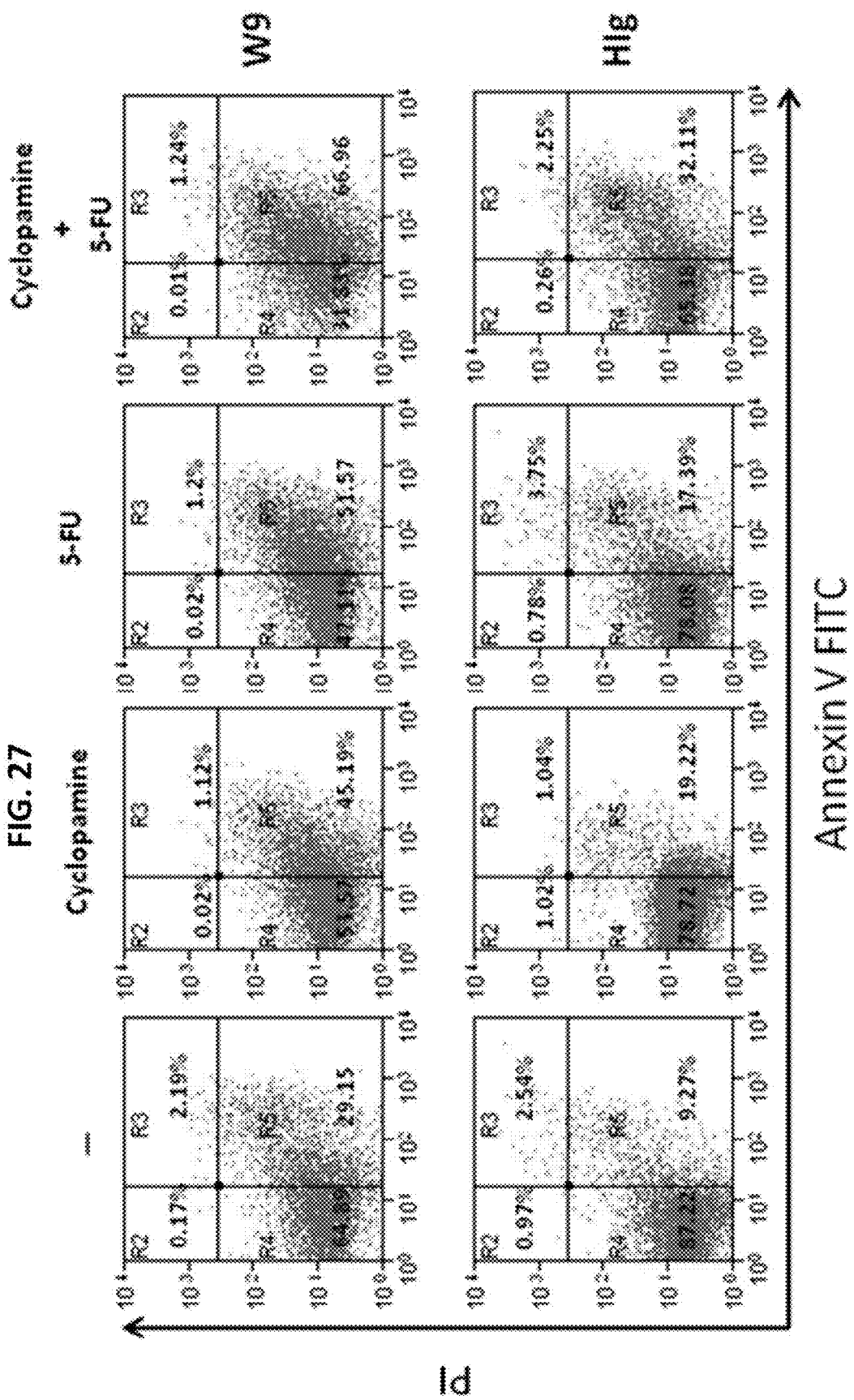
FIG. 27. Induction by mAb W9 in combination with 5-FU and cyclopamine of apoptosis in pancreatic adenocarcinoma MIAPaCa-2 cells. Human pancreatic adenocarcinoma MIAPaCa-2 cells ($4 \times 10^5$/ml) were starved for 3 hrs then incubated with mAb W9 (10 μg/ml), cyclopamine (20 μM), and 5-FU (10 μM) in RPMI 1640 medium.containing 1.5% FCS. After 24 hrs cells were investigated for the percentage of apoptotic cells by staining with Annexin V/PI. Cells were analyzed by flow cytometry. HIg were used as a negative control.
Figure 28:
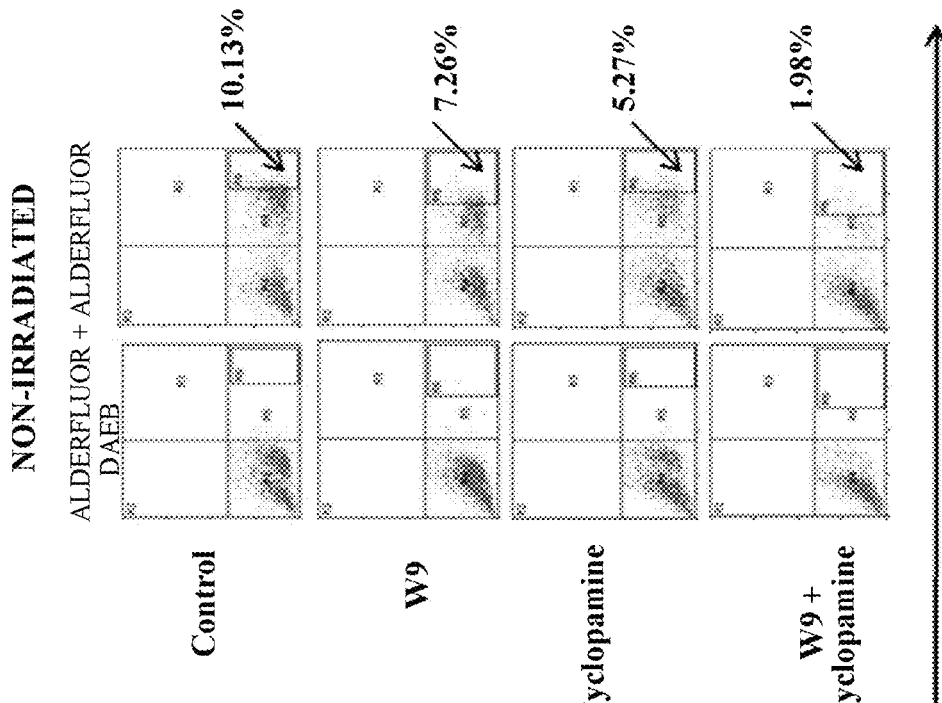
FIGS. 28A and 28B. Inhibition by mAb W9 in combination with radiation and cyclopamine of human pancreatic adenocarcinoma MIAPaCa-2 cancer initiating cell in vitro proliferation. Human pancreatic adenocarcinoma MIAPaCa-2 cells ($4 \times 10^5$/ml) were irradiated at the dose of 20Gy (panel A.) and incubated with mAb W9 (10 μg/ml) and cyclopamine (20 μM) for 72 hrs at 37° C. Cells were then stained with ALDEFLUOR with or without the DEAB inhibitor to identify ALDH$^{bright}$ cells. Non-irradiated cell were used as a control (panel B.). The percentage of cancer initiating cells, identified as ALDH$^{bright}$ cells, is indicated.

Endoplasmin (Grp94) expression was enhanced by chemotherapeutic agents. Flow analysis has shown that treatment with 5-fluorouracil (FU), Cisplatin, and Paclitaxel increased the surface expression of Endoplasmin (Grp94). The effect was specific (FIG. 25). MTT results showed that mAb W9 in combination with 5-FU and cyclopamine, respectively, is more effective than each agent alone in inhibiting pancreatic adenocarcinoma cell growth (FIG. 26). Flow analysis also showed that inhibition of cancer initiating cell growth by mAb W9 was enhanced by cyclopamine and 5-FU. Approximately 90% growth inhibition of $ALDH^{bright}$ cells was detected after incubation with mAb W9, cyclopamine and 5-FU. In contrast, the inhibition was only 50% in the cultures incubated with mAb W9 or cyclopamine individually, 20% in the culture incubated with 5-FU and 70% in the cultures incubated with mAb W9 in combination with cyclopamine or 5-FU (FIG. 27). Flow analysis also showed that the induction of apoptosis by mAb was enhanced by cyclopamine and 5-FU. Apoptosis was induced in 70% of cells by mAb W9 in combination with cyclopamine and 5-FU. However, apoptosis was induced in less than 35% of the cells treated with 5-FU, cyclopamine, or a combination of 5-FU and cyclopamine (FIG. 28).

Figure 29:
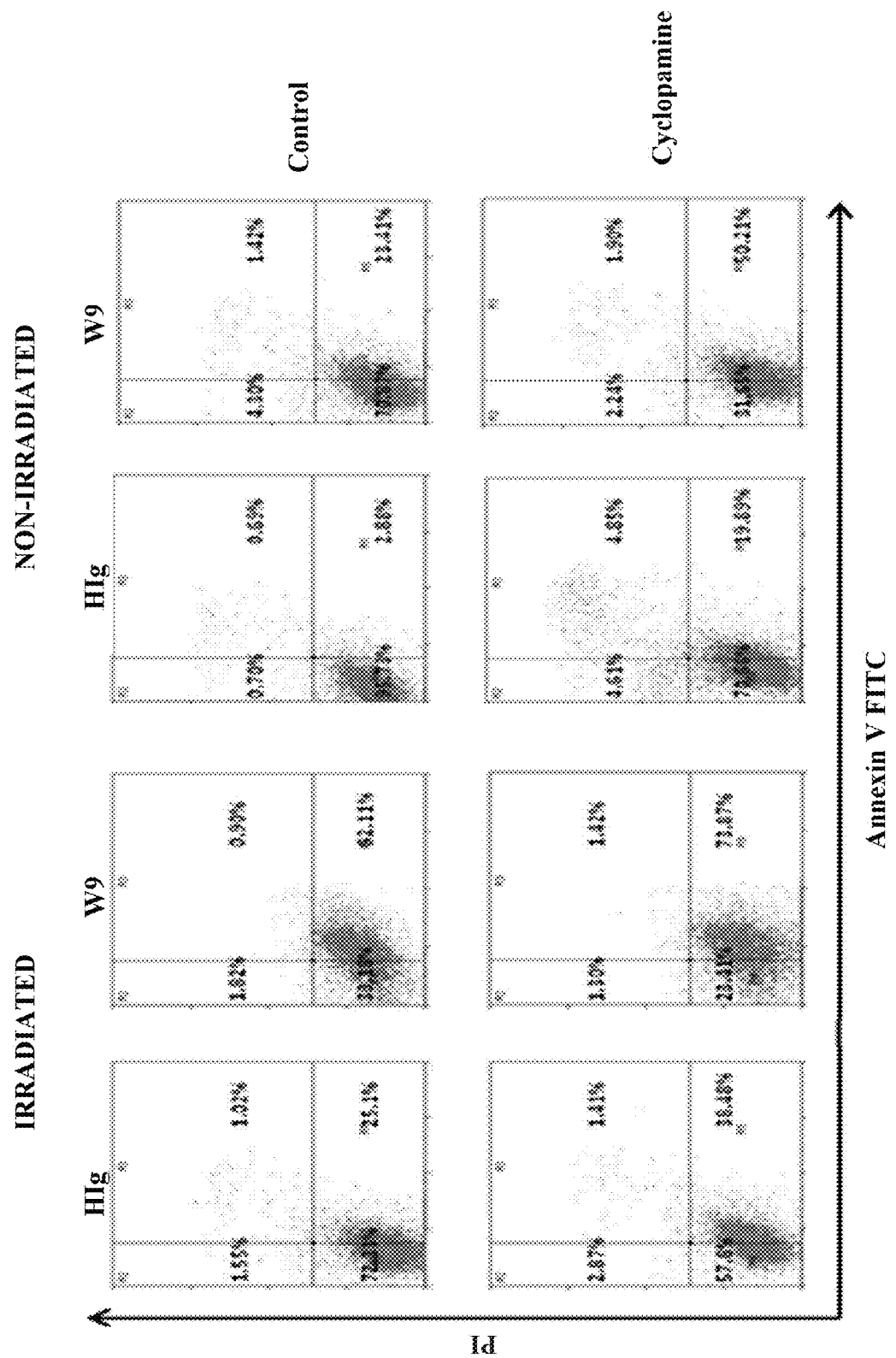
FIG. 29. Induction by mAb W9 in combination with radiation and cyclopamine of apoptosis in pancreatic adenocarcinoma MIAPaCa-2 cells. Human pancreatic adenocarcinoma MiaPaCa-2 cells ($4 \times 10^5$/ml) were irradiated at the dose of 20Gy and incubated with mAb W9 (20 μg/ml) and cyclopamine (20 μM). After 8 hrs cells were tested for the percentage of apoptotic cells by staining with Annexin V/PI.

Flow analysis also showed that inhibition of cancer initiating cell growth by mAb W9 was enhanced by radiation and cyclopamine Approximately 90% growth inhibition of $ALDH^{bright}$ cells was detected after treatment with mAb W9, in combination with radiation and cyclopamine. In contrast only the inhibition was approximately 50% in the cultures treated with mAb W9 or cyclopamine individually, and less than 30% in the cultures only treated with radiation (FIG. 29). Flow analysis showed that the induction of apoptosis by mAb was enhanced by radiation and cyclopamine. Apoptosis was induced in 73.87% of cells by mAb W9 in combination with radiation and cyclopamine, but in less than 25% by mAb W9 alone (FIG. 30).

The effect of mAb W9 treatment on Ras and C-Raf protein levels was also examined. Ras and C-Raf levels were enhanced by cyclopamine and 5-FU. A synergistic effect was found in the inhibition of the activation of Mek, Erk, and Akt (FIG. 31). The effect of mAb W9 treatment in inhibiting Ras and GLI1 protein levels as well as the activation of Erk, and Akt was enhanced by radiation and cyclopamine (FIG. 32).

Example 10

Endoplasmin-Specific Monoclonal Antibodies for the Treatment of Cancer

This example describes the use of endoplasmin-specific human monoclonal antibodies for the treatment of cancers that exhibit overexpression of endoplasmin (referred to herein as a "endoplasmin-positive" cancer), including, but not limited to melanoma, breast cancer, head and neck squamous cell carcinoma, renal cancer, lung cancer, glioma, bladder cancer, ovarian cancer or pancreatic cancer. Patients diagnosed with an endoplasmin-positive cancer can be treated according to standard procedures in the art. Generally, treatment options include surgery, radiation therapy, chemotherapy, immunotherapy or interferon therapy.

In this example, patients diagnosed with an endoplasmin-positive melanoma are administered an immunoconjugate comprising an endoplasmin-specific human monoclonal antibody linked to *Pseudomonas* exotoxin (PE). Preparation of PE immunoconjugates has been described (see, for example, U.S. Pat. No. 7,081,518 and U.S. Pre-Grant Publication No. 2005/0214304, which are herein incorporated by reference). In some patients, the immunoconjugate is administered by intravenous bolus injection every other day for a total of three to six doses. In other patients, the immunoconjugate is administered by continuous intravenous infusion over the course of ten days. The dose of immunoconjugate administered to a patient varies depending on the weight and gender of the patient, and mode and time course of administration. Following treatment, patients are evaluated for cancer progression (including tumor growth and metastasis) and other clinical signs of illness. Patients can be treated with the immunoconjugate alone, or in combination with one or more standard cancer treatments. For example, a patient that has undergone surgery to remove the melanoma can subsequently be treated with the immunoconjugate.

It will be apparent that the precise details of the methods or compositions described may be varied or modified without departing from the spirit of the described invention. We claim all such modifications and variations that fall within the scope and spirit of the claims below.

The invention claimed is:

1. An isolated chimeric molecule comprising a human monoclonal antibody, or antigen binding fragment thereof, linked to an interferon,
wherein the human monoclonal antibody or the antigen binding fragment thereof comprises a heavy chain variable domain and a light chain variable domain, and wherein:
a) the heavy chain variable domain comprises amino acids 26-33 of SEQ ID NO: 1, amino acids 51-58 of SEQ ID NO: 1, and amino acids 97-103 of SEQ ID NO: 1;
b) the light chain variable domain comprises amino acids 27-32 of SEQ ID NO: 2, amino acids 50-52 of SEQ ID NO: 2, and amino acids 89-97 of SEQ ID NO: 2; and
c) the human monoclonal antibody or the antigen binding fragment thereof specifically binds human endoplasmin.

2. The isolated chimeric molecule of claim 1, wherein the interferon (IFN) is IFN-α, IFN-β, or IFN-γ.

3. The isolated chimeric molecule of claim 1, wherein the heavy chain variable domain of the antibody comprises SEQ ID NO: 1.

4. The isolated chimeric molecule of claim 1, wherein the light chain variable domain of the antibody comprises SEQ ID NO: 2.

5. The isolated chimeric molecule of claim 1, wherein the antigen-binding fragment is a Fab fragment, a Fab' fragment, a F(ab')₂ fragment, a single chain Fv protein (scFv), or a disulfide stabilized Fv protein (dsFv).

6. The isolated chimeric molecule of claim 1, wherein the human monoclonal antibody is an IgG.

7. The isolated chimeric molecule of claim 1, wherein the antibody or the antigen binding fragment thereof is labeled.

8. A composition comprising the isolated chimeric molecule of claim 1, and a pharmaceutically acceptable carrier.

9. The isolated chimeric molecule of claim 1, wherein the IFN is IFN-α.

10. The isolated chimeric molecule of claim 9, wherein the heavy chain variable domain comprises SEQ ID NO: 1.

11. The isolated chimeric molecule of claim 9, wherein the light chain variable domain comprises SEQ ID NO: 2.

12. The isolated chimeric molecule of claim 9, wherein the antigen-binding fragment is a Fab fragment, a Fab' fragment, a F(ab')₂ fragment, a single chain Fv protein (scFv), or a disulfide stabilized Fv protein (dsFv).

13. The isolated chimeric molecule of claim 9, wherein the human monoclonal antibody is an IgG.

14. The isolated chimeric molecule of claim 9, wherein the human monoclonal antibody or the antigen binding fragment thereof is labeled.

15. A composition comprising the isolated chimeric molecule of claim 9, and a pharmaceutically acceptable carrier.

* * * * *